US007572600B2

(12) United States Patent
Berahovich et al.

(10) Patent No.: US 7,572,600 B2
(45) Date of Patent: Aug. 11, 2009

(54) ENZYMATIC ACTIVITIES IN CHEMOKINE-MEDIATED INFLAMMATION

(75) Inventors: Robert D. Berahovich, Berkeley, CA (US); Zhenhua Miao, San Jose, CA (US); Brett Premack, San Francisco, CA (US); Thomas J. Schall, Palo Alto, CA (US)

(73) Assignee: Chemocentryx, Inc., Mt. View, CA (US)

( * ) Notice: Subject to any disclaimer, the term of this patent is extended or adjusted under 35 U.S.C. 154(b) by 486 days.

(21) Appl. No.: 11/198,935

(22) Filed: Aug. 4, 2005

(65) Prior Publication Data

US 2006/0063223 A1 Mar. 23, 2006

Related U.S. Application Data

(60) Provisional application No. 60/598,959, filed on Aug. 4, 2004.

(51) Int. Cl.
*C12Q 1/00* (2006.01)
*C12Q 1/37* (2006.01)
(52) U.S. Cl. ...................................... 435/23
(58) Field of Classification Search ............... 435/4, 435/23
See application file for complete search history.

(56) References Cited

U.S. PATENT DOCUMENTS

| 4,458,066 | A | 7/1984 | Caruthers et al. |
|---|---|---|---|
| 4,733,655 | A | 3/1988 | Smal |
| 4,800,882 | A | 1/1989 | Gianturco |
| 4,816,567 | A | 3/1989 | Cabilly et al. |
| 4,886,062 | A | 12/1989 | Wiktor |
| 5,124,350 | A | 6/1992 | Djuric et al. |
| 5,284,746 | A | 2/1994 | Sledziewski et al. |
| 5,419,760 | A | 5/1995 | Narciso, Jr. |
| 5,422,426 | A | 6/1995 | DiMarchi et al. |
| 5,429,634 | A | 7/1995 | Narciso, Jr. |
| 5,530,101 | A | 6/1996 | Queen et al. |
| 5,545,806 | A | 8/1996 | Longberg et al. |
| 5,563,762 | A | 10/1996 | Leung et al. |
| 5,569,825 | A | 10/1996 | Longberg et al. |
| 5,585,089 | A | 12/1996 | Queen et al. |
| 5,693,761 | A | 12/1997 | Queen et al. |
| 5,693,762 | A | 12/1997 | Queen et al. |
| 5,736,524 | A | 4/1998 | Content et al. |
| 6,329,510 | B1 * | 12/2001 | Qin et al. ............... 530/388.22 |
| 6,723,538 | B2 * | 4/2004 | Mack et al. ............... 435/69.7 |
| 6,756,035 | B2 | 6/2004 | Qin et al. |
| 6,770,729 | B2 | 8/2004 | Van Antwerp |
| 2003/0096260 | A1 * | 5/2003 | Miao et al. ............... 435/6 |
| 2004/0243225 | A1 | 12/2004 | Ragheb et al. |

FOREIGN PATENT DOCUMENTS

| GB | 2276169 | 9/1994 |
|---|---|---|
| WO | WO 90/11092 | 10/1990 |
| WO | WO 90/13332 | 11/1990 |
| WO | WO 91/12779 | 9/1991 |
| WO | WO 91/17271 | 11/1991 |
| WO | WO 91/18980 | 12/1991 |
| WO | WO 92/01047 | 1/1992 |
| WO | WO 93/06121 | 4/1993 |
| WO | WO 93/17706 | 9/1993 |
| WO | WO 93/24640 | 12/1993 |
| WO | WO 94/08051 | 4/1994 |
| WO | WO 94/20142 | 9/1994 |
| WO | WO 95/12608 | 5/1995 |
| WO | WO 95/30642 | 11/1995 |
| WO | WO 95/35503 | 12/1995 |
| WO | WO 98/04554 | 2/1998 |

OTHER PUBLICATIONS

Al-Obeidi (1998), *Mol. Biotechnol.* 9:205-223.
Aoyama, Y. et al. (2001), *Bioorg. Med. Chem. Lett.* 11:1691-4.
Amour, A., et al. (1998), *J. Pharm. Pharmacol.* 50:593-600.
Berger, M.S. et al (1993), *DNA Cell Biol* 12:839-847.
Bao, L., et al. (1992), *Genomics* 13:437-40.
Berman et al. (1988), *Immunol. Invest.* 17: 625-677.
Baici, A. (1993), *Biochem. Pharmacol.* 46:1545-9.
Bae, Y.-S. et al. (2004) *J Immunol.* 173: 607-614.
Beusen, D. (1995), *Biopolymers* 36:181-200.
Banerjee, A. (1996), *Biopolymers* 39:769-777.
Berkhout, T.A. et al. (2000), *Biochem Pharmacol* 59:591-6.
Coligan (1991), *Current Protocols In Immunology*, Wiley/Greene, NY.
Cooley, J. (2001), *Biochemistry* 40:15762-70.
Christopherson, K.W., II, et al (2002), *J Immunol* 169:7000-7008.
Crump, M.P. et al (1997), *EMBO J* 16:6996-7007.
Cui, P. et al. (2001), *J Leukoc Biol* 70:306-312.
Chertov, O. et al. (1997), *J Exp Med* 186:739-747.
Durstin, M., et al. (1994), *Biochem Biophys Res Commun* 201:174-9.
Dolle and Nelson (1999), *J. Combinatorial Chemistry* 1:235-282.
Delgado, M.B. et al (2001), *Eur J Immunol* 31:699-707.
Ehrlich et al. (1980), Biochem 19:4091-4096.
Escher, S.E., et al. (2004), *J. Pept. Res.* 63:36-47.
Goding (1986), *Monoclonal Antibodies: Principles And Practice (2d ed.)*, Academic Press, New York, NY.
Graham et al. (1977), *J. Gen. Virol.* 36:59-72.
Gütschow, M. et al. (2002), *Arch. Biochem. Biophys.* 402:180-191.
Gilman et al. (1941), (Eds) *Organic Syntheses Collective Volumes*, John Wiley & Sons, Inc., NY.
Grimshaw, M.J. et al. (2002), *Eur J Immunol* 32:2393-2400.
Hayashi, Y. et al. (2000), *Bioorg. Med. Chem. Lett.* 10:199-201.

(Continued)

Primary Examiner—Jon P Weber
Assistant Examiner—Kailash C Srivastava
(74) Attorney, Agent, or Firm—Brinks Hofer Gilson & Lione

(57) ABSTRACT

Truncated chemokines lacking an N-terminal region that activate CCR1 and/or FPRL1 and compositions containing the truncated chemokines are provided. Methods of identifying agents that modulate CCR1 and/or FPRL1 activity either by modulating the production of the truncated chemokines or the ability of the truncated chemokines to activate CCR1 and/or FPRL1 are also disclosed. Methods using the truncated chemokines to inhibit or activate CCR1 and/or FPRL1 mediated biological activities are also disclosed.

10 Claims, 25 Drawing Sheets

OTHER PUBLICATIONS

Huse et al. (1989), *Science* 246:1275-81.
Hogg, P.J., et al. (1993), *J. Biol. Chem.* 268:21811-8.
He, S. et al. (1997), *J Immunol* 159:6216-6225.
Hara, T. et al. (1995), *J Immunol* 155:5352-5358.
Hogaboam, C.M. et al. (1999), *J Immunol* 162:6071-6079.
Janusz, M.J. and Hare, M. (1994), *Int. J. Immunopharmacol.* 16:623-32.
Kavanaugh et al. (1991), *J. Immunol.*, 146:4149-4156.
Korkmaz, B. et al. (2004), *Am. J. Respir. Cell Mol. Biol.* 30:801-807.
Kohler, G. and Milstein, A. (1975), *Nature* 256:495-97.
Kettleborough, C.A. et al. (1991), *Protein Engineering* 4:773-783.
Kuang, R. et al (2000), *Bioorg. Med. Chem.* 8:1005-1016.
Levy, B.D. et al. (2002), *Nat Med* 8:1018-23.
Langer, R. (1990), *Science* 249:1527-1533.
Ludwig, A. et al (2002), *J Leukoc Biol* 72:183-191.
Macphee, C. H. et al. (1998), *J. Immunol.* 161:6273-6279.
McBride J.D., et al. (1999), *Eur. J. Biochem.* 266:403-412.
Masaki, H., et al. (2003), *Bioorg. Med. Chem. Lett.* 13:4085-8.
McQuibban, G.A. et al. (2000), *Science* 289:1202-1206.
McQuibban, G.A. et al. (2001), *J Biol Chem* 276:43503-43508.
McQuibban, G.A. et al (2002), *Blood* 100:1160-1167.
Mohamadzadeh, M. et al. (1996), *J Immunol* 156:3102-3106.
Neote, K. et al. (1993), *Cell* 72: 415-425.
Nagai, U. (1985), *Tet. Lett.* 26:647-650.
Oravecz, T. et al. (1997), *J Exp Med* 186:1865-1872.
Patel, V.P. et al. (1997), *J Exp Med* 185:1163-72.
Proost, P. et al (2001), *Blood* 98:3554-3561.
Poltorak, A.N. et al. (1995), *J Inflamm* 45:207-219.
Queen, et al. (1989), *Proc. Nat'l Acad. Sci. USA* 86:10029-10033.
Rajarathnam, K. et al (2001), *J Biol Chem* 276:4909-4916.
Raymond, W.W. et al. (2003), *J. Biol. Chem.* 278:34517-34524.
Rehault, S. (1999), *J. Biol. Chem.* 274:13810-13817.
Rand, M. et al. (1996), *Am. J. Pathol.* 148:855-864.
Ransohoff, R.M. et al. (1996), *Cytokine Growth Factor Rev.* 7:35-46.
Springer-Verlag, N.Y., (1994), *Protein Purification: Principles And Practice* ($3^{rd}$ Edition).
Shinguh, Y. et al. (1997), *Eur. J. Pharmacol.* 337:63-71.
Sabroe, I., et al. (2000), *J. Biol. Chem.* 275:25985-25992.
Spatola (1983), *Chemistry and Biochemistry of Amino Acids, Peptides and Proteins*, vol. 7, pp. 267-357, *Peptide Backbone Modifications*, Marcell Dekker, NY.
Smith, A.B. (1992), *J. Amer. Chem. Soc.* 114:10672-10674.
Struyf, S. et al (1998), *Eur J Immunol* 28:1262-1271.
Shimizu, T. et al. (2002), *Arthritis Rheum* 46:2330-2338.
Tomimori, Y. et al. (2002), *Biochem Pharmacol* 64:1187.
Tani, K. et al. (2000), *Am J Respir Crit Care Med* 161:1636-1642.
Ulmer, J. et al. (1993), *Science* 259:1745-1749.
Vicentini, C.B. et al. (2001), *J. Enzyme Inhib.* 16:15-34.
Vagnoni, L.M. et al. (2001), *Bioorg. Med. Chem.* 9:637-45.
Wells, A. et al. (1985), *Gene* 34:315-323.
Winnacker, E.L. (1987), *From Genes To Clones* VCH Publishers, N.Y., N.Y.
Ward, E.S. et al. (1989), *Nature* 341:544-46.
Wieczorek, M. et al. (1999), *Arch. Biochem. Biophys.* 367:193-201.
Weg, J.B. et al. (1993), *J. Exp. Med.* 177:561-566.

\* cited by examiner

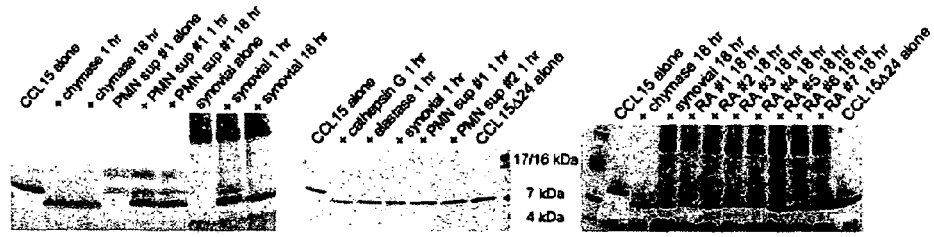
Figure 1A
```
QFINDAETELMMSKLPLENPVVLNSFHFAADCC... CCL15/MIP-1δ
                    VLNSFHFAADCC... + elastase
                    VLNSFHFAADCC... + PMN sup #1
                    VLNSFHFAADCC... + PMN sup #2
                         SFHFAADCC... + synovial
                              AADCC... + cathepsin G
                              AADCC... + chymase
```
Figure 1B
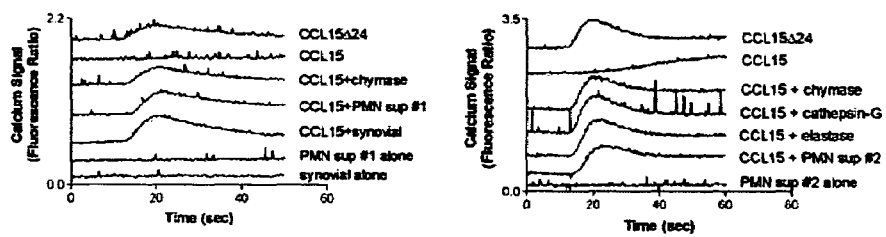
Figure 1C

Figure 3C

CCL6/C10 and N-Truncated Fragments

GLIQEMEKEDRRYNPPIIHQGFQDTSSDCCFSYATQIPCKRFIYYFPTSGGCIKPGIIFISRRGTQVCADPSDRRVQRCLSTLKQGPRSGNKVIA (SEQ ID NO:1)

FQDTSSDCCFSYATQIPCKRFIYYFPTSGGCIKPGIIFISRRGTQVCADPSDRRVQRCLSTLKQGPRSGNKVIA (SEQ ID NO:2)

QDTSSDCCFSYATQIPCKRFIYYFPTSGGCIKPGIIFISRRGTQVCADPSDRRVQRCLSTLKQGPRSGNKVIA (SEQ ID NO:3)

Figure 3D

CCL9/MIP-1γ and N-Truncated Fragments

QITHATETKEVQSSLKAQQGLEIEMFHMGFQDSSDCCLSYNSRIQCSRFIGYFPTSGGCTRPGIIFISKRGFQVCANPSDRRVQRCIERLEQNSQPRTYKQ (SEQ ID NO:4)

MGFQDSSDCCLSYNSRIQCSRFIGYFPTSGGCTRPGIIFISKRGFQVCANPSDRRVQRCIERLEQNSQPRTYKQ (SEQ ID NO:5)

GFQDSSDCCLSYNSRIQCSRFIGYFPTSGGCTRPGIIFISKRGFQVCANPSDRRVQRCIERLEQNSQPRTYKQ (SEQ ID NO:6)

FQDSSDCCLSYNSRIQCSRFIGYFPTSGGCTRPGIIFISKRGFQVCANPSDRRVQRCIERLEQNSQPRTYKQ (SEQ ID NO:7)

QDSSDCCLSYNSRIQCSRFIGYFPTSGGCTRPGIIFISKRGFQVCANPSDRRVQRCIERLEQNSQPRTYKQ (SEQ ID NO:8)

Figure 3E

CCL15/MIP-1δ and N-Truncated Fragments

```
QFINDAETELMMSKLPLENPVVLNSFHFAADCCTSYISQSIPCSLMKSYFETSSECSKPGVIFLTKKGRQVCAKPSGPGVQDCMKKLKPYSI  (SEQ ID NO:9)
              LPLENPVVLNSFHFAADCCTSYISQSIPCSLMKSYFETSSECSKPGVIFLTKKGRQVCAKPSGPGVQDCMKKLKPYSI  (SEQ ID NO:10)
                   NPVVLNSFHFAADCCTSYISQSIPCSLMKSYFETSSECSKPGVIFLTKKGRQVCAKPSGPGVQDCMKKLKPYSI  (SEQ ID NO:11)
                      VLNSFHFAADCCTSYISQSIPCSLMKSYFETSSECSKPGVIFLTKKGRQVCAKPSGPGVQDCMKKLKPYSI  (SEQ ID NO:12)
                        NSFHFAADCCTSYISQSIPCSLMKSYFETSSECSKPGVIFLTKKGRQVCAKPSGPGVQDCMKKLKPYSI  (SEQ ID NO:13)
                         SFHFAADCCTSYISQSIPCSLMKSYFETSSECSKPGVIFLTKKGRQVCAKPSGPGVQDCMKKLKPYSI  (SEQ ID NO:14)
                             AADCCTSYISQSIPCSLMKSYFETSSECSKPGVIFLTKKGRQVCAKPSGPGVQDCMKKLKPYSI  (SEQ ID NO:15)
```

Figure 3F

CCL23/CKβ8 and N-Truncated Fragments

```
RVTKDAETEFMMSKLPLENPVLLDRFHATSADCCISYTPRSIPCSLLESYFETNSECSKPGVIFLTKKGRRFCANPSDKQVQVCMRMLKLDTRIKTRKN  (SEQ ID NO:16)
              LPLENPVLLDRFHATSADCCISYTPRSIPCSLLESYFETNSECSKPGVIFLTKKGRRFCANPSDKQVQVCMRMLKLDTRIKTRKN  (SEQ ID NO:17)
                   NPVLLDRFHATSADCCISYTPRSIPCSLLESYFETNSECSKPGVIFLTKKGRRFCANPSDKQVQVCMRMLKLDTRIKTRKN  (SEQ ID NO:18)
                      LLDRFHATSADCCISYTPRSIPCSLLESYFETNSECSKPGVIFLTKKGRRFCANPSDKQVQVCMRMLKLDTRIKTRKN  (SEQ ID NO:19)
                         HATSADCCISYTPRSIPCSLLESYFETNSECSKPGVIFLTKKGRRFCANPSDKQVQVCMRMLKLDTRIKTRKN  (SEQ ID NO:20)
                            SADCCISYTPRSIPCSLLESYFETNSECSKPGVIFLTKKGRRFCANPSDKQVQVCMRMLKLDTRIKTRKN  (SEQ ID NO:21)
```

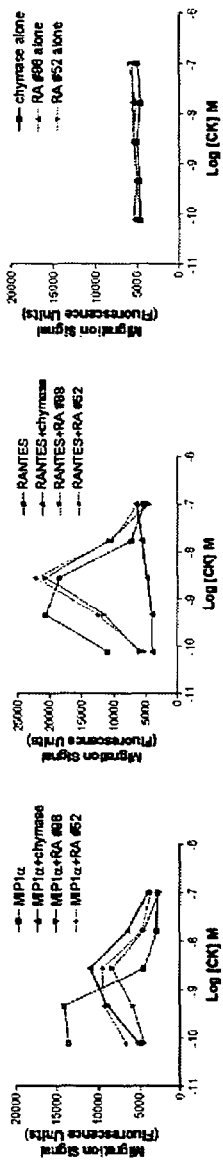
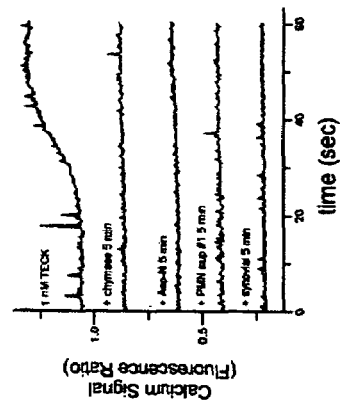
Figure 6A
Figure 6B
Figure 6C

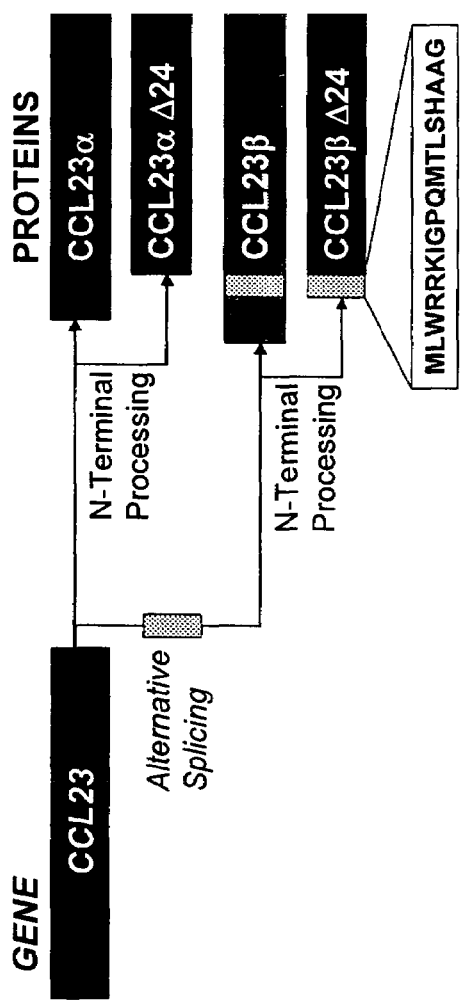
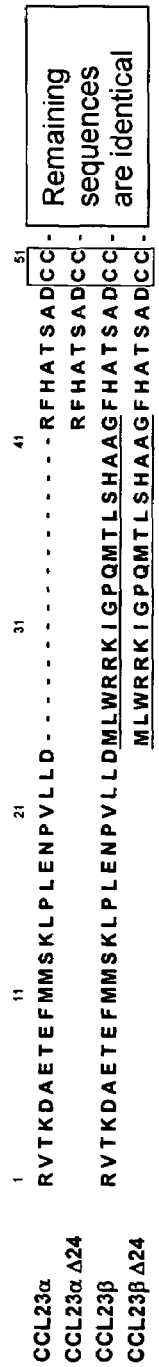
Figure 7A
Figure 7B

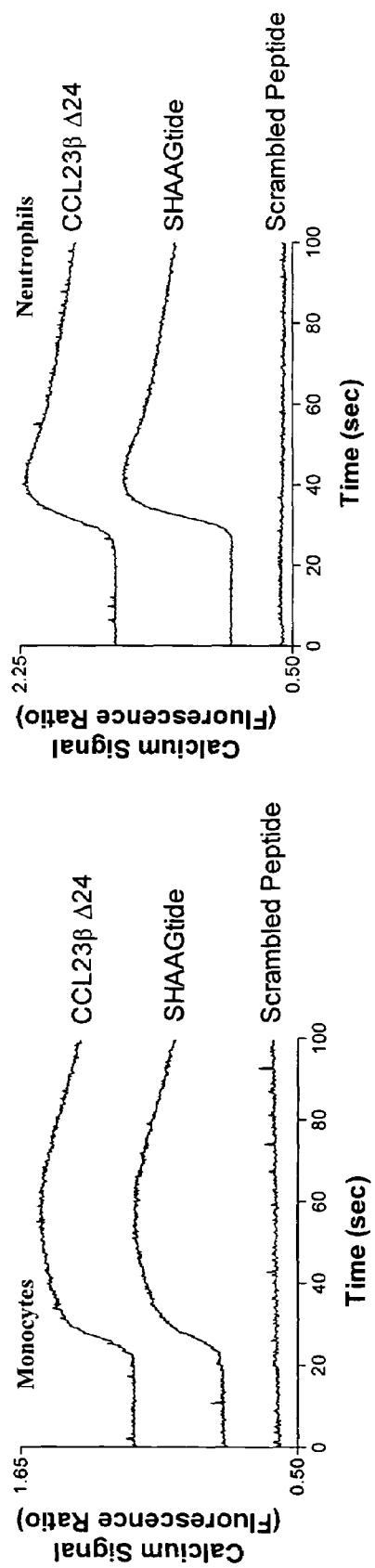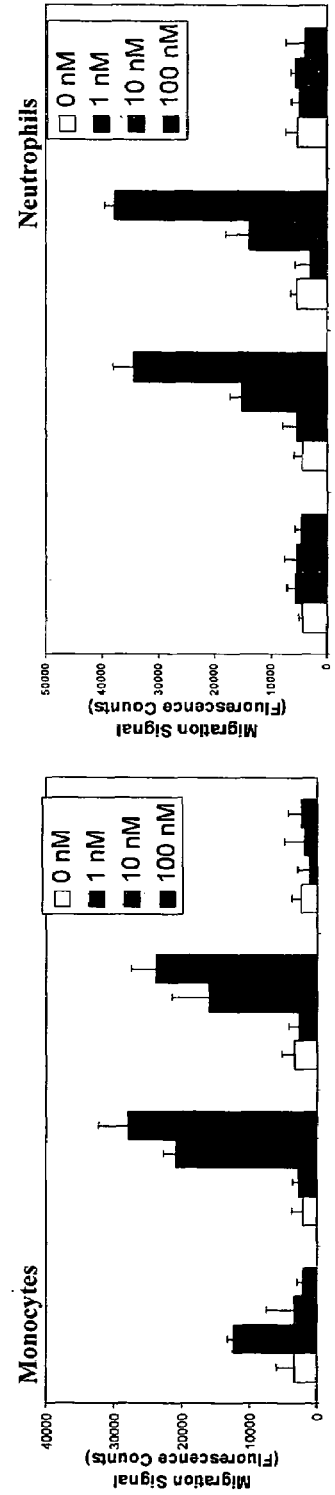
Figure 9A
Figure 9B
Figure 9C
Figure 9D

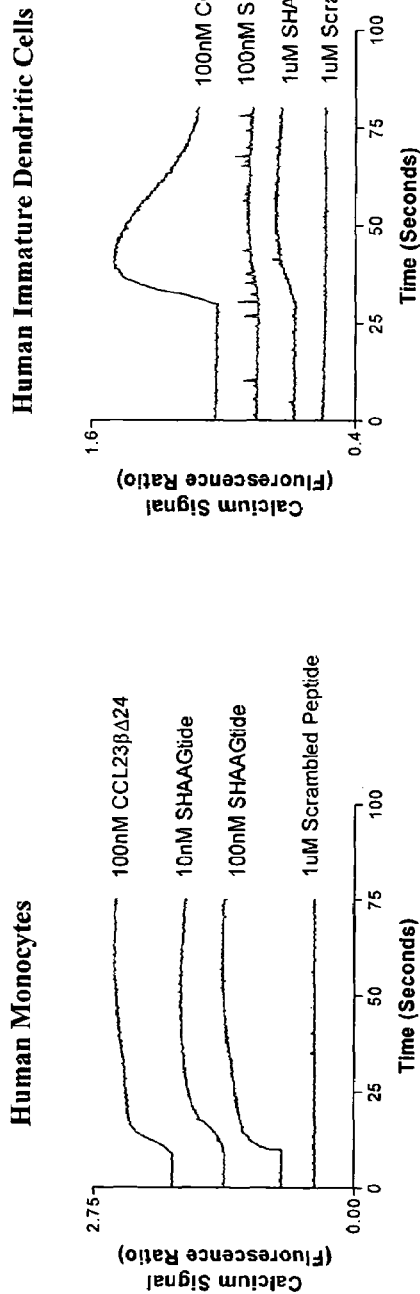
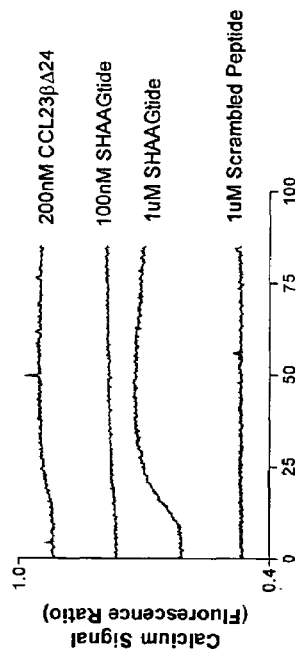
Figure 12A
Figure 12B
Figure 12C

| SEQ ID NOS: | PEPTIDES | EC50 in L1.2-FPRL1 (nM) |
|---|---|---|
| 48 | W K Y M V m | 0.2 |
| 22 | W K Y M V M | 3.5 |
| 27 | M L W R R K I G P Q M T L S H A A G | 19 |
| 24 | M L W R R K I G P Q M T L S H A A Y | 15 |
| 26 | M L W R R K I G P Q M T L S H | 18 |
| 29 | M L W R R K I G P Q M T | 65 |
| 33 | M L W R R K I G P Q M | 190 |
| 28 | L W R R K I G P Q M T L S H A A G | 210 |
| 23 | W R R K I G P Q M T L S H A A G | Inactive |
| 16 | R R K I G P Q M T L S H A A G | Inactive |
| 49 | CCL23α | Inactive |
| 50 | CCL23αΔ24 | Inactive |
| 45 | CCL23β | Inactive |
| | CCL23βΔ24 | 11 |

Figure 14

ENZYMATIC ACTIVITIES IN CHEMOKINE-MEDIATED INFLAMMATION

RELATED APPLICATIONS

The present patent document claims the benefit of the filing date under 35 U.S.C. §119(e) of Provisional U.S. Patent Application Ser. No. 60/598,959, filed Aug. 4, 2004, which is hereby incorporated by reference.

FEDERALLY SPONSORED RESEARCH OR DEVELOPMENT

This invention was made with Government support under Grant No. 1 U19 AI056690-01, awarded by NIAID. The Government may have certain rights in this invention.

BACKGROUND

Chemokines are a class of cytokines that play important roles in inflammatory responses, leukocyte trafficking, angiogenesis, and other biological processes related to the migration and activation of cells. As mediators of chemotaxis and inflammation, chemokines play roles in pathological conditions.

Known chemokines are typically assigned to one of four subfamilies based on the arrangement of cysteine motifs. In the so-called alpha-chemokines, for example, the first two of four cysteines (starting from the amino terminus) are separated by an intervening amino acid (i.e., having the motif C-X-C). The beta-chemokines are characterized by the absence of an intervening amino acid between first two cysteines (i.e., comprising the motif C-C). The smaller gamma- and delta-chemokine families are characterized by a single C residue or a pair of cysteines separated by three residues, respectively. For reviews on chemokines, see Ward et al., 1998, *Immunity* 9:1-11 and Baggiolini et al., 1998, *Nature* 392:565-568, and the references cited therein.

Chemokine activity may be mediated by receptors. For example, several seven-transmembrane-domain G protein-coupled receptors for C-C chemokines have been cloned: a C-C chemokine receptor-1 (CCR1) which recognizes MIP-1α, RANTES, MCP-2, MCP-3, and MIP-5 (Neote et al., 1993, *Cell,* 72:415-415); CCR2 which is a receptor for MCP1, 2, 3, 4 and 5; CCR3 which is a receptor for RANTES, MCP-2, 3, 4, MIP-5 and eotaxin; CCR5 which is a receptor for MIP-1α, MIP-1β and RANTES; CCR4 which is a receptor for MDC and TARC; CCR6 which is a receptor for LARC; and CCR7 which is a receptor for SLC and ELC (MIP-3β; reviewed in Sallusto et al., 1998, *Immunol. Today* 19:568 and Ward et al., 1998, *Immunity* 9:1-11).

CCR1 was the first chemokine receptor shown to interact with C-C (β) chemokines. In peripheral blood, all monocytes express high levels of CCR1. This receptor is also expressed on a small percentage of CD45RO+CD26+T cells, suggesting that it marks a subset of memory T cells. In contrast with chemokine receptors CCR5 and CXCR3, which are upregulated on activated T cells, CCR1 expression is decreased upon T cell activation. Neutrophils express low levels of CCR1 and show a weak response to MIP-1α in $Ca^{2+}$ mobilization assays. The expression of CCR1 on eosinophils varies among different individuals, ranging from >90% positive to completely negative. The expression pattern of CCR1 indicates that it is involved in a broad range of immunological activities, playing a major role in monocyte and eosinophil function, as well as in the function of a subset of T lymphocytes.

Chemokine activity may also be mediated by the unrelated chemotactic peptide receptors N-formyl peptide receptor (fMLP-R or FPR) and its homologues the 'orphan' receptors FPRL1 and FPRL2 (U.S. patent application Ser. No. 11,175,003, filed Jul. 5, 2005; Bao, L., et al. *Genomics* 13, 437-40 (1992); Murphy, P. M. et al., *J Biol Chem* 267, 7637-43 (1992); Durstin, M., et al., *Biochem Biophys Res Commun* 201, 174-9 (1994); Yang, D., et al, *J Immunol* 166, 4092-8 (2001)) (reviewed in Le, Y., Murphy, P. M. & Wang, J. M. Formyl-peptide receptors revisited. *Trends Immunol* 23, 541-8 (2002).

FPRL1 was originally cloned from a human phagocyte cDNA library and was characterized by nucleotide homology to FPR, although FPRL1 interacts very weakly with fMLP, the main ligand for FPR (Bao, L., et al., *Genomics* 13, 43740 (1992); Murphy, P. M. et al., *J Biol Chem* 267, 7637-43 (1992)). FPRL1 receptors induce chemotaxis, but can also activate myeloid cells and thereby stimulate their antigen-presenting properties (Le, Y., Murphy, P. M. & Wang, J. M. *Trends Immunol* 23, 541-8 (2002); Le, Y. et al., *J Neurosci* 21, RC123 (2001); and Le, Y., et al., *Cytokine Growth Factor Rev* 12, 91-105 (2001)). FPRL1 has also been reported to act as a functional lipoxin A4 receptor (Fiore, S. & Serhan, C. N., *Biochemistry* 34, 16678-86 (1995); Fiore, S., et al. *J Exp Med* 180, 253-60 (1994); Levy, B. D. et al. *Nat Med* 8, 1018-23 (2002); and Macphee, C. H. et al., *J Immunol* 161, 6273-9 (1998)), although there is still some debate over this activity. More recently, several groups studying FPRL1 have described a broad spectrum of low-affinity pathogen-related peptide and lipid ligands as well as several high affinity, but non-natural, synthetic peptide ligands (Le, Y., et al., *Trends Immunol* 23, 541-8 (2002); Le, Y. et al., *J Neurosci* 21, RC123 (2001); Le, Y., et al., *Cytokine Growth Factor Rev* 12, 91-105 (2001); Fiore, S. & Serhan, C. N. *Biochemistry* 34, 16678-86 (1995); Fiore, S., et al., *J Exp Med* 180, 253-60 (1994); Le, Y. et al., *J Immunol* 166, 1448-51 (2001); and Le, Y. et al., *J Immunol* 163, 6777-84 (1999)). The ability of FPRL1 to interact with this broad spectrum of pathogen-related ligands (Table 1, from Le, Y., et al., *Cytokine and Growth Factor Reviews* 12:91-105 (2001)) is unusual amongst G protein-coupled receptors (GPCRs) and suggests that FPRL1 may represent a novel type of pattern recognition receptors (PRR) with the potential for regulating innate immune responses to a number of viral and bacterial pathogens.

TABLE 1

Agonists and antagonists of formyl peptide receptors.

| LIGANDS | FPR | FPRL1 |
|---|---|---|
| Agonists | | |
| Bacterial peptide | | |
| fMLF | ++++ | + |
| H. pylori peptide, Hp(2-20) | – | +++ |
| HIV-1 Env domains: | | |
| T20/DP176 | ++++ | + |
| T21/DP107 | +++ | ++++ |
| N36 | – | +++ |
| F peptide | – | +++ |
| V3 peptide | – | +++ |
| Host-derived agonists: | | |
| LL-37 | – | ++++ |
| SAA | – | ++++ |
| Aβ$_{42}$ | ++ | ++++ |
| PrP106-126 | – | ++++ |
| Annexin I | +++ | +++ |
| Mitochondrial peptide | – | ++++ |

TABLE 1-continued

Agonists and antagonists of formyl peptide receptors.

| LIGANDS | FPR | FPRL1 |
|---|---|---|
| LXA4 | − | ++++ |
| Humanin | − | ++ |
| Temporin A | − | ++ |
| Peptide library derived agonists | +++ | ++++ |
| W peptide | − | ++++ |
| MMK-1 | + | +++ |
| Quinazolinone-C1 | | |
| Antagonists: | | |
| Boc-FLFLF | ++ | ? |
| CsH | +++ | − |
| Deoxycholoc acid (DCA) | +++ | +++ |
| Chenodeoxycholic acid (CDCA) | +++ | +++ |

Among the family of β chemokines, CCL6 (also referred to as C10 and MRP-1 in the art), CCL9 (also referred to as MIP-1γ and MRP-2 in the art), CCL15 (also referred to as MIP-1δ, HCC-2 and leukotactin-1 in the art) and CCL23 (also referred to as CKβ8 and MPIF-1 in the art)—possess an N-terminal domain upstream of the chemokine body. This domain contains 16-20 amino acids, including multiple basic and acidic residues, and is encoded by a separate exon (Berger, M. S. et al, 1993. *DNA Cell Biol* 12:839-847; Pardigol, A. et al, 1998. *Proc Natl Acad Sci USA* 95:6308-6313; Youn, B. S. et al, 1998. *Blood* 91:3118-3126; Macphee, et al. (1998) *J. Immunol.* 161:6273; and Youn, et al. (1997) *J. Immunol.* 159:5201). The N-terminal domains of the two human chemokines CCL15/MIP-1δ/HCC-2/leukotactin-1 and CCL23/CKβ8/MPIF-1 are nearly identical, while those of the two mouse chemokines CCL6/C10/MRP-1 and CCL9/MIP-1γ/MRP-2, are very different from each other and the two human chemokines. Human forms of CCL6 and CCL9, and murine forms of CCL15 and CCL23 have not been described. The four chemokines, CCL6, CCL9, CCL15, and CCL23 are relatively weak ligands for CCR1 and contain precisely-positioned $5^{th}$ and $6^{th}$ cysteine residues that appear to form a third disulfide bond (Pardigol, A. et al, 1998. *Proc Natl Acad Sci USA* 95:6308-6313; Rajarathnam, K. et al, 2001. *J Biol Chem* 276:4909-4916). For convenience, chemokines CCL6, CCL9, CCL15, and CCL23 are referred to herein as the "C6*" chemokine subfamily.

Interestingly, the CCL23 gene can give rise to 4 distinct protein products through alternative splicing of the third exon and N-terminal processing (FIG. 7A). The CCL23 cDNA, encoding a 99-residue protein (initially designated CKβ8, MPIF-1; here designated CCL23α; see review in Murphy, P. M. et al. International union of pharmacology. XXII. Nomenclature for chemokine receptors. *Pharmacol Rev* 52, 145-76 (2000)), was initially isolated from a library derived from human aortic endothelial cells (Patel, V. P. et al. *J Exp Med* 185, 1163-72 (1997)). An alternatively spliced form of the CCL23 cDNA, encoding a 116-residue protein termed CKβ8-1 (here designated CCL23β), was isolated from the myeloid cell line THP-1 (Youn, B. S. et al., *Blood* 91, 3118-26 (1998)). The CCL23β protein and its N-terminally truncated variants have also been found to be functional ligands for FPRL1, in addition to CCR1. See for example, U.S. patent application Ser. No. 11/175,003, entitled "Compositions Useful As Ligands For The Formyl Peptide Receptor Like 1 Receptor And Methods Of Use Thereof," filed Jul. 5, 2005, disclosure of which is incorporated by reference herein in its entirety.

Because of the important role chemokines play in a variety of inflammatory and other biological processes and because little is known about the nature of the interaction of CCR1 and FPRL1 with their cognate ligands, there is a need for these interactions, and their functional consequences, to be further characterized.

SUMMARY

The present inventors have identified a number of alternative ligands for the chemokine receptor CCR1 besides CCL3 and CCL5, which are typically considered the ligands for this receptor. Specifically, truncated forms of CCL6, CCL9, CCL15 and CCL23 in which the N-terminal domain has been removed have been found to have high affinity for CCR1. The inventors have also found that certain proteases, typically serine proteases, are responsible for producing these truncated chemokines. These findings have been used to develop a number of screening methods to identify inhibitors of CCR1, pharmaceutical compositions useful in the treatment of inflammatory diseases and conditions and pharmaceutical compositions useful in inducing immune responses.

Some screening methods, for instance, are designed to identify compounds that inhibit the proteases that form the activated truncated forms. Certain of these methods involve contacting a protease with a chemokine substrate in the presence of a test compound and then determining the activity of the protease in the presence of the test compound. The activity of the protease in the presence of the test compound is compared with the activity of the protease in the absence of the test compound. The test compound is identified as a potential inhibitor of CCR1 activity if the activity of the protease is inhibited in the presence of the test compound. Some screens are conducted using CCL6, CCL9, CCL15 or CCL23 as the substrate. Various proteases have been identified as cleaving these chemokines and can thus be used in the screening methods, including, for example, chymase, cathepsin G, and elastase. Agents in the initial screen can be further tested in a validation assay to confirm whether the inhibitor inhibits an activity of CCR1. These validation assays can be conducted with accepted models for various inflammatory diseases.

Other screening methods are designed to identify agents that modulate the ability of the activated CCL6, CCL9, CCL15 or CCL23 molecules (i.e., CCR1 ligand fragments) to bind and/or activate CCR1. Some methods of this type involve assaying for an activity of a CCR1 receptor in the presence of a CCR1 ligand fragment and a test agent and comparing the activity level in the presence of the test agent with the activity level in the absence of the test agent. A difference in the activity levels is an indication that the test agent is a modulator of the CCR1 activity. Various biological activities mediated by CCR1 can be assayed. Examples of such assays include, but are not limited to, assays for calcium mobilization, cell migration, and cell proliferation. Other methods detect the ability of the CCR1 ligand fragment to bind CCR1.

A variety of different inhibitors that inhibit the formation of CCR1 ligand fragments are provided. These inhibitors include CCR1 ligand analogues that include a modification that prevents cleavage of CCL6, CCL9, CCL15 or CCL23 in the region that results in removal of the N-terminal region. Specific examples of such inhibitors in this class include the following:

(a) a CCL6 analogue, wherein said CCL6 analogue comprises a CCL6 amino acid sequence in which there is a modification which inhibits cleavage between residues 13 and 27 by a serine protease;

(b) a CCL9 analogue, wherein said CCL9 analogue comprises a CCL9 amino acid sequence in which there is a modification which inhibits cleavage between residues 13 and 26 by a serine protease;

(c) a CCL15 analogue, wherein said CCL15 analogue comprises a CCL15 amino acid sequence in which there is a modification which inhibits cleavage between residues 17 and 32 by a serine protease; or (d) a CCL23 analogue, wherein said CCL23 analogue comprises a CCL23 amino acid sequence in which there is a modification which inhibits cleavage between residues 17 and 33 by a serine protease.

Pharmaceutical compositions of various types that are useful in treating inflammatory diseases or conditions associated with CCR1 activity are also provided. Some pharmaceutical compositions of this type include (1) an inhibitory agent that inhibits a serine protease that has the capacity to cleave an N-terminal fragment from CCL6, CCL9, CCL15 and/or CCL23 to generate a CCR1 ligand fragment that can activate CCR1, and (2) a pharmaceutically effective carrier. Certain pharmaceuticals within this class include the CCL6, CCL9, CCL15 and CCL23 analogues just described. The inhibitory agent can be of a variety of types including a small molecule and an antibody, for instance.

Other pharmaceutical compositions include an inhibitory agent that inhibits a CCR1 ligand fragment from binding to CCR1 and a pharmaceutically effective carrier. The inhibitory agent in some compositions is one that can inhibit the ability of a CCR1 ligand fragment having the amino acid sequence of SEQ ID NOs:2-3, 5-8, 10-15 or 17-21 to bind CCR1. These inhibitory agents can also be of various types including, but not limited to small molecules and antibodies.

Pharmaceutical compositions such as just described and as described elsewhere herein can be used to treat various inflammatory diseases. Some methods involve administering an effective amount of a pharmaceutical composition such as just described to an individual in need thereof. In some instances, a symptom associated with the inflammatory condition of the individual is monitored to determine the efficacy of the treatment.

Also provided are polypeptides that are related to the activated truncated forms of CCL6, CCL9, CCL15 and CCL23. Some polypeptides of this general type include isolated polypeptide fragments of CCL6 (SEQ ID NO:1) that have at least 90% sequence identity to SEQ ID NO:2 and can bind CCR1. Other polypeptides are isolated polypeptide fragments of CCL9 (SEQ ID NO:4) that have at least 90% sequence identity to SEQ ID NO:5 and can bind CCR1. Still other polypeptides are isolated polypeptide fragments of CCL15 (SEQ ID NO:9) that have at least 90% sequence identity to SEQ ID NO:10 and can bind CCR1. And still other polypeptides are isolated polypeptide fragments of CCL23 (SEQ ID NO:16) that have at least 90% sequence identity to SEQ ID NO:17 and can bind CCR1.

Pharmaceutical compositions and methods for inducting an immune response are provided. Pharmaceutical compositions of this type typically include a CCR1 ligand fragment as described herein and a pharmaceutically acceptable carrier. These compositions can be used to induce an immune response to an antigen in a subject. In some methods, an antigen is administered with the composition.

In another embodiment, the invention is a method for identifying an inhibitor of FPRL1 activity, comprising: (a) contacting protease with a chemokine substrate in the presence of a test compound; (b) determining the activity of the protease in the presence of the test compound; (c) comparing the activity of the protease in the presence of the test compound with the activity of the protease in the absence of the test compound; (d) identifying the test compound as a potential inhibitor of FPRL1 activity if the activity of the protease is inhibited in the presence of the test compound. The preferred substrate may be CCL23β. The protease may be selected from the group consisting of chymase, cathepsin G, and elastase. The method may further comprise conducting an assay of FPR1 activity with the inhibitor identified in step (d) to determine whether the inhibitor inhibits an activity of FPRL1.

In another embodiment, the invention is a method for screening for a modulator of FPRL1 activity, the method comprising assaying for an activity of an FPRL1 receptor in the presence of an FPRL1 ligand fragment and a test agent and comparing the activity level in the presence of the test agent with the activity level in the absence of the test agent, wherein a difference in the activity levels is an indication that the test agent is a modulator of the FPRL1 activity. The FPRL1 activity is may be binding between the FPRL1 receptor and the FPRL1 ligand fragment. The FPRL1 activity may be a biological activity selected from the group consisting of calcium mobilization, cell migration, and cell proliferation.

In another embodiment, the invention is a pharmaceutical composition comprising (i) an inhibitory agent that inhibits a serine protease having capacity to cleave an N-terminal fragment from CCL23β to generate an FPRL1 ligand fragment that can activate FPRL1, and (2) a pharmaceutically effective carrier.

In yet another embodiment, the invention is a pharmaceutical composition comprising an inhibitory agent that inhibits an FPRL1 ligand fragment from binding to FPRL1 and a pharmaceutically effective carrier.

In yet another embodiment, the invention is a medical device comprising the pharmaceutical composition of this invention.

In yet another embodiment, the invention is a method of treating an inflammatory condition correlated with FPRL1 activity. The method comprises administering an effective amount of a pharmaceutical composition of this invention to an individual in need thereof. The method further comprises monitoring a symptom associated with the inflammatory condition of the individual to determine the efficacy of the treatment

BRIEF DESCRIPTION OF THE DRAWINGS

FIG. 6. Pro-inflammatory proteases and fluids do not activate the non-C6* chemokines CCL3/MIP-1α, CCL5/RANTES or CCL25/TECK. Each chemokine was treated for varying times with selected proteases and fluids described in the legend to FIG. 1. A, analysis by SDS-PAGE. Portions of the digestions were subjected to SDS-PAGE, with subsequent Coomassie staining of the gels. B, chemotaxis assay. THP-1 cells were exposed to titrations of the CCL3/MIP-1α and CCL5/RANTES digestions for 2 hr, after which the migrated cells were solubilized and quantified by DNA content. C, calcium mobilization assay. Molt4 cells were loaded with a calcium-sensitive fluorescent dye, then exposed to the CCL25/TECK digestions at 1 nM and analyzed for fluorescence over time.

Figure 1D:
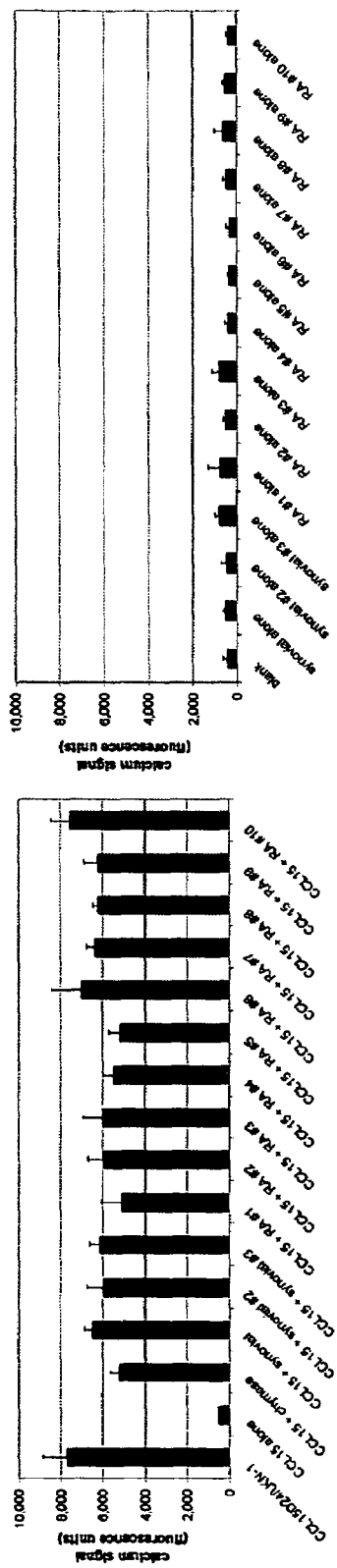
FIG. 1. Pro-inflammatory proteases and fluids digest and activate the human C6* chemokine CCL15/MIP-1δ. CCL15/MIP-1δ was incubated for 1 or 18 hr with recombinant mast cell chymase, purified neutrophil cathepsin G, purified neutrophil elastase, activated neutrophil-conditioned media from 2 donors ("PMN sup #1" and "PMN sup #2"), synovial fluids from 3 patients with sports-related knee injuries ("synovial", "synovial #2" & "synovial #3") and synovial fluids from 10 patients with rheumatoid arthritis ("RA#1" to "RA#10"). A, analysis by SDS-PAGE. Portions of the digestions were subjected to SDS-PAGE, then the gels (left and right panels) or a PVDF filter after electroblotting (middle panel) was stained with Coomassie Blue. Digestions lacking chemokine ("PMN sup alone", "synovial alone"—same dilutions as the digestions containing chemokine) and recombinant CCL15Δ24/LKN-1 are shown for comparison. B, N-terminal sequence analysis. N-terminal sequences of some of the truncated CCL15/MIP-1δ forms were determined by N-terminal Edman sequencing after SDS-PAGE and electroblotting. C, D, calcium mobilization assay. Murine L1.2 cells expressing human CCR1 were loaded with a calcium-sensitive fluorescent dye, then treated with a portion of the digestions and analyzed for fluorescence over time. In D, each trace's peak level of fluorescence is plotted. Digestions lacking chemokine (same dilutions as the digestions containing chemokine) and recombinant CCL15Δ24/LKN-1 (2.5 or 40 nM) are shown for comparison. E, chemotaxis assay. Dilutions of CCL15/MIP-1δ, CCL15Δ24/LKN-1 and either 3 of the CCL15/MIP-1δ digestions (left panel) or CCL3/MIP-1α and CCL5/RANTES (right panel) were exposed to THP-1 cells for 2 hr, after which the migrated cells were solubilized and quantified by DNA content.

MIP1α in the presence of increasing concentrations of CCL23 protein or unlabeled homologous CCL3/MIP-1α competitor. The $IC_{50}$ values derived from non-linear curve fitting are shown in the adjoining box. Binding experiments were confirmed in 3 separate experiments with essentially identical findings.

FIG. 8 demonstrates receptor signaling activities of the four CCL23 proteins. In these experiments, chemokine-induced calcium mobilization was used to as a measure of signaling and to probe receptor usage by cross-desensitization in freshly isolated human monocytes (A, C) and neutrophils (B, D). (A) In monocytes, CCL23β Δ24 is clearly the most efficacious calcium-mobilizing ligand of the four CCL23 proteins and produces an even greater response than CCL15 Δ24/leukotactin. (B) In neutrophils, which have very limited CCR1 functionality, CCL23β Δ24 is highly efficacious while the other CCL23 forms are inactive. (C) In monocytes, CCL15 Δ24/leukotactin completely desensitizes CCL23α, CCL23α Δ24 and CCL23β but not CCL23β Δ24, suggesting that the CCL23β Δ24 can signal through a receptor distinct from CCR1. (D) The inability of CCL15 Δ24/leukotactin to cross-desensitize CCL23β Δ24 in neutrophils suggests that CCL23β Δ24 can signal through a receptor distinct from CCR1. Cross-desensitization tests were performed by sequential stimulation with 2 chemokines as indicated by arrows. All chemokines were used at 100 nM. All experiments shown were repeated at least three times with similar results.

FIG. 9 demonstrates functional characterization of CCL23β Δ24 and SHAAGtide. (A, B) Receptor signaling assay in monocytes and neutrophils demonstrates that CCL23β Δ24 and SHAAGtide have identical activity. A scrambled version of SHAAGtide, used as a control peptide, has no activity. (C, D) CCL23β Δ24 and SHAAGtide are functional as chemoattractants in monocytes and neutrophils. Three concentrations of each species, as well as the scrambled peptide and the potent CCR1 agonist CCL23α Δ24, were analyzed by chemotaxis assay as described in the Methods. CCL23α Δ24 is inactive in neutrophils, confirming that CCR1 on these cells is poorly functional. Similar experiments, with similar results have been performed more than 5 times. (E) SHAAGtide recruits leukocytes in vivo. (Left panels) Micrographs showing hematoxylin & eosin staining of mouse skin reveal the presence of infiltrating leukocytes in the subcutis region of the dermis 6 hr after intradermal injection of 2 μg SHAAGtide but not after injection of the saline control. (Right panels) Immunohistochemical staining (red color) of the SHAAGtide-injected skin with an antibody specific for mouse neutrophils indicates that the recruited leukocytes include neutrophils. The lack of staining with the isotype control antibody indicates that the cells are indeed neutrophils, not cells that arbitrarily bind to rat IgG. Nuclei are stained blue with hematoxylin. The results shown are representative of those obtained in 6 mice.

FIG. 10. Dissection of receptor signaling and chemotactic activities through CCR1 and FPRL1 induced by CCL23β Δ24 and SHAAGtide. (A) CCL23α Δ24 and CCL23β Δ24, but not SHAAGtide, induce calcium mobilization in L1.2 cells transfected with human CCR1, indicating that the two CCL23 chemokines but not SHAAGtide can signal through CCR1. (B) CCL23β Δ24 and SHAAGtide, but not CCL23α Δ24, induce calcium mobilization in L1.2 cells transfected with human FPRL1, indicating that only SHAAGtide and its parent chemokine can signal through FPRL1. (C, D) Detailed calcium mobilization dose-response curves in the CCR1 and FPRL1 transfectants reveal the potencies of CCL23α Δ24 and CCL23β Δ24 for CCR1 signaling and the potencies of CCL23β Δ24 and SHAAGtide for FPRL1 signaling. (E, F) Chemotaxis dose-response curves in the CCR1 and FPRL1 transfectants reveal the potencies of CCL23α Δ24 and CCL23β Δ24 for CCR1-mediated chemotaxis and the potencies of CCL23β Δ24 and SHAAGtide for FPRL1-mediated chemotaxis.

FIG. 11. Analysis of the binding domains of CCL23β Δ24 and SHAAGtide. To assess CCR1 binding, competition with $^{125}$I-labeled MIP-1α ligand was performed on the L1.2-CCR1 transfectant or human monocytes (A, B). In comparison with the MIP-1α homologous competitor, CCL23β Δ24 exhibits moderate binding to CCR1 ($IC_{50}$ 20 nM for L1.2-CCR1, 4.5 nM for monocytes), while SHAAGtide does not bind CCR1. To assess FPRL1 binding, competition with $^{125}$I-labeled WKYMVm ligand was performed on the L1.2-FPRL1 transfectant or human monocytes (C, D). In comparison with the WKMVM homologous competitor, CCL23β Δ24 and SHAAGtide exhibited similar affinities for FPRL1.

FIG. 12. SHAAGtide-induced receptor signaling in human monocyte-derived dendritic cells. (A) In monocytes, both CCL23βΔ24 and SHAAGtide induce robust calcium responses. (B) In immature DC derived from the monocytes, SHAAGtide induces a small calcium response, indicating that FPRL1 has been down-regulated. CCL23β Δ24 induces a robust calcium response, presumably through CCR1. (C) In mature DC derived from the immature DC, both CCL23βΔ24 and SHAAGtide induce small calcium responses, indicating that FPR1 is expressed at low levels and that CCR1 has been down-regulated. All experiments shown were repeated at least three times with similar results.

FIG. 13. CCL23β protein processing and receptor signaling activity of cleavage products. (A) Cleavage of CCL23β Δ24 and a CCL23β-derived substrate peptide by supernatants collected from cultured neutrophils or recombinant human mast cell chymase. (A) Full length CCL23β Δ24 was digested with supernatant from activated neutrophils ("act. PMN sup") or with mast cell chymase, then the cleavage products were analyzed by SDS-PAGE and Coomassie staining. Control lanes show the 12 kD band of CCL23β alone (digested in the absence of proteases), a ~9 kD band of CCL23β Δ24 alone and a ~2 kD band of SHAAGtide alone. Both the neutrophil supernatant and chymase process CCL23β into several fragments, the smallest of which is similar in size to SHAAGtide. (B) A 42-residue peptide consisting of the CCL23β N-terminal and SHAAGtide domains was incubated for either 10 or 60 minutes with supernatants collected from resting ("PMN sup") or activated PMN ("Act. PMN sup"). The activated neutrophil supernatant was more efficient, digesting all of the 1-42 substrate peptide within 10 minutes. Control lanes show the ~4 kD band of 1-42 peptide alone, a ~2 kD band of SHAAGtide alone and the activated neutrophil supernatant alone (i.e. a digestion without substrate peptide). (C) Receptor signaling activity of CCL23β cleavage products in L1.2-FPRL1 cells. CCL23β was able to signal through CCR1 only after digestion with either the neutrophil supernatant or chymase. Control traces show pure SHAAGtide alone (10 nM) and the activated neutrophil supernatant alone. (D) The receptor-signaling activity of the CCL23β 1-42 peptide after digestion with the activated neutrophil supernatant can be blocked by an FPRL1-specific small molecule antagonist, CCX033. CCX033 inhibition was performed by adding 2 μM compound to the L1.2-FPRL1 cells 20 seconds prior to adding either SHAAGtide or the 1-42 digest. (E) A receptor signaling analysis of CCL23β 1-42 digests demonstrates that the neutrophil supernatants, chymase and Asp-N endopeptidase, but not chymotrypsin, activates FPRL1 signaling in L1.2-FPRL1 cells. However, digestion of the 1-42 peptide with a mixture of Asp-N and chymotrypsin did not activate the FPRL1 signaling. Peptide substrates were used at 100 nM.

FIG. 14. Illustration of SHAAGtide mapping.

DETAILED DESCRIPTION OF THE DRAWINGS AND THE PRESENTLY PREFERRED EMBODIMENTS

I. Definitions

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

The term "polypeptide" is used interchangeably herein with the term "protein," and refers to a polymer composed of amino acid residues linked by amide linkages, including synthetic, naturally-occurring and non-naturally occurring analogs thereof (amino acids and linkages). The terms do not refer to a specific length of the product. Thus, "peptides," "oligopeptides," and "proteins" are included within the definition of polypeptide. The terms include post-translational modifications of the polypeptide, for example, glycosylations, acetylations, phosphorylations and the like.

As used herein, references to specific proteins (e.g., CCL6, CCL9, CCL15, CCL23, CCL23β, CCR1 or FPRL1) refers to a polypeptide having a native amino acid sequence, as well as variants and modified forms regardless of origin or mode of preparation. A protein that has a native amino acid sequence is a protein having the same amino acid sequence as obtained from nature (e.g., a naturally occurring chemokine, such as a naturally occurring CCL6, CCL9, CCL15, or CCL 23). Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms, such as CCL23β), naturally occurring allelic variants and forms including postranslational modifications. A native sequence protein includes proteins following post-translational modifications such as glycosylation of certain amino acid residues.

Variants refer to proteins that are functional equivalents to a native sequence protein that have similar amino acid sequences and retain, to some extent, one or more activities of the native protein. Variants also include fragments that retain activity. Representative activities of the chemokines CCL6, CCL9, CCL15, CCL23, and CCL23β, include, but are not limited to, ability to bind and/or activate CCR1 and/or FPRL1. Activities of CCR1 include, but are not limited to, ability to bind cognate ligands such as CCL6, CCL9, CCL15 and CCL23, the ability to promote calcium mobilization, cell migration, and cell proliferation. Activities of FPRL1 include, but are not limited to, the ability to interact with CCL23β or a broad spectrum of pathogen-related ligands to regulate innate immune responses to a number of viral and bacterial pathogens.

Variants also include proteins that are substantially identical (see below) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein (see, e.g., Creighton (1984) Proteins, W.H. Freeman and Company). In the case of substitutions, the amino acid replacing another amino acid usually has similar structural and/or chemical properties. Insertions and deletions are typically in the range of 1 to 5 amino acids, although depending upon the location of the insertion, more amino acids can be inserted or removed. The variations can be made using methods known in the art such as site-directed mutagenesis (Carter, et al. (1986) Nucl. Acids Res. 13:4331; Zoller et al. (1987) Nucl. Acids Res. 10:6487), cassette mutagenesis (Wells et al. (1985) Gene 34:315), restriction selection mutagenesis (Wells, et al. (1986) Philos. Trans. R. Soc. London SerA 317:415), and PCR mutagenesis (Sambrook et al., Molecular Cloning: A Laboratory Manual, 3rd edition, Cold Spring Harbor Press, N.Y., (2001)).

Modified forms of a protein generally refer to proteins in which one or more amino acids of a native sequence have been altered to a non-naturally occurring amino acid residue. Such modifications can occur during or after translation and include, but are not limited to, phosphorylation, glycosylation, cross-linking, acylation and proteolytic cleavage.

Thus, references herein to chemokines such as CCL6, CCL9, CCL15, CCL23, and CCL23β include full length native forms, as well as variant and modified forms as just described. References to these proteins also include fusion proteins in which a segment from the chemokine that retains an activity of the chemokine is fused, for example, to another polypeptide (e.g., a polypeptide tag). Full-length CCL6, CCL9, CCL15, CCL23, CCL23β as used herein refers to the sequence of the chemokine once the signal sequence has been removed. Exemplary full length natural sequences of CCL6, CCL9, CCL15, CCL23, and CCL23β are as follows: CCL6 (SEQ ID NO:1; see also GenBank Accession No. AK002697); CCL9 (SEQ ID NO:4; see also GenBank Accession No. AF128195); CCL15 (SEQ ID NO:9; see also GenBank Accession No. NM_004167); CCL23 (SEQ ID NO:16, see also GenBank Accession No. NM_005064); and CCL23β (SEQ ID NO: 47).

"CCR1" (C-C chemokine receptor-1) as used herein refers to naturally occurring CCR1 proteins and variants and modified forms thereof. The term also refers to fusion proteins in which a domain from CCR1 that retains at least one CCR1 activity is fused, for example, to another polypeptide (e.g., a polypeptide tag such as are conventional in the art). The CCR1 can be from any source, but typically is a mammalian (e.g., human and non-human primate) CCR1, particularly a human CCR1. CCR1 can be from various mammalian sources (e.g., mouse, rat, humans, non-human primates). GenBank Accession No. NM_001295 provides an exemplary sequence for a naturally occurring human CCR1.

"CCR1 activity" as used herein refers broadly to any biological activity associated with CCR1. Thus, the term includes the specific binding of a ligand to CCR1. The term also refers to various signal transducing activities of the receptor including, for example, its ability to trigger calcium mobilization, promote chemotaxis, and cell proliferation.

Thus, the term "activate CCR1" and other related terms refers to a process whereby one or more activities of CCR1 are promoted or induced.

"FPRL1" as used herein refers to a receptor belonging to the N-formyl peptide receptor (FPR) family of receptors referred to as "FPR class" or "FPR members", which also includes FPRL2 (Le et al., 2001). The FPR class are G-protein-coupled receptors which have seven transmembrane domains. FPR members are typically found on human phagocytic cells but they have also been identified on hepatocytes, and cytokine stimulated epithelial cells. Many other cell types may have FPR members.

"FPRL1 activity" as used herein refers broadly to any biological activity associated with FPRL1. Thus, the term includes the specific binding of a ligand to FPRL1. The term also refers to various signal-transducing activities of the receptor including, for example, its ability to trigger calcium mobilization, promote chemotaxis, and cell proliferation. Thus, the term "activate FPRL1" and other related terms refers to a process whereby one or more activities of FPRL1 are promoted or induced.

A "fusion protein" or "fusion polypeptide" is a molecule in which two or more protein subunits are linked, typically covalently. The subunits can be directly linked or linked via a linking segment. An exemplary fusion protein is one in which a domain from a chemokine that retains a chemokine activity is linked to one or more purification tags (e.g., glutathione-S-transferase, His6, an epitope tag, and calmodulin binding protein). Another example is a CCR1 ligand fragment that is fused to one or more polypeptide tags. A further example is an FPRL1 ligand fragment that is fused to one or more polypeptide tags.

The term "conservative substitution," when describing a polypeptide, refers to a change in the amino acid composition of the polypeptide that does not substantially alter the activity of the polypeptide, i.e., substitution of amino acids with other amino acids having similar properties such that the substitutions of even critical amino acids does not substantially alter activity. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see also, Creighton, 1984, *Proteins*, W.H. Freeman and Company).

In addition to the above-defined conservative substitutions, other modification of amino acid residues can result in "conservatively modified variants." For example, one may regard all charged amino acids as substitutions for each other whether they are positive or negative. In addition, conservatively modified variants can also result from individual substitutions, deletions or additions which alter, add or delete a single amino acid or a small percentage of amino acids, e.g., often less than 5%, in an encoded sequence. Further, a conservatively modified variant can be made from a recombinant polypeptide by substituting a codon for an amino acid employed by the native or wild-type gene with a different codon for the same amino acid.

The terms "nucleic acid," "polynucleotide," and "oligonucleotide" are used herein to include a polymeric form of nucleotides of any length, including, but not limited to, ribonucleotides or deoxyribonucleotides. There is no intended distinction in length between these terms. Further, these terms refer only to the primary structure of the molecule. Thus, in certain embodiments these terms can include triple-, double- and single-stranded DNA, as well as triple-, double- and single-stranded RNA. They also include modifications, such as by methylation and/or by capping, and unmodified forms of the polynucleotide. More particularly, the terms "nucleic acid," "polynucleotide," and "oligonucleotide," include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, in certain embodiments these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels that are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine), those with intercalators (e.g., acridine, psoralen), those containing chelators (e.g., metals, radioactive metals, boron, oxidative metals), those containing alkylators, those with modified linkages (e.g., alpha anomeric nucleic acids), as well as unmodified forms of the polynucleotide or oligonucleotide. In particular, DNA is deoxyribonucleic acid.

The term "operably linked" refers to functional linkage between a nucleic acid expression control sequence (such as a promoter, signal sequence, or array of transcription factor binding sites) and a second polynucleotide, wherein the expression control sequence affects transcription and/or translation of the second polynucleotide.

A "heterologous sequence" or a "heterologous nucleic acid," as used herein, is one that originates from a source foreign to the particular host cell, or, if from the same source, is modified from its original form. Thus, a heterologous gene in a prokaryotic host cell includes a gene that, although being endogenous to the particular host cell, has been modified. Modification of the heterologous sequence can occur, e.g., by treating the DNA with a restriction enzyme to generate a DNA fragment that is capable of being operably linked to the promoter. Techniques such as site-directed mutagenesis are also useful for modifying a heterologous nucleic acid.

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "recombinant expression cassette" or simply an "expression cassette" is a nucleic acid construct, generated recombinantly or synthetically, that has control elements that are capable of affecting expression of a structural gene that is operably linked to the control elements in hosts compatible with such sequences. Expression cassettes include at least promoters and optionally, transcription termination signals. Typically, the recombinant expression cassette includes at least a nucleic acid to be transcribed (e.g., a nucleic acid encoding UCP-2) and a promoter. Additional factors necessary or helpful in effecting expression can also be used as described herein. For example, transcription termination signals, enhancers, and other nucleic acid sequences that influence gene expression, can also be included in an expression cassette.

As used herein, the term "substantial sequence identity," "substantially identical" and other like phrases refers to two or more sequences or subsequences that have at least 60% or 70%, preferably 80% or 85%, most preferably 90%, 95%, 98%, or 99% nucleotide or amino acid residue identity, when compared and aligned for maximum correspondence, as measured using one of the following sequence comparison algorithms or by visual inspection. Two sequences (amino acid or nucleotide) can be compared over their full-length (e.g., the length of the shorter of the two, if they are of substantially different lengths) or over a subsequence such as at least 50, 100, 200, 500 or 1000 contiguous nucleotides or at least 10, 20, 30, 40, 50 or 100 contiguous amino acid residues.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., Current Protocols In Molecular Biology, Greene Publishing and Wiley-Interscience, New York (supplemented through 1999). Each of these references and algorithms is incorporated by reference herein in its entirety. When using any of the aforementioned algorithms, the default parameters for "Window" length. gap penalty, etc., are used.

One example of algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the first polypeptide (e.g., a polypeptide encoded by the first nucleic acid) is immunologically cross reactive with the second polypeptide (e.g., a polypeptide encoded by the second nucleic acid). Thus, a polypeptide is typically substantially identical to a second polypeptide, for example, where the two peptides differ only by conservative substitutions.

Another indication that two nucleic acid sequences are substantially identical is that the two molecules hybridize to each other under stringent conditions. Substantial identity exists when the segments will hybridize under stringent hybridization conditions to a strand, or its complement, typically using a sequence of at least about 50 contiguous nucleotides derived from the probe nucleotide sequences.

"Stringent hybridization conditions" refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel, 1987, Methods In Enzymology, Vol. 152: Guide To Molecular Cloning Techniques, San Diego: Academic Press, Inc. and Sambrook et al., Molecular Cloning: A Laboratory Manual, 3rd edition, Cold Spring Harbor Press, N.Y., (2001). As indicated by standard references, a simple estimate of the Tm value may be calculated by the equation: Tm=81.5+0.41(% G+C), when a nucleic acid is in aqueous solution at 1 M NaCl (see e.g., Anderson and Young, "Quantitative Filter Hybridization" in Nucleic Acid Hybridization (1985)). Other references include more sophisticated computations which take structural as well as sequence characteristics into account for the calculation of Tm. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of formamide, dextran sulfate, polyethylene glycol). The effects of these factors are well known and are discussed in standard references in the art, see e.g., Sambrook et al., Molecular Cloning: A Laboratory Manual, 3rd edition, Cold Spring Harbor Press, N.Y., (2001), and Ausubel et al., Current Protocols In Molecular Biology, Greene Publishing and Wiley-Interscience, New York (supplemented through 1999). Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 60° C. for long probes (e.g., greater than 50 nucleotides). As noted, stringent conditions may also be achieved with the addition of destabilizing agents such as formamide, in which case lower temperatures may be employed.

The terms "substantially pure" or "isolated," when referring to proteins and polypeptides, denote those polypeptides that are separated from proteins or other contaminants with which they are naturally associated. A protein or polypeptide is considered substantially pure when that protein makes up greater than about 50% of the total protein content of the composition containing that protein, and typically, greater than about 60% of the total protein content. More typically, a substantially pure or isolated protein or polypeptide will make up at least 75%, more preferably, at least 90%, of the total protein. Preferably, the protein will make up greater than about 90%, and more preferably, greater than about 95% of the total protein in the composition.

The term "therapeutically effective amount" means the amount of the subject compound that will elicit the biological or medical response of a tissue, system, animal or human that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

A "control value" or simply "control" generally refers to a value (or range of values) against which an experimental or determined value is compared. Thus, in the case of a screening assay, the control value can be a value for a control reaction that is conducted under conditions that are identical those of a test assay, except that the control reaction is conducted in the absence of a candidate agent whereas the test assay is conducted in the presence of the candidate agent. The control value can also be a statistical value (e.g., an average or mean) determined for a plurality of control assays. The control assay(s) upon which the control value is determined can be conducted contemporaneously with the test or experimental assay or can be performed prior to the test assay. Thus, the control value can be based upon contemporaneous or historical controls.

A difference is typically considered to be "statistically significant" if in general terms an observed value differs from a control or background value by more than the level of experimental error. A difference can be considered "statistically significant" if the probability of the observed difference occurring by chance (the p-value) is less than some predetermined level. As used herein a "statistically significant difference" refers to a p-value that is <0.05, preferably <0.01 and most preferably <0.001.

The term "antibody" as used herein includes antibodies obtained from both polyclonal and monoclonal preparations, as well as the following: (i) hybrid (chimeric) antibody molecules (see, for example, Winter et al. (1991) Nature 349:293-299; and U.S. Pat. No. 4,816,567); (ii) F(ab')2 and F(ab) fragments; (iii) Fv molecules (noncovalent heterodimers, see, for example, Inbar et al. (1972) Proc. Natl. Acad. Sci. USA 69:2659-2662; and Ehrlich et al. (1980) Biochem 19:4091-4096); (iv) single-chain Fv molecules (sFv) (see, for example, Huston et al. (1988) Proc. Natl. Acad. Sci. USA 85:5879-5883); (v) dimeric and trimeric antibody fragment constructs; (vi) humanized antibody molecules (see, for example, Riechmann et al. (1988) Nature 332:323-327; Verhoeyan et al. (1988) Science 239:1534-1536; and U.K. Patent Publication No. GB 2,276,169, published 21 Sep. 1994); (vii) Mini-antibodies or minibodies (i.e., sFv polypeptide chains that include oligomerization domains at their C-termini, separated from the sFv by a hinge region; see, e.g., Pack et al. (1992) Biochem 31:1579-1584; Cumber et al. (1992) J. Immunology 149B:120-126); and, (vii) any functional fragments obtained from such molecules, wherein such fragments retain specific-binding properties of the parent antibody molecule.

The phrases "specifically binds" when referring to a protein, "specifically immunologically cross reactive with," or simply "specifically immunoreactive with" when referring to an antibody, refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule or ligand (e.g., an antibody) that specifically binds to a protein has an association constant of at least $10^3$ $M^{-1}$ or $10^4$ $M^{-1}$, sometimes $10^5$ $M^{-1}$ or $10^6$ $M^{-1}$, in other instances $10^6$ $M^{-1}$ or $10^7$ $M^{-1}$, preferably $10^8$ $M^{-1}$ to $10^9$ $M^{-1}$, and more preferably, about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

The term "detectably labeled" means that an agent (e.g., a probe) has been conjugated with a label that can be detected by physical, chemical, electromagnetic and other related analytical techniques. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

A "small organic molecule" or simply "small molecule" as used herein refers to a synthetic molecule that typically has a molecular weight of less than 1000 daltons, more typically 500 daltons or less. Such molecules can include, for example, sterols, amino acids, small nucleic acids, small peptides, aromatic compounds, heterocyclic compounds, benzodiazepines, oligomeric N-substituted glycines and oligocarbamates.

A "subject", "individual" or "patient" as used herein in the context of therapeutic and prophylactic treatment methods typically refers to a mammal, including primates (e.g., humans, apes, chimpanzee, gorilla) and non-human primates (e.g., mouse, rat, rabbit), but most typically refers to a human.

II. Overview

The present invention is premised, in part, on several findings by the current inventors regarding the identity of alternative ligands for the CCR1 and/or FPRL1 receptors and the mode by which these alternative ligands are formed.

The current inventors have found, for instance, that CCR1 has a number of alternative ligands besides CCL3/MIP-1α or CCL5/RANTES, which are considered to be the primary CCR1 ligands in inflammatory responses. It was found that in addition to CCL3 and CCL5 that CCL6/C10/MRP-1, CCL9/MIP-1γ/MRP-2, CCL15/MIP-1δ/HCC-2/leukotactin-1 and CCL23/CKβ8/MPIF-1 are also CCR1 ligands (the slashes in this sentence separate alternative names used in the art for these different chemokines). As noted in the background section, these four chemokines are unique among chemokines in possessing a separately-encoded N-terminal domain of 16-20 residues and two additional precisely-positioned cysteines which form a $3^{rd}$ disulfide bridge. Although the full length proteins are rather weak CCR1 agonists, it was found that the potency of these ligands can be increased up to 1000-fold by engineered or expression-associated N-terminal truncations.

The inventors also found, for example, that the CCL23 truncation variant, CCL23β Δ24, is involved in inflammatory reactions and innate immunity through its role as a functional ligand for the FPRL1. In addition, the inventors have discovered a portion of CCL23β, designated as SHAAGtide, and truncated and other variants of SHAAGtide that, along with CCL23β Δ24, are functional on cells that are known to express FPRL1. Functional SHAAGtides generate calcium flux upon receptor-ligand binding in leukocytes and attract monocytes, neutrophils, mature dendritic cells (mDCs), and immature dendritic cells (iDCs) (U.S. patent application Ser, No. 11,175,003, filed Jul. 5, 2005, and disclosure of which is incorporated by reference in its entirety).

Also, the current inventors have found, for instance, that chemokine ligand fragments may be bifunctional ligands for at least two different receptors. For example, the inventors showed that CCL23β Δ24 can bind to CCR1 and FPRL1.

Moreover, the current inventors also found that a number of pro-inflammatory proteases and certain human cell supernatants or physiological fluids are capable of effecting the N-terminal truncations, thereby resulting in significant increases in CCR1 and FPRL1 activity. Remarkably, most of the proteases and fluids removed the N-terminal domains from all five of the foregoing chemokines, but were relatively unable to cleave the truncated forms further. The truncated chemokines exhibited up to 1000-fold increases in CCR1-mediated signaling and chemotaxis activity and about 50-100-fold increases in FPRL1-mediated signaling and chemotaxis activity. In addition, N-terminally truncated CCL15 and CCL23, but not CCL3 or CCL5, were detected at relatively high levels in synovial fluids from rheumatoid arthritis patients. These results thus indicate that alternative CCR1 and FPRL1 ligands are converted into potent chemoattractants by proteases released during inflammatory responses in vivo.

These findings form the basis for a number of different inventive compositions and methods. For example, a number of classes of alternative CCR1 ligands, including CCR1 ligand fragments that are N-truncated forms of CCL6, CCL9, CCL15 and CCL23, are provided. Also, a number of classes of alternative FPRL1 ligands, including FPRL1 ligand fragments that are N-truncated forms of CCL23β, are provided. Nucleic acids encoding these CCR1 and/or FPRL1 ligand fragments, vectors containing the nucleic acids and cells containing such vectors are also disclosed. These alternative CCR1 and/or FPRL1 ligands can be formulated as part of a pharmaceutical composition, which can be used in various treatment methods in which it is desired to activate CCR1 and/or FPRL1 responses. Some pharmaceutical compositions including alternative CCR1 and/or FPRL1 ligands can be used to promote an immunological response to an antigen of interest.

Inhibitors of CCR1 and/or FPRL1 activity based upon the structure of the alternative CCR1 and/or FPRL1 ligands are also provided. Certain inhibitors, for instance, are proteins that mimic CCL6, CCL9, CCL15, CCL23, or CCL23β but are designed to resist cleavage at the normal cleavage site. Antibodies that selectively bind to the alternative CCR1 and/or FPRL1 ligands are also provided. These inhibitors and antibodies can be formulated as pharmaceutical compositions to treat a variety of physiological conditions (e.g., a variety of inflammatory responses) that are mediated by CCR1 and/or FPRL1.

A number of different screening methods are also provided. In general these methods are designed to identify agents that modulate the activity of CCR1 and/or FPRL1. One category of methods involves screening compounds to identify ones that can modulate the activity of the proteases that truncate CCL6, CCL9, CCL15, CCL23, and CCL23β, thereby modulating the activity of CCR1 and/or FPRL1 by modulating the production of the active forms of these ligands. Another category of screening methods are designed to determine the direct effect of various test agents on the biological activity of CCR1 and/or FPRL1 rather than identifying agents that exert their effect upstream of the receptor.

Various therapeutic and prophylactic methods are also provided. These methods can involve the administration of agents that inhibit the activity of a protease that forms the active N-terminal truncated forms of CCL6, CCL9, CCL15, CCL23, and CCL23β and/or that inhibit the ability of these active forms to bind CCR1 and/or FPRL1, thereby treating a variety of inflammatory diseases. Alternatively, agents that activate the activity of the protease and/or the ability of the N-truncated forms of the chemokines to bind CCR1 and/or FPRL1 can be used to treat diseases and conditions associated with immunosuppression. The N-truncated forms can also be used in combination with vaccines to promote an immune response to an antigen of choice.

III. CCR1 Alternative Ligands and CCR 1 Alternative Ligand Fragments

Figures 3A, 3B:
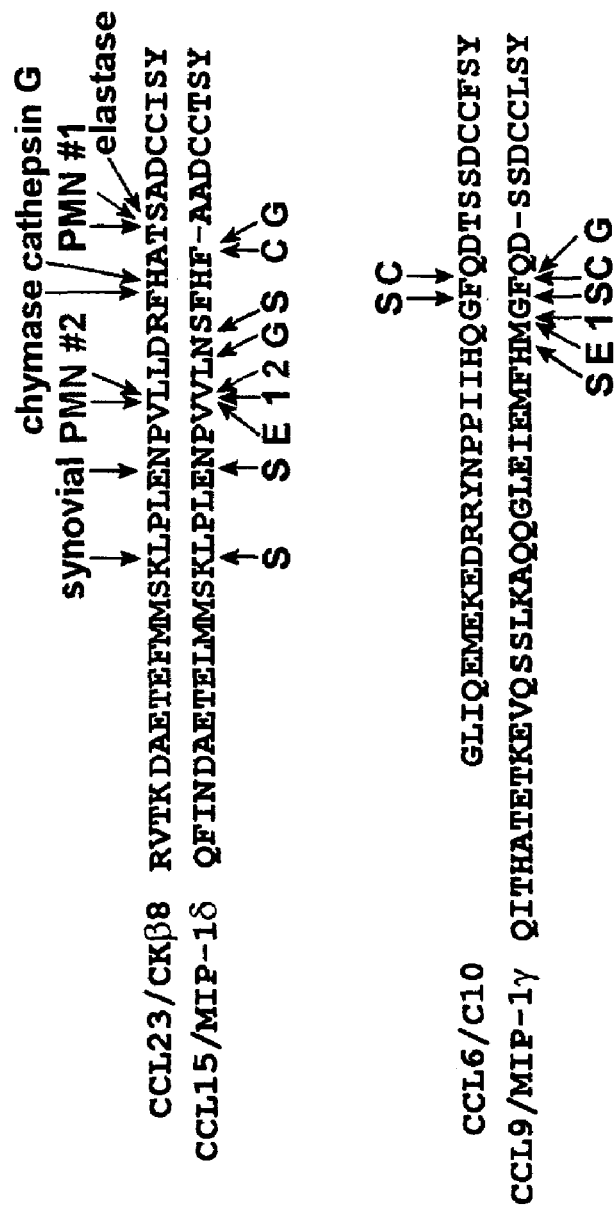
FIG. 3. Cleavage sites on CCL6, CCL9, CCL15 and CCL23 with the different inflammatory proteases and the sequences of the resulting fragments. A. Cleavage sites on CCL23 and CCL15. S=synovial fluid; E=purified neutrophil elastase; PMN #1 and PMN#2 (or simply 1 or 2)=activated neutrophil-conditioned media from donor 1 or donor 2; G=purified neutrophil cathepsin G; C=recombinant mast cell chymase. B. Cleavage sites on CCL5 and CCL9. C. Full-length sequence (without signal sequence) of CCL6 (SEQ ID NO:1) and two N-truncated polypeptides produced by incubation with synovial fluid (SEQ ID NO:2) and chymase (SEQ ID NO:3). D. Full-length sequence (without signal sequence) of CCL9 (SEQ ID NO:4) and the four different N-truncated polypeptides formed by incubation with different proteases: 1) synovial fluid (SEQ ID NO:5); 2) elastase or activated neutrophil-conditioned media (SEQ ID NO:6); 3) synovial fluid (SEQ ID NO:7); and 4) chymase or cathepsin G (SEQ ID NO:8). E. Full-length sequence (without signal sequence) of CCL15 (SEQ ID NO:9) and six different N-truncated polypeptides formed by incubation with different proteases: 1) synovial fluid (SEQ ID NOs:10); 2) synovial fluid (SEQ ID NO:11); 3) elastase or activated neutrophil-conditioned media (SEQ ID NO:12); 4) cathepsin G (SEQ ID NO:13); 5) synovial fluid (SEQ ID NO:14); and 6) chymase or cathepsin G (SEQ ID NO:15). F. Full-length sequence (without signal sequence) of CCL23 (SEQ ID NO:16) and the five different N-truncated polypeptides generated by incubation with different proteases: 1) synovial fluid (SEQ ID NO:17); 2) synovial fluid (SEQ ID NO:18); 3) activated neutrophil-conditioned media or elastase (SEQ ID NO:19); 4) chymase or cathepsin G (SEQ ID NO:20); and 5) synovial fluid or elastase (SEQ ID NO:21).

As alluded to above, the compositions and methods that are provided herein are based, in part, upon the finding that the exposure of CCL6, CCL9, CCL15 and CCL23 to recombinant mast cell chymase, purified neutrophil cathepsin G or elastase, activated neutrophil-conditioned media or synovial fluids from highly-inflamed tissues resulted in partial or complete removal of an inhibitory N-terminal domain from these chemokines. The resulting truncated forms were able to activate CCR1, including activating CCR1-mediated calcium mobilization and cell migration, to levels significantly higher than the full-length proteins. The sites at which these various proteases cleave CCL6, CCL9, CCL15 and CCL23 are shown in FIGS. 3A and 3B. The resulting N-truncated fragments are shown in FIGS. 3C-3F (see also SEQ ID NOs:2-3, 5-8, 10-15 and 17-21).

In addition, synovial fluids from rheumatoid arthritis patients and persons with knee injuries were found to contain N-terminally truncated CCL15 and CCL23 at concentrations more than sufficient to activate a biological response. In contrast, the traditional CCR1 ligands CCL3 and CCL5 were wholly or partially inactivated by the proteases and fluids. Moreover, CCL3 and CCL5 were detected in synovial fluids from only a subset of rheumatoid arthritis patients, at concentrations insufficient to activate a biological response.

A variety of CCR1 alternative ligands are thus provided that are distinct from CCL3 and CCL5, which are traditionally considered to be the ligands for CCR1. The term "CCR1 alternative ligands" in a broad sense thus refers to ligands other than CCL3 and CCL5 that specifically bind CCR1. The term thus includes full length CCL6, CCL9, CCL15 and CCL23, as well as variants and modified forms of these chemokine proteins, including the N-terminal truncated forms disclosed herein.

The term "CCR1 alternative ligands" encompasses "CCR1 ligand fragments", which refers to polypeptide fragments of CCR1 ligands in which an N-terminal region has been deleted to leave a fragment that can nonetheless bind and/or activate CCR1. Unless stated otherwise, references to the N-terminus of CCL6, CCL9, CCL15 and CCL23 are made with the assumption that the signal sequence from these chemokines has been removed. Thus, the "full-length" sequences of these chemokines actually correspond to the sequences once the signal sequence has been removed. The full-length amino acid sequences of CCL6, CCL9, CCL15 and CCL23 without the signal sequences correspond to SEQ ID NOs:1, 4, 9 and 16, respectively. The first amino acid in these sequences corresponds to the first amino acid of the mature protein once the signal sequence has been removed.

The phrase CCR1 alternative ligands includes, for instance, N-truncated fragments of naturally occurring, variant or modified forms of CCL6, CCL9, CCL15 and CCL23 proteins that can bind and/or activate CCR1 even though an N-terminal region has been deleted. These N-truncated fragments are typically at least 50, 60, 70, 80, 90, 100 or 110 amino acids in length. Generally at least 5-40, 10-30, or 15-25 (or any integer within these ranges) consecutive amino acids from the N-terminus of CCL6, CCL9, CCL15, CCL23 are deleted. Thus, some CCR1 ligand fragments are a truncated form of CCL6, CCL9, CCL15 or CCL23 in which 10, 12, 14, 16, 18, 20, 22, 24, 26, 28 or 30 consecutive amino acids from the N-terminus of the full length protein has been removed. CCR1 ligand fragments include N-terminal truncated forms of CCL6, CCL9, CCL15 and CCL23 in which a N-terminal region has been removed by incubation with a protease, particularly a pro-inflammatory protease such as a serine protease (e.g., chymase, cathepsin G, or elastase, or a composition obtained from a source containing pro-inflammatory proteases. Sources of inflammatory proteases include, but are not limited to, cell extracts from immune cells or cell media used to culture immune cells (e.g., neutrophils, activated leukocytes), and physiological fluids taken from inflammatory tissue (e.g., synovial fluid from individuals suffering from an inflammatory disease or condition, such as rheumatoid arthritis, knee injuries, and osteoarthritis).

One class of CCR1 ligand fragments have the following characteristics: 1) they are fragments of CCL6, CCL9, CCL15 or CCL23, 2) they have substantial sequence identity (e.g., at least 80%, 85%, 90% or 95% sequence identity) with CCL6, CCL9, CCL15 or CCL23, and 3) they can bind and/or activate CCR1. Because these proteins are fragments of CCL6, CCL9, CCL15 or CCL23, these fragments thus do not include the full-length sequence of CCL6, CCL9, CCL15 or CCL23 (i.e., SEQ ID NOs: 1, 4, 9 and 16, respectively).

Specific examples of CCR1 ligand fragments related to CCL6 are those that have substantial sequence identity with SEQ ID NO: 1, 2 or 3 and that can bind and/or activate CCR1. Other fragments related to CCL6 are truncated forms of CCL 6 in which 10-30 (e.g., 13-27) consecutive amino acids from the N-terminus of CCL6 (e.g., SEQ ID NO:1) are deleted but that can bind and/or activate CCR1. Specific fragments in this class include, but are not limited to, those having the sequence of SEQ ID NO:2 or 3. As shown in FIGS. 3B and 3C, these fragments can be generated by incubating CCL6 with synovial fluid from inflamed tissue and recombinant chymase, respectively.

CCR1 ligand fragments related to CCL9 include fragments that have substantial sequence identity with SEQ ID NO:4, 5, 6, 7, or 8 and that can bind and/or activate CCR1. Certain fragments are truncated forms of CCL9 in which 10-30 (e.g., 13-26) consecutive amino acids from the N-terminus of CCL9 (e.g., SEQ ID NO:4) are removed but the fragment nonetheless can bind and/or activate CCR1. Specific examples of CCR1 ligand fragments that are fragments of CCL9 include, but are not limited to, those having the amino acid sequence of SEQ ID NO:5, 6, 7 or 8. As illustrated in FIGS. 3B and 3D, the fragments corresponding to SEQ ID NOs:5-8 can be generated by incubating CCL9 with the following sources of enzyme: (a) SEQ ID NO:5—synovial fluid from inflamed tissue; (b) SEQ ID NO:6—purified elastase or activated neutrophil-conditioned media; (c) SEQ ID NO:7—synovial fluid from inflamed tissue; (d) SEQ ID NO:8—recombinant chymase and purified cathepsin G.

Examples of CCR1 ligand fragments related to CCL15 include fragments that have substantial sequence identity with SEQ ID NO:9, 10, 11, 12, 13, 14 or 15 and that can bind to and/or activate CCR1. Some fragments, for instance, include truncated forms of CCL15 in which 15-35 (e.g., 17-32) consecutive amino acids are deleted from the N-terminus of CCL15 (e.g., SEQ ID NO:9), with the fragments retaining the capacity to bind and/or activate CCR1. Specific examples of CCR1 ligand fragments that are fragments of CCL15 include, but are not limited to, fragments having the sequence of SEQ ID NO: 10, 11, 12, 13, 14 or 15. As depicted in FIGS. 3A and 3E, these fragments can be generated by incubating CCL 15 with the following indicated source of protease: (a) SEQ ID NOs:10 and 11—synovial fluid, (b) SEQ ID NO:12—purified elastase or activated neutrophils-conditioned media, (c) SEQ ID NO:13—purified cathepsin G, (d) SEQ ID NO:14—synovial fluid from inflamed tissue, and (e) SEQ ID NO:15—recombinant chymase and purified cathepsin G.

CCR1 ligand fragments based on the sequence of CCL23 include fragments that have substantial sequence identity with SEQ ID NO:16, 17, 18, 19, 20 or 21 and that can bind and/or activate CCR1. Exemplary fragments include truncated forms of CCL23 in which 15-35 (e.g., 17-33) consecutive amino acids are deleted from the N-terminus of CCL23 (e.g., SEQ ID NO: 16), with the fragments still able to bind to and/or activate CCR1. Specific examples of CCR1 ligand fragments that are fragments of CCL23 include, but are not limited to, fragments having the sequence of SEQ ID NO: 17, 18, 19, 20 or 21. FIGS. 3A and 3F demonstrate that these particular fragments can be produced by incubating CCL23 with the protease sources as follows: (a) SEQ ID NOs:17 and 18—synovial fluid from inflamed, (b) SEQ ID NO:19—activated neutrophils-conditioned media or purified elastase; (c) SEQ ID NO:20—recombinant chymase or purified cathepsin G; (d) SEQ ID NO:21—activated neutrophil-conditioned media or purified elastase.

Each of the foregoing specific fragments listed as SEQ ID NOs:2, 3, 5-8, 10-15 and 17-21 can include, for example, conservative substitutions and/or modifications. In some instances, these fragments lack or include an additional 1-5 amino acids at either the N-terminal or C-terminal end relative to the sequences as defined above.

The CCR1 ligand fragments can also be components of a fusion protein. One class of fusion proteins are those in which the CCR1 ligand fragment is fused to a short peptide tag. A number of tags can be used. Exemplary tags, include, but are not limited to glutathione-S-transferase, His6, an epitope tag, and calmodulin binding protein.

IV. FPRL1 Alternative Ligands and FPRL1 Alternative Ligand Fragments

As indicated above, the pro-inflammatory proteases, either purified or in supernatants of activated neutrophils or in human inflammatory fluids, removed the N-terminal domain from CCL23β, thereby dramatically activating its function on FPRL1. N-terminal sequencing analysis of the cleaved CCL23β fragments indicated that the neutrophil supernatants cleaved after Val[21], while chymase cleaved after Leu[23], producing fragments with 3 (neutrophil supernatants) or 1 (chymase) amino acids in front of the SHAAGtide domain (ML-WRRKIGPQMTLSHAAG). The proteases also cleaved CCL23β near the C-terminal end of the SHAAGtide domain, releasing SHAAGtides from the CCL23β protein.

A variety of FPRL1 alternative ligands are thus provided that are distinct from the ligands identified in Table 1, which are traditionally considered to be the ligands for FPRL1. The term "FPRL1 alternative ligands" in a broad sense thus refers to ligands other than those identified in Table 1 that specifically bind FPRL1. The term thus includes full length CCL23β, as well as variants and modified forms of the CCL23β chemokine protein, including N-terminally truncated CCL23β and internal fragments disclosed herein. These internal fragments of CCL23β disclosed herein are referred to as SHAAGtides. Table 2 shows the exemplary alternative ligands of FPRL1, namely SHAAGtide polypeptide sequence (SEQ ID NO:22) and the polypeptide sequences of certain SHAAGtide truncated variants and other variants (SEQ ID NOS: 23-33). Table 3 shows the SHAAGtide polynucleotide sequence (SEQ ID NO:34) and the polynucleotide sequences of SHAAGtide truncated variants and other variants (SEQ ID NOS:35-44). Table 4 shows the CCL23β polypeptide sequence (SEQ ID NO:45), and Table 5 shows the CCL23β polynucleotide sequence (SEQ ID NO:46)

The phrase FPRL1 alternative ligands includes, for instance, N-truncated fragments of naturally occurring, variant or modified forms of CCL23β proteins that can bind and/or activate FPRL1 even though an N-terminal region has been deleted. These N-truncated fragments are typically at least 50, 60, 70, 80, 90, 100 or 110 amino acids in length. Generally at least 5-40, 10-30, or 15-25 (or any integer within these ranges) consecutive amino acids from the N-terminus of CCL23β are deleted. Thus, some FPRL1 ligand fragments are a truncated form of CCL23β in which 10, 12, 14, 16, 18, 20, 22, 24, 26, 28 or 30 consecutive amino acids from the N-terminus of the full length protein has been removed. FPRL1 ligand fragments include N-terminal truncated forms of CCL23β in which a N-terminal region has been removed by incubation with a protease, particularly a pro-inflammatory protease such as a serine protease (e.g., chymase, cathepsin G, or elastase), or a composition obtained from a source containing pro-inflammatory proteases. Sources of inflammatory proteases include, but are not limited to, cell extracts from immune cells or cell media used to culture immune cells (e.g., neutrophils, activated leukocytes), and physiological fluids taken from inflammatory tissue (e.g., synovial fluid from individuals suffering from an inflammatory disease or condition, such as rheumatoid arthritis, knee injuries, and osteoarthritis).

TABLE 2

SHAAGtide and various truncated and other variants - amino acid sequences.

| SEQ ID NO: | Designation and FPRL1 Activity | Amino acid sequence |
|---|---|---|
| 22 | CCXP1 Native sequence; high activity | Met Leu Trp Arg Arg Lys Ile Gly Pro Gln Met Thr Leu Ser His Ala Ala Gly (1-5-10-15-18) |
| 23 | CCXP2 Low activity | Arg Arg Lys Ile Gly Pro Gln Met Thr Leu Ser His Ala Ala Gly (1-5-10-15) |
| 24 | CCXP3 High activity | Met Leu Trp Arg Arg Lys Ile Gly Pro Gln Met Thr Leu Ser His (1-5-10-15) |
| 25 | CCXP4 Low activity | Ile Gly Pro Gln Met Thr Leu Ser His Ala Ala Gly (1-5-10) |
| 26 | CCXP5 Moderate activity | Met Leu Trp Arg Arg Lys Ile Gly Pro Gln Met Thr (1-5-10) |
| 27 | CCXP6 High activity | Met Leu Trp Arg Arg Lys Ile Gly Pro Gln Met Thr Leu Ser His Ala Ala Tyr (1-5-10-15-18) |
| 28 | CCXP7 Low activity | Trp Arg Arg Lys Ile Gly Pro Gln Met Thr Leu Ser His Ala Ala Gly (1-5-10-15) |
| 29 | CCXP8 Moderate activity | Met Leu Trp Arg Arg Lys Ile Gly Pro Gln Met (1-5-10) |

TABLE 2-continued

SHAAGtide and various truncated and other variants - amino acid sequences.

| SEQ ID NO: | Designation and FPRL1 Activity | Amino acid sequence |
|---|---|---|
| 30 | CCXP9 Low activity | Trp Arg Arg Lys Ile Gly Pro Gln Met<br>1           5 |
| 31 | CCXP10 Low activity | Trp Arg Arg Lys Ile Gly<br>1           5 |
| 32 | CCXP11 Moderate activity | Leu Trp Arg Arg Lys Ile Gly Pro Gln Met Thr Leu Ser His<br>1           5                     10 |
| 33 | | Leu Trp Arg Arg Lys Ile Gly Pro Gln Met Thr Leu Ser His Ala Ala Gly<br>1           5                     10                    15 |

TABLE 3

SHAAGtide and various truncated and other variants - polynucleotide sequences

| SEQ ID NO: | Polynucleotide sequence | |
|---|---|---|
| 34 | atgctctgga ggagaaagat tggtcctcag atgacccttt ctcatgctgc agga | 54 |
| 35 | aggagaaaga ttggtcctca gatgacccct tctcatgctg cagga | |
| 36 | atgctctgga ggagaaagat tggtcctcag atgacccttt ctcat | 45 |
| 37 | attggtcctc agatgaccct ttctcatgct gcagga | |
| 38 | atgctctgga ggagaaagat tggtcctcag atgacc | 36 |
| 39 | atgctctgga ggagaaagat tggtcctcag atgacccttt ctcatgctgc atat | 54 |
| 40 | tggaggagaa agattggtcc tcagatgacc ctttctcatg ctgcagga | |
| 41 | atgctctgga ggagaaagat tggtcctcag atg | 33 |
| 42 | tggaggagaa agattggtcc tcagatg | |
| 43 | tggaggagaa agattggt | |
| 44 | ctctggagga gaaagattgg tcctcagatg acccttctc at | 42 |

Another derivative of CCL23β that has SHAAGtide-like activity (CCL23β Δ24; SEQ ID NO:45), is shown in Table 4; the nucleotide sequence that encodes SEQ ID NO:45 is shown in Table 5. The sequences corresponding to SEQ ID NOS:22 and 34 are underlined.

TABLE 4

Polypeptide sequence of CCL23β Δ24 (SEQ ID NO:45)

<u>Met Leu Trp Arg Arg Lys Ile Gly Pro Gln Met Thr Leu Ser His Ala
1           5                    10                   15

Ala Gly</u> Phe His Ala Thr Ser Ala Asp Cys Cys Ile Ser Tyr Thr Pro
        20                    25                        30

Arg Ser Ile Pro Cys Ser Leu Leu Glu Ser Tyr Phe Glu Thr Asn Ser
        35                    40                        45

Glu Cys Ser Lys Pro Gly Val Ile Phe Leu Thr Lys Lys GLy Arg Arg
        50                    55                60

TABLE 4-continued

Polypeptide sequence of CCL23β Δ24 (SEQ ID NO:45)

```
Phe Cys Ala Asn Pro Ser Asp Lys Gln Val Gln Val Cys Met Arg Met
 65              70                  75                  80

Leu Lys Leu Asp Thr Arg Ile Lys Thr Arg Lys Asn
                 85                  90
```

TABLE 5

Polynucleotide sequence of CCL23β Δ24 (SEQ ID NO:46)

| | |
|---|---|
| atgctctgga gqagaaagat tggtcctcag atgacccttt ctcatgctgc aggattccat | 60 |
| gctactagtg ctgactgctg catctcctac accccacgaa gcatcccgtg ttcactcctg | 120 |
| gagagttact ttgaaacgaa cagcgagtgc tccaagccgg gtgtcatctt cctcaccaag | 180 |
| aagggcgac gtttctgtgc caaccccagt gataagcaag ttcaggtttg catgagaatg | 240 |
| ctgaagctgg acacacggat caagaccagg aagaattga | 279 |

V. Nucleic Acids Encoding Alternative CCR1 and FPRL1 Ligands

Nucleic acids that encode CCR1 and/or FPRL1 alternative ligands (e.g., CCR1 and/or FPRL1 ligand fragments) and fusion proteins containing CCR1 and/or FPRL1 alternative ligands are also provided. These nucleic acids include those that encode for polypeptides having the sequence of SEQ ID NOs:2, 3, 5-8, 10-15, 17-21, 22-33, or 45. Other nucleic acids encode fusion proteins that include a CCR1 and/or FPRL1 ligand fragment (e.g., SEQ ID NOs:2, 3, 5-8, 10-15, 17-21, 22-33, or 45) which is fused to a polypeptide tag as indicated above.

Nucleic acids encoding the CCR1 and/or FPRL1 ligand fragments can be prepared according to conventional techniques known in the art. Based upon the sequence information provided herein and knowledge in the art regarding the nucleic acids that encode CCL6, CCL9, CCL15, CCL23, and CCL23β, the CCR1 and FPRL1 ligand fragment polypeptides that are described herein can be produced by recombinant means. See, e.g., Sambrook et al., Molecular Cloning: A Laboratory Manual, 3rd edition, Cold Spring Harbor Press, N.Y., (2001), Berger and Kimmel, (1987) Methods In Enzymology, Vol. 152: Guide To Molecular Cloning Techniques, San Diego: Academic Press, Inc.; Ausubel et al., Current Protocols In Molecular Biology, Greene Publishing and Wiley-Interscience, New York (1999).

Alternatively, the polynucleotides can be chemically synthesized. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is often limited to sequences of about 100 bases, longer sequences may be obtained by the ligation of shorter sequences. Alternatively, subsequences may be cloned and the appropriate subsequences cleaved using appropriate restriction enzymes. The fragments can then be ligated to produce the desired DNA sequence.

If it is desired to modify the nucleic acids that are disclosed herein, this can be accomplished using a variety of established techniques. Examples of such methods include, for instance, site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) Gene 8:81-97, Roberts et al. (1987) Nature 328: 731-734.

Vectors including the nucleic acids and cells containing such vectors are also provided. These are described in greater detail in the following section.

VI. Production of CCR1 and FPRL1 Ligand Fragments

The CCR1 and/or FPRL1 ligand fragment polypeptides that are disclosed herein can be prepared using recombinant or synthetic methods. The fragments can also be isolated from natural cellular sources. Examples of such sources include, but are not limited to, inflamed tissue or fluid obtained from inflamed tissue. Specific examples of include physiological fluids taken from inflamed tissue (e.g., synovial fluid from individuals suffering from an inflammatory disease or condition, such as rheumatoid arthritis, knee injuries and osteoarthritis).

A variety of recombinant techniques for expressing CCR1 and FPRL1 ligand fragment polypeptides from polynucleotides encoding the fragments can be utilized to prepare the fragments. Typically, a polynucleotide encoding a CCR1 or FPRL1 ligand fragment (see supra) is inserted into an expression vector. Expression vectors typically include transcriptional and/or translational control signals (e.g., the promoter, ribosome-binding site, and ATG initiation codon). In addition, the efficiency of expression can be enhanced by the inclusion of enhancers appropriate to the cell system in use. For example, the SV40 enhancer or CMV enhancer can be used to increase expression in mammalian host cells. The expression vector can include a "recombinant expression cassette" or simply an "expression cassette" in which a segment encoding the CCR1 and/or FPRL1 ligand fragment is operably linked to control elements compatible with the host in which expression is carried out. The expression cassette can also include additional factors necessary or helpful in effecting expression, such as transcription termination signals, enhancers, and other nucleic acid sequences that influence gene expression.

In some methods, DNA encoding a CCR1 and/or FPRL1 ligand fragment is inserted into DNA constructs capable of introduction into and expression in an in vitro host cell, such as a bacterial (e.g., *E. coli, Bacillus subtilus*), yeast (e.g., *Saccharomyces*), insect (e.g., *Spodoptera frugiperda*), or mammalian cell culture systems. Examples of mammalian cell culture systems useful for expression and production of the CCR1 and/or FPRL1 ligand fragments include human embryonic kidney line (293; Graham et al., 1977, *J. Gen. Virol.* 36:59); CHO (ATCC CCL 61 and CRL 9618); human cervical carcinoma cells (HeLa, ATCC CCL 2); COS-7 cells; NIH-3T3 cells; HEK-293 cells; K-562 cells; and others known in the art. The use of mammalian tissue cell culture to express polypeptides is discussed generally in Winnacker, FROM GENES TO CLONES (VCH Publishers, N.Y., N.Y., 1987) and Ausubel et al., Current Protocols In Molecular Biology, Greene Publishing and Wiley-Interscience, New York (supplemented through 1999).

In some embodiments, promoters from mammalian genes or from mammalian viruses are used, e.g., for expression in mammalian cell lines. Suitable promoters can be constitutive, cell type-specific, stage-specific, and/or modulatable or regulatable (e.g., by hormones such as glucocorticoids). Useful promoters include, but are not limited to, the metallothionein promoter, the constitutive adenovirus major late promoter, the dexamethasone-inducible MMTV promoter, the SV40 promoter, and promoter-enhancer combinations known in the art.

Further guidance on the expression of CCR1 and/or FPRL1 ligand fragments is provided, for example, in Sambrook et al., Molecular Cloning: A Laboratory Manual, 3rd edition, Cold Spring Harbor Press, N.Y., (2001), and in Ausubel et al., Current Protocols In Molecular Biology, Greene Publishing and Wiley-Interscience, New York (supplemented through 1999). Synthetic methods for synthesizing polypeptides such as CCX CKR polypeptides, variants, or fragments are described in Merrifield, 1963, *Amer. Chem. Soc.* 85:2149-2456, Atherton et al., 1989, SOLID PHASE PEPTIDE SYNTHESIS: A PRACTICAL APPROACH, IRL Press, and Merrifield, 1986, *Science* 232:341-347.

Isolation and purification of the CCR1 and/or FPRL1 ligand fragments produced in expression systems or from natural sources can be carried out by methods that are conventional in the art. These methods include, but are not limited to, ion exchange, hydrophobic interaction, HPLC or affinity chromatography, to achieve the desired purity. In one exemplary approach, CCR1 and/or FPRL1 ligand fragment polypeptides are purified using immunoaffinity chromatography. For example, antibodies raised against a CCR1 and/or FPRL1 ligand fragment or immunogenic fragment thereof (e.g., having a sequence or subsequence of SEQ ID NOs:2, 3, 5-8, 10-15, 17-21, 22-33, or 45) are coupled to a suitable solid support and contacted with a mixture containing the CCR1 and/or FPRL1 ligand fragment polypeptide under conditions conducive to the association of this polypeptide with the antibody. Once the CCR1 and/or FPRL1 ligand fragment polypeptide is bound to the immobilized antibody, the solid support is washed to remove unbound material and/or non-specifically bound polypeptides. The desired polypeptide can then be eluted from the solid support in substantially pure form by, e.g., a change in pH or salt concentration of the buffer.

VII. Methods of Screening for Agents that Modulate Capacity of a CCR1 Ligand Fragment to Bind or Activate CCR1 and of FPRL1 Ligand Fragment to Bind or Activate FPRL1

Because the CCR1 ligand fragments that are described herein are strong activators of CCR1, they can be used as ligands in various screening methods to identify modulators of CCR1 activity. Other CCR1 ligands can also be used including, for example, CCL3, RANTES, MCP-2, MCP-3, as well as CCL6, CCL9, CCL15 and CCL25 (untruncated forms). The CCR1 ligand fragments that are provided are useful because of their strong affinity for the receptor, thereby enabling modulators with strong affinity for the receptor to be identified.

Because the FPRL1 ligand fragments that are described herein are strong activators of FPRL1, they can be used as ligands in various screening methods to identify modulators of FPRL1 activity. Other FPRL1 ligands can also be used including, for example, those described in Table 1. The FPRL1 ligand fragments that are provided are useful because of their strong affinity for the receptor, thereby enabling modulators with strong affinity for the receptor to be identified.

A. Binding Assays

Competition binding assays can also be used in the screening methods. In assays of this type, a known ligand of CCR1 and/or FPRL1, such as those provided herein (e.g., a CCR1 ligand fragment and/or a FPRL1 ligand fragment), or a variant or fragment thereof that retains binding activity, is combined with CCR1 and/or FPRL1 in the presence of a test agent. The extent of binding between the known ligand and CCR1 and/or FPRL1 in the presence of the test agent is compared with the level of ligand binding in a control, typically a similar assay conducted in the absence of the test agent. A difference (e.g., a statistically significant difference) between the test and control assays is an indication that the test agent is a modulator of CCR1 and/or FPRL1 activity. An increase in binding of the known ligand is an indication that the test agent is an agonist. A decrease in binding of the known ligand, in contrast, is an indication that the test agent is an antagonist.

The binding assays can be conducted as cell-based assays, which use cells that naturally express CCR1 (e.g., isolated blood cells such as T cells) or cells that have been stably or transiently transfected and thus express CCR1. For FPRL1, the binding assays can also be conducted as cell-based assays, which use cells that naturally express FPRL1 (e.g., monocytes or neutrophils) or cells that have been stably or transiently transfected and thus express FPRL1 (e.g., L1.2-FPRL1 transfectants) The cells are maintained under conditions appropriate for expression of the receptors and are contacted with the test agent and the known ligand under conditions appropriate for binding to occur. Binding can be detected using standard techniques. For example, the extent of binding can be determined relative to a suitable control (for example, relative to background in the absence of a putative agent, or relative to a known ligand). Optionally, a cellular fraction, such as a membrane fraction, containing the receptor can be used in lieu of whole cells. Detection of binding or complex formation can be detected directly or indirectly. For example, the test agent or the known ligand can be labeled with a suitable label (e.g., fluorescent label, chemiluminescent label, isotope label, enzyme label, and the like) and binding can be determined by detection of the label.

Other binding assays, however, are non-cellular assays. Such assays can be conducted by immobilizing CCR1 and/or FPRL1 to a support, for example, and the contacting the immobilized receptor with a composition containing the test agent. Formation of complex can be detected and optionally quantified as just described. The CCR1 protein in such assays may be a fusion protein that includes a CCR1 domain that retains an activity of CCR1 and a tag (e.g., any of the polypeptide tags listed supra). The FPRL1 protein in such assays may be a fusion protein that includes an FPRL1 domain that retains an activity of FPRL1 and a tag (e.g., any of the polypeptide tags listed supra). In these assays, the fusion protein is immobilized to a support via the tag (e.g., an antibody deposited on the support that binds the tag).

Further guidance regarding receptor binding assays is provided, for example, by Parce et al., 1989, *Science* 246: 243-247; and Owicki et al., 1990, *Proc. Nat'l Acad. Sci. USA* 87: 4007-4011.

B. Biological Assays

Other screening assays that are provided are designed not only to determine whether a test agent binds CCR1 and/or FPRL1, but also determine if the test agent can modulate a CCR1 activity and/or FPRL1 activity, respectively. Because both CCR1 and FPRL1 are G-protein coupled receptors, the binding of a ligand to CCR1 and/or FPRL1 can result in signaling, and the activity of G proteins as well as other intracellular signaling molecules can be stimulated. Examples of biological activities mediated by both, CCR1 and FPRL1 include calcium mobilization, chemotaxis and cell proliferation. The induction of a biological function by a test agent can be monitored using any suitable method. The capacity of a test agent to modulate the activity of CCR1 and/or FPRL1 can be determined in the presence of a ligand, e.g., a CCR1 and/or FPRL1 alternative ligand, including CCR1 and/or FPRL1 ligand fragments (e.g., SEQ ID NOs:2-3, 5-8, 10-15, 17-21 and 22-33). The examples provide further details on certain cell migration assays that can be utilized in the screening methods.

1. Calcium Mobilization

G protein activity, such as hydrolysis of GTP to GDP, or later signaling events triggered by receptor binding, such as induction of rapid and transient increase in the concentration of intracellular (cytosolic) free calcium can be assayed according to various methods (see e.g., Neote, K. et al., (1993) *Cell*, 72: 415-425); Van Riper et al., (1993) *J. Exp. Med.*, 177: 851-856; Dahinden, C. A. et al., (1994) *J. Exp. Med.*, 179: 751-756; and U.S. Pat. No. 5,284,746). The examples below also describe an assay for detecting calcium flux triggered by CCR1 and/or FPRL1.

2. Chemotaxis and Assays of Cellular Stimulation

Chemotaxis assays can also be used to assess the ability of a test agent to block binding of a ligand to CCR1 or of a ligand to FPRL1 and thus modulate function associated with binding of the ligands to the receptors. These assays are based on the functional migration of cells in vitro or in vivo induced by a CCR1 ligand and/or by an FPRL1 ligand. Various chemotaxis assays that are suitable for use in the current screening methods are suitable. One such assay is the use of an in vitro transendothelial chemotaxis assay is described by Springer et al. (Springer et al., WO 94/20142; see also Berman et al., (1988) *Immunol. Invest.* 17: 625-677). Other suitable assays involve detection of migration across endothelium into collagen gels (see, e.g., Kavanaugh et al., (1991) *J. Immunol.*, 146: 4149-4156). Stable transfectants of mouse L1.2 pre-B cells or of other suitable host cells capable of chemotaxis can be used in chemotaxis assays, for example.

Some chemotaxis assays detect the directional movement or migration of a suitable cell (such as a leukocyte (e.g., lymphocyte, eosinophil, basophil)) into or through a barrier (e.g., endothelium, a filter), toward increased levels of a test agent, from a first surface of the barrier toward an opposite second surface. Membranes or filters provide convenient barriers, such that the directional movement or migration of a suitable cell into or through a filter, toward increased levels of a compound, from a first surface of the filter toward an opposite second surface of the filter, is monitored.

To assess migration and inhibition of migration, the distance of migration into the filter, the number of cells crossing the filter that remain adherent to the second surface of the filter, and/or the number of cells that accumulate in the second chamber can be determined using standard techniques (e.g., microscopy). In some assays, the cells are labeled with a detectable label (e.g., radioisotope, fluorescent label, antigen or epitope label), and migration can be assessed in the presence and absence of the test agent by determining the presence of the label adherent to the membrane and/or present in the second chamber using an appropriate method (e.g., by detecting radioactivity, fluorescence, immunoassay). The extent of migration can be determined relative to a suitable control (e.g., compared to background migration determined in the absence of the test agent, compared to the extent of migration induced by a second agent (i.e., a standard), or compared with migration of untransfected cells induced by the antibody).

One specific example of an assay that can be used to detect agents that are inhibitors of migration involves initially placing CCR1-expressing cells that are capable of migration in a first chamber. A composition comprising one or more ligands (e.g., a CCR1 ligand fragment) capable of inducing chemotaxis of the cells in the first chamber (having chemoattractant function) is placed in a second chamber. Shortly before the cells are placed in the first chamber, or simultaneously with the cells, a composition containing the test agent is typically placed in the first chamber. Test agents that can bind CCR1 and inhibit the induction of chemotaxis by the ligand, of the cells expressing CCR1 are inhibitors of receptor function (e.g., inhibitors of stimulatory function). A reduction in the extent of migration induced by the ligand in the presence of the test agent is indicative of inhibitory activity.

Another example of an assay that can be used to detect agents that are inhibitors of migration involves initially placing FPRL1-expressing cells that are capable of migration in a first chamber. A composition comprising one or more ligands (e.g., a FPRL1 ligand fragment) capable of inducing chemotaxis of the cells in the first chamber (having chemoattractant function) is placed in a second chamber. Shortly before the cells are placed in the first chamber, or simultaneously with the cells, a composition containing the test agent is typically placed in the first chamber. Test agents that can bind FPRL1 and inhibit the induction of chemotaxis by the ligand, of the cells expressing FPRL1 are inhibitors of receptor function (e.g., inhibitors of stimulatory function). A reduction in the extent of migration induced by the ligand in the presence of the test agent is indicative of inhibitory activity.

Some in vivo cell migration assays are discussed in U.S. Pat. No. 6,756,035, disclosure of which is incorporated by reference in its entirety. These assays involve monitoring leukocyte infiltration of a tissue, in response to injection of an agent in the tissue. These in vivo models measure the ability of cells to respond to a ligand by chemotaxis to a site of inflammation and assess the ability of a test agent to affect this movement.

3. Exemplary Cell Proliferation Assays

Cellular proliferation assays can be conducted in a variety of different ways, including, for example: actual cell counting, clonogenic assays, measuring metabolic activity, measuring DNA synthesis and/or measuring the level of molecules that regulate cell cycle (e.g., CDK kinase assays). A brief summary of these approaches follows. For a general review of some of these approaches, see for example, Roche Molecular Biochemicals, "Apoptosis and Cell Proliferation", $2^{nd}$ Revised edition, pages 66-114, which is incorporated herein by reference in its entirety for all purposes. Regardless of the particular approach taken for determining cell proliferation, screening methods that involve monitoring cell proliferation usually involve contacting a cell or cell population expressing CCR1 with a CCR1 ligand (e.g., a CCR1 alternative ligand such as a CCR1 ligand fragment) in the presence of a test agent and then determining the level of cell proliferation in the presence of the test compound. The determined level of cell proliferation is then compared with the level of cell proliferation in the absence of the test agent. A decrease in activity in the presence of the test agent indicates that it is an inhibitor of CCR1, whereas an increase in cell proliferation indicates that the test agent is an activator of CCR1.

For FPRL1, screening methods that involve monitoring cell proliferation usually involve contacting a cell or cell population expressing FPRL1 with a FPRL1 ligand (e.g., an FPRL1 alternative ligand such as an FPRL1 ligand fragment) in the presence of a test agent and then determining the level of cell proliferation in the presence of the test compound. The determined level of cell proliferation is then compared with the level of cell proliferation in the absence of the test agent. A decrease in activity in the presence of the test agent indicates that it is an inhibitor of FPRL1, whereas an increase in cell proliferation indicates that the test agent is an activator of FPRL1.

One approach to detect cell proliferation is simply to count the number of cells using a cell counting device such as a hemacytometer (see, e.g., Example 1). In the clonogenic assay approach, a defined number of cells are plated out onto a suitable media and the number of colonies that are formed after a defined period of time are determined. The clonogenic approach can be somewhat cumbersome for large number of samples and for cells that divide only a few times and then become quiescent.

A number of different assays for measuring metabolic activity are available. One approach is to incubate the cells with a tetrazolium salt (e.g., MTT, XTT or WST-1), which becomes cleaved during cellular metabolism to form a colored formazan product. Further guidance regarding assays of this type are provided by Cook, J. A. and Mitchell, J. B. (1989) Anal. Biochem. 179:1; Roehm, N. W. et al. (1991) J. Immunol. Methods 142:257; Slater, T. F., et al. (1963) Biochem. Biophys. Acta 77:383; Berridge, M. V. and Tan, A. S. (1993) Arch. Biochem. Biophys. 303:474; Cory, A. H., et al. (1991) Cancer Commun. 3:207; Jabbar, S. A. B., et al. (1989) Br. J. Cancer 60: 523; and Scudiero, E. A., et al. (1988) Cancer Res. 48, 4827, each of which is incorporated herein by reference in its entirety for all purposes. A variety of kits for performing such assays are available from Roche Molecular Biochemicals. Other assays in this class involve the measurement of ATP and involve detecting the formation of luminescence formed via the activity of luciferase. Such assays are commercially available from Perkin Elmer (see, e.g., ATPlite™ Assay kits).

Because DNA is replicated during cell proliferation, assays that provide a measure of DNA replication also provide an useful measure of cell proliferation. Assays of this type typically involve adding labeled DNA precursors to a cell culture. Cells that are about to divide incorporate the labeled nucleotide into their DNA. Some approaches utilize tritiated thymidine ([3H]-TdR) and measure the amount of incorporated tritiated thymidine using liquid scintillation counting. To avoid using radioactive compounds, other assays utilize the thymidine analog 5-bromo-2'deoxy-uridine (BrdU), which becomes incorporated into DNA just like thymidine. Incorporated BrdU can be detected quantitatively using a cellular immunoassay that utilizes monoclonal antibodies directed against BrdU. Commercial kits for performing such assays are available from a number of sources including Roche Molecular Biochemicals.

Other assays capitalize on the fact that certain cell cycle antigens are specific to proliferating cells. Molecules involved in the regulation of cell cycle can be detected either by their activity or by quantitating their amount (e.g., via Western blots, ELISA or immunohistochemistry). Examples of nuclear antigens present only in proliferating cells that can be measured include, but are not limited to, proliferating cell nuclear antigen (PCNA), Ki-67 and topoisomerase II-alpha (Ki-S1). Kits commercially available to perform such assays are available from various suppliers, including Roche Molecular Biochemicals.

C. Test Agents

A variety of different types of agents can be screened for the ability to modulate the activity of a protease that cleaves the N-terminal region of CCL6, CCL9, CCL15, CCL23 and CCL23β, and thus indirectly the activity of CCR1 and/or FPRL1. The agents can be agonists or antagonists. The agents can be include, for example, antibodies, peptides or small molecules, hormones, growth factors, cytokines, chemokines, naturally occurring molecules, or molecules from existing repertoires of chemical compounds synthesized by the pharmaceutical industry. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in PCT Publications WO 95/12608, WO 93/06121, WO 94/08051, 95/35503 and WO 95/30642. Peptide libraries can also be generated by phage display methods. See, e.g., Devlin, WO 91/18980. Compounds to be screened can also be obtained from the National Cancer Institute's Natural Product Repository, Bethesda, Md., as well as a number of other commercial sources. The agents to be screened can also be agonist antibodies and antagonist antibodies. A general review of methods for preparing libraries is provided by Dolle and Nelson (*J. Combinatorial Chemistry* 1: 235-282 (1999)).

VIII. Methods of Screening for Agents that Modulate the Production of CCR1 and FPRL1 Ligand Fragments A. General The identification as described herein of the proteases that are responsible for converting CCL6, CCL9, CCL15, CCL23, and CCL23β into forms that can activate CCR1 and/or FPRL1 provides the basis for screening methods designed to identify agents that modulate the activity of these proteases.

Agents so identified can thus be used to indirectly modulate the activity of CCR1 and/or FPRL1 by modulating the activity of the enzymes that produce ligands for CCR1 and/or FPRL1. Identified agents that agonize the activity of the protease, can be used to stimulate CCR1 and/or FPRL1 responses (e.g., beneficial immune responses); whereas, agents that antagonize these proteases can be used to inhibit undesirable CCR1 and/or FPRL1 responses (e.g., harmful inflammatory responses).

One method of screening involves combining a protease that can activate CCL6, CCL9, CCL15, CCL23, and/or CCL23β (i.e., remove the inhibitory N-terminal region) with a known substrate for the protease. The protease is typically a pro-inflammatory protease, generally a serine protease such as recombinant mast cell chymase, purified neutrophil cathepsin G, or elastase. The activity of the protease is then determined in the presence of the substrate and a test agent that is thought to be a potential modulator of the protease. The activity that is determined is then compared with the activity of a control, which typically is an assay conducted without the test agent. A difference (e.g., a statistically significant difference) is an indication that the test agent is a modulator of the protease. For example, if the activity in the presence of the test agent is higher than in the absence of the test agent, then the test agent is preliminarily identified as an activator of the protease and thus a potential activator (indirectly) of CCR1 and/or FPRL1 activity. If on the other hand, the activity in the presence of the test agent is lower than in the absence of the test agent, then the test agent is identified as a potential inhibitor (indirectly) of the protease and thus a potential inhibitor of CCR1 and/or FPRL1.

B. Proteases Used in Assay

The protease used in the assay can be any of a number of pro-inflammatory protease such as the serine proteases. Specific examples include chymase, cathepsin G, or elastase. The substrate specificities of these enzymes are known. Guidance on appropriate substrates and methods for assaying the activity of the enzymes is provided, for example, by the following articles: (1) chymase (see, e.g., Raymond, W. W., et al. (2003) J. Biol. Chem. 278:34517-34524; Akahoshi, F. (2003) Current Pharmaceutical Design 9:1191-1199; and Solivan, S. et al. (2002) FEBS Letters 512:133-138); (2) cathepsin G (see, e.g., Rehault, S. (1999) J. Biol. Chem. 274:13810-13817; and Polanowska, J. (1998) Biochim. Biophys. Acta. 1386:189-198); and (3) elastase (see, e.g., Korkmaz, B. et al. (2004) Am. J. Respir. Cell Mol. Biol. 30:801-807; and McBride J. D., et al. (1999) Eur. J. Biochem. 266:403-412). Of course, the substrate utilized in these assays can be CCL6, CCL9, CCL15 or CCL23. Alternatively, solutions containing pro-inflammatory proteases can be used (e.g., activated neutrophil-conditioned media, fluids from inflamed tissue (e.g., synovial fluid)).

C. Validation

An agent identified in the initial screening process can subsequently be tested to determine if it modulates the activity of CCR1 and/or FPRL1. Such assays include calcium mobilization assays, cellular migration assays, cell proliferation assays, and various signaling assays, since these are all activities that are mediated by CCR1 and/or FPRL1. These assays are described above and in the examples.

Additional examples of models of inflammation that can be used to assess the ability of and agent identified in a screening method to exert an effect in vivo, include: a sheep model for asthma (see, Weg et al., 1993, *J. Exp. Med.* 177:561); and a rat delayed-type hypersensitivity model (see Rand et al., 1996, *Am. J. Pathol.*, 148:855-864). Another useful model for evaluating the agents that are identified is the experimental autoimmune encephalomyelitis (EAE) model for multiple sclerosis, which probes chemokine receptor expression and function (see, Ransohoff et al., 1996, *Cytokine Growth Factor Rev.*, 7:35-46, and Karpus et al., 1998, *J. Immunol.* 161:2667-2671). In addition, leukocyte infiltration assays can also be used to evaluate an identified agent (see, Van Damme, et al., 1992, *J. Exp. Med.*, 176:59-65; Zachariae et al., 1990, *J. Exp. Med,* 171:2177-2182; and Jose et al., 1994, *J. Exp. Med.*, 179:881-887).

IX. Antibodies to CCR1 and FPRL1 Ligand Fragments

Antibodies that are specifically immunoreactive with CCR1 and/or FPRL1 ligand fragments (e.g., polypeptides with the amino acid sequence of SEQ ID NOs:2-3, 5-8, 10-15, 17-21, or 22-33) are also provided. Such antibodies usually exhibit a specific binding affinity for CCR1 and/or FPRL1 ligand fragments of at least about $10^7$, $10^8$, $10^9$, or $10^{10}$ $M^{-1}$. These antibodies can be used for a variety of purposes, including isolation of CCR1 and/or FPRL1 ligand fragments (e.g., by immunoaffinity chromatography), detection of CCR1 and/or FPRL1 ligand fragments, and for inhibition of CCR1 and FPRL1 activity, either in vitro or in vivo.

A. Production of Antibodies to CCR1 Ligand Fragments

Antibodies are broadly defined herein and specifically include fragments, chimeras and similar binding agents (e.g., the products of phage display technology), that specifically bind a CCR1 and/or FPRL1 ligand fragment or epitope thereof. Some antibodies are selected not to have cross-reactivity with full-length CCL6, CCL9, CCL15, CCL23, CCL23β and/or other ligands for CCR1 and FPRL1 (e.g., CCL3/MIP-1α, RANTES, MCP-2, and/or MCP-3 (for CCR1); and those identified in Table 1 for FPRL1).

The antibodies can be prepared by a variety of methods. Methods for production of polyclonal or monoclonal antibodies, for instance, are well known in the art. See, e.g., Coligan, CURRENT PROTOCOLS IN IMMUNOLOGY, Wiley/Greene, N.Y. (1991); Stites et al. (eds.) BASIC AND CLINICAL IMMUNOLOGY (7th ed.) Lange Medical Publications, Los Altos, Calif., and references cited therein ("Stites"); Goding, MONOCLONAL ANTIBODIES: PRINCIPLES AND PRACTICE (2d ed.) Academic Press, New York, N.Y. (1986); Kohler and Milstein, 1975, *Nature* 256: 495-97; and Harlow and Lane (1988) *Antibodies, A Laboratory Manual*, Cold Spring Harbor Publications, New York. These techniques include antibody preparation by selection of antibodies from libraries of recombinant antibodies in phage or similar vectors. See, Huse et al., 1989, *Science* 246:1275-81; and Ward et al., 1989, *Nature* 341:544-46.

For production of polyclonal antibodies, an appropriate target immune system is selected, typically a mouse or rabbit, but also including goats, sheep, cows, chickens, guinea pigs, monkeys and rats. The immunoglobulins produced by the host can be precipitated, isolated and purified by routine methods, including affinity purification. Substantially monospecific antibody populations can be produced by chromatographic purification of polyclonal sera.

For monoclonal antibodies, appropriate animals will be selected and the desired immunization protocol followed. The antibodies of the invention may be of any isotype, e.g., IgM, IgD, IgG, IgA, and IgE, with IgG, IgA and IgM most referred. Preferred monoclonal anti-CCX CKR antibodies neutralize (i.e., inhibit or block) one or more biological activities of CCX CKR. Such antibodies may be obtained by screening hybridoma supernatants for the desired inhibitory activity. Monoclonal antibodies with affinities of $10^8$ liters/mole, preferably $10^9$ to $10^{10}$ or stronger, can be produced by the methods described below. The production of non-human monoclonal antibodies, e.g., murine, lagomorpha, or equine, is well known and can be accomplished by, e.g., immunizing a host animal with a preparation containing CCX CKR or fragments thereof. Antibody-producing cells obtained from the immunized animals are immortalized and screened, or screened first for the production of antibody which binds to the CCX CKR polypeptide and then immortalized.

Some anti-CCR1 ligand fragment monoclonal antibodies and anti-FPRL1 ligand fragment monoclonal antibodies are humanized, human or chimeric, in order to reduce their potential antigenicity, without reducing their affinity for their target. Humanized antibodies have been described in the art. See, e.g., Queen, et al., 1989, *Proc. Nat'l Acad. Sci. USA* 86:10029; U.S. Pat. Nos. 5,563,762; 5,693,761; 5,585,089 and 5,530,101. The human antibody sequences used for humanization can be the sequences of naturally occurring human antibodies or can be consensus sequences of several human antibodies. See Kettleborough et al., *Protein Engineering* 4:773 (1991); Kolbinger et al., *Protein Engineering* 6:971 (1993). Humanized monoclonal antibodies against CCX CKR can also be produced using transgenic animals having elements of a human immune system (see, e.g., U.S. Pat. Nos. 5,569,825; 5,545,806; 5,693,762; 5,693,761; and 5,7124,350).

Useful anti-CCR1 and anti-FPRL1 ligand fragments can also be produced using phage display technology (see, e.g., Dower et al., WO 91/17271 and McCafferty et al., WO 92/01047). In these methods, libraries of phage are produced in which members display different antibodies on their outer surfaces. Antibodies are usually displayed as Fv or Fab fragments. Phage displaying antibodies with a desired specificity are selected by affinity enrichment to a CCR1 and/or FPRL1 ligand fragment.

Once expressed, the whole antibodies, their dimers, individual light and heavy chains, or other immunoglobulin forms of the present invention can be purified according to standard procedures of the art, including ammonium sulfate precipitation, affinity chromatography, gel electrophoresis and the like (see generally PROTEIN PURIFICATION: PRINCIPLES AND PRACTICE 3RD EDITION (Springer-Verlag, N.Y., 1994)).

An antibody as provided herein is substantially pure when at least about 80%, more often at least about 90%, even more often at least about 95%, most often at least about 99% or more of the polypeptide molecules present in a preparation specifically bind the same antigen (e.g., a CCR1 and/or FPRL1 ligand fragment). For pharmaceutical uses, immunoglobulins of at least about 90 to 95% homogeneity are preferred, and 98 to 99% or more homogeneity are most preferred.

B. Modification of CCR1 Ligand Fragment Antibodies and FPRL1 Ligand Fragment Antibodies The antibodies just described can be used with or without modification. But in some applications the antibodies are labeled by joining, either covalently or non-covalently, a substance which provides for a detectable signal. Such labels include, e.g., radioactive, fluorescent, or bioactive (e.g., enzymatic) labels. As labeled binding entities, the antibodies can be used in diagnostic applications, for instance.

C. Selection of Non-Cross Reacting Antibodies

In some instances, monoclonal or polyclonal antiserum is produced that is specifically immunoreactive with a CCR1 and/or FPRL1 ligand fragment but is selected to have low cross-reactivity against other ligands for CCR1, FPRL1, and/ or other chemokines. Cross-reactive antibodies can be removed by immunoabsorption prior to use in the immunoassay. Methods for screening and characterizing monoclonal antibodies for specificity are well known in the art and are described generally in Harlow and Lane (1988) *Antibodies, A Laboratory Manual*, Cold Spring Harbor Publications, New York.

In order to produce a polyclonal antisera (e.g., for use in an immunoassay), a polyclonal antiserum is prepared against a CCR1 and/or FPRL1 ligand fragment using methods well known in the art, such as those described supra. For example, recombinant protein may be produced in a mammalian cell line. An inbred strain of mice such as balb/c is immunized with the CCR1 ligand fragment (and/or FPRL1 ligand fragment) using a standard adjuvant, such as Freund's adjuvant, and a standard mouse immunization protocol (see Harlow and Lane, supra). Alternatively, a synthetic peptide derived from the sequences disclosed herein and conjugated to a carrier protein can be used as an immunogen. Polyclonal sera are collected and titered against the immunogen protein in an immunoassay, for example, a solid phase immunoassay with the immunogen immobilized on a solid support. Polyclonal antisera with a titer of $10^4$ or greater are selected and tested for their cross reactivity against other chemokines (e.g., other ligands for CCR1 (or ligands for FPRL1) as listed above) using a competitive binding immunoassay such as the one described in Harlow and Lane, supra, at pages 570-573. Immunoassays in the competitive binding format can be used for the cross-reactivity determinations. For example, a CCR1 and/or FPRL1 ligand fragment can be immobilized to a solid support. Proteins added to the assay compete with the binding of the antisera to the immobilized antigen. The ability of the above proteins to compete with the binding of the antisera to the immobilized protein is compared to the CCR1 and/or FPRL1 ligand fragment. The percent cross-reactivity for the above proteins is calculated, using standard calculations. Typically, those antisera with less than 10% cross-reactivity with each of the tested chemokines are selected and pooled. The cross-reacting antibodies are then removed from the pooled antisera by immunoabsorbtion with the other ligands of CCR1 and/or FPRL1.

X. Modulatory Agents

A variety of agents are provided that can activate or inhibit the production of CCR1 and/or FPRL1 ligand fragments or their ability to bind to and/or activate CCR1 and/or FPRL1, respectively. These agents, thus, can be used to either increase or decrease the CCR1 and/or FPRL1 activity as desired. Agents such as those that follow can be formulated as a pharmaceutical composition as described below.

A. Agents that Modulate the Formation of CCR1 and/or FPRL1 Ligand Fragments

1. Inhibitors

Some agents that are provided inhibit the formation of a CCR1 and/or FPRL1 ligand fragment. These agents can thus be used to indirectly inhibit CCR1 and/or FPRL1 activity. Some of these agents are polypeptides or polypeptide mimetics (see infra) that are similar in structure and sequence to CCL6, CCL9, CCL15, CCL23, or CCL23β, but contain a modification in a cleavage region that encompasses the site at which a protease such as those listed above would normally cleave these chemokines to produce a CCR1 and/or FPRL1 ligand fragment (i.e., an N-terminal truncated form). Such compounds are referred to herein as "CCR1 ligand analogues" Or "FPRL1 ligand analogues," respectively. Typically, the modification is either at the site the protease normally cleaves at or is within 1-5 amino acids on either side of the cleavage site. Thus, the cleavage region at which the modification occurs can extend up to about 10 amino acids in length. In some instances, however, the modification may be further away from the cleavage site. Examples of the type of modifications that can be made with in the cleavage region include, but are not limited to, acetylation, methylation, or phosphorylation of one or more amino acids in the cleavage region, and/or inclusion of a non-peptide linkage, or use of a non-cleavable or non-hydrolysable amino acid analog in the cleavage region. The modification may also involve a deletion or substitution of one or more amino acids (typically only 1-5 amino acids).

Some CCR1 ligand analogues include the following analogues of CCL6, CCL9, CCL15 and CCL23 that have the following characteristics:

(a) a CCL6 analogue that comprises a CCL6 amino acid sequence (SEQ ID NO:1) in which there is a modification that inhibits cleavage between residues 13 and 27 by a serine protease;

(b) a CCL9 analogue that comprises a CCL9 amino acid sequence (SEQ ID NO:4) in which there is a modification that inhibits cleavage between residues 13 and 26 by a serine protease;

(c) a CCL15 analogue that comprises a CCL15 amino acid sequence (SEQ ID NO:9) in which there is a modification that inhibits cleavage between residues 17 and 32 by a serine protease; or (d) a CCL23 analogue that comprises a CCL23 amino acid sequence (SEQ ID NO:16) in which there is a modification that inhibits cleavage between residues 17 and 33 by a serine protease.

Some FPRL1 ligand analogues may include, for example, a CCL23β analogue that comprises a CCL23β amino acid sequence (SEQ ID NO:50) in which there is a modification that inhibits cleavage between residues 17 and 33 by a serine protease.

Another class of inhibitory agents that inhibit the formation of CCR1 ligand fragments include, for example, antibodies that specifically bind CCL6, CCL9, CCL15 or CCL23, or that antagonize the protease that acts on these chemokines. Another class of inhibitory agents that inhibit the formation of FPRL1 ligand fragments include, for example, antibodies that specifically bind CCL23β. Antibodies with these binding specificities can be prepared and identified according the methods provided above.

Other inhibitory agents are small organic molecules that inhibit the protease(s) that cleave CCL6, CCL9, CCL15, CCL23 or CCL23β to form the activated N-truncated chemokines. Examples of such molecules for some of the cleavage proteases described herein include, but are not limited to:

(1) chymase inhibitors: (a) $N^\alpha$-benxocycarbonyl-L-Arg-Glu-Thr-Phe$^P$ phosphonate (see, e.g., Raymond, W. W., et al. (2003) J. Biol. Chem. 278:34517-34524); (b) pyrimidinone derivatives (see, e.g., Akahoshi, F. (2003) Current Pharmaceutical Design 9:1191-1199); (d) chloromethylketone derivatives (see, e.g., Hayashi, Y. et al., Bioorg. Med. Chem. Lett. (2000) 10:199-201); and (e) benzo[b]thiophene-2-sulfonamide derivatives (see, e.g., Masaki, H., et al. (2003) Bioorg. Med. Chem. Lett. 22:4085-8), each of these articles on chymase inhibitors being incorporated herein by reference in its entirety for all purposes;

(2) cathepsin G inhibitors: (a) $\alpha_1$-antichymotrypsin and $\alpha_1$-proteinase inhibitors (see, e.g., Rehault, S. (1999) J. Biol. Chem. 274:13810-13817); and (b) tetrapeptide-nitroanilide derivatives (see, e.g., Polanowska, J. (1998) Biochim. Biophys. Acta. 1386:189-198), (c) 1,3-diazetidine-2,4-diones (see, e.g., Aoyama, Y. et al. (2001) Bioorg. Med. Chem. Lett. 11:1691-4; and (d) 2-amino-3,1-benoxazin-4-ones (see, e.g., Gutschow, M. et al. (2002) Arch. Biochem. Biophys. 402:180-191), each of these articles on cathepsin G inhibitors being incorporated herein by reference in its entirety for all purposes;

(3) elastase inhibitors: (a) peptidyl trifluoromethyl alcohols and ketones (see, e.g. Amour, A., et al. (1998) J. Pharm. Pharmacol. 6:593-600; (b) alpha-ketooxadiazoles (see, e.g., Wieczorek, M. et al. (1999) Arch. Biochem. Biophys. 367:193-201; (c) 1,2,5, thiadiazolidin-3-one 1,1 dioxide derivatives (see, e.g., Kuang, R. et al (2000) Bioorg. Med. Chem. 8:1005-1016; (d) pyrazolooxadiazinone derivatives (see, e.g., Vicentini, C. B., et al. (2001) J. Enzyme Inhib. 16:15-34; and (e) 2-[4-[[(S)-1-[[(S)-2[[(RS)-3,3,3-trifluoro-1-isopropyl-2-oxopropyl]aminocarbonyl]pyrrolidin-1-yl]carbonyl]-2-methylpropyl]aminocarbonyl]benzoylamino]acetate (see, e.g., Shinguh, Y. et al. (1997) Eur. J. Pharmacol. 337:63-71), and (e) peptide analogs (see, e.g., Korkmaz, B., et al. (2004) Am J. Respir. Cell Mol. Biol. 30:801-807), each of these articles on elastase inhibitors being incorporated herein by reference in its entirety for all purposes;

(4) cathepsin G and elastase inhibitors: (a) thrombospondin 1 (see, e.g., Hogg, P. J., et al. (1993) J. Biol. Chem. 268:21811-8; (b) N-oleoyl derivatives of heparin (see, e.g., Baici, A. (1993) Biochem. Pharmacol. 46:1545-9); (c) biphenyl disulfonic acid copolymers (see, e.g., Janusz, M. J. and Hare, M. (1994) Int. J. Immunopharmacol. 16:623-32; (d) peptide derivatives of C-reactive protein (see, e.g., Yavin, E. J., et al. (1996) Int. J. Pept. Protein Res. 48:465-476; and Yavin, E. J. and Fridkin, M. (1998) J. Pept. Res. 51:282-289); (e) serapin derivatives (see, e.g., Cooley, J. (2001) Biochemistry 40:15762-70; and (f) 6-acylamino-2-1(ethylsulfonyl) oxy]-1H-inoindole-1,3-diones (see, e.g., Vagnoni, L. M. et al. Bioorg. Med. Chem. 9:637-45), each of these articles on cathepsin G and elastase inhibitors being incorporated herein by reference in its entirety for all purposes.

2. Activators

Agents that activate the proteases that produce the activated CCR1 and/or FPRL1 ligand fragments can be identified according to the screening methods provided herein. These agents can include agonist antibodies that activate a protease that cleaves CCL6, CCL9, CCL15, CCL23 or CCL23β, for example. The agents can also be other types of polypeptides and small organic molecules, for example.

B. Agents that Modulate the Ability of a CCR1 and/or FPRL1 Ligand Fragment to Bind and/or Activate CCR1 and/or FPRL 1. Inhibitors Some modulatory agents are ones that inhibit the ability of a CCR1 ligand fragment to bind and/or activate CCR1. Some agents of this type are inhibitors that are mimetics of CCL6, CCL9, CCL15, or CCL23, or are mimetics of a CCR1 ligand fragment (e.g., a mimetic of a polypeptide having SEQ ID NO:2-3, 5-8, 10-15, or 17-21), or of another ligand for CCR1 (e.g., CCL3, RANTES, MCP-2, and/or MCP-3). Specific examples of CCR1 inhibitors include, but are not limited to, the small molecule inhibitor discussed in Sbroe, I., et al. (2000) J. Biol. Chem. 275:25985-25992 (see also WO 98/04554) and the CCL25 analog discussed by Escher, S. E., et al. (2004) J. Pept. Res. 63:36-47, which are incorporated herein by reference in their entirety for all purposes.

Additional modulatory agents are ones that inhibit the ability of an FPRL1 ligand fragment to bind and/or activate FPRL1. Some agents of this type are inhibitors that are mimetics of CCL23β, or are mimetics of an FPRL1 ligand fragment (e.g., a mimetic of a polypeptide having SEQ ID NO:22-33 and 45), or of another ligand for FPRL1 (see, e.g., ligands listed in Table 1). Specific examples of FPRL1 inhibitors include, but are not limited to, compound CCX033 (FIG. 13) or the WLWWWW peptide (Bae, Y.-S. et al. (2004) *J Immunol.* 173: 607-614).

Other inhibitors of CCR1 ligand fragment are antibodies that specifically bind a CCR1 ligand fragment. Some antibodies of this type are not cross-reactive with other CCR1 ligands (e.g., full-length CCL6, CCL9, CCL15, CCL23, or CCL3, RANTES, MCP-2, and/or MCP-3), or other chemokines. Still other inhibitors in this general class are antibodies that antagonize CCR1. Other inhibitors of FPRL1 ligand fragment are antibodies that specifically bind an FPRL1 ligand fragment. Some antibodies of this type are not cross-reactive with other FPRL1 ligands (e.g., full-length CCL23β, and/or ligands listed in Table 1). Inhibitors of various structural and chemical types can be identified according to the screening methods provided above. Antibodies can be prepared and selected according to the methods described supra.

2. Activators

Other CCR1 ligand fragment modulatory agents that are provided promote the interaction between CCR1 and a CCR1 ligand fragment. These agents can be polypeptides, small organic molecules, and antibodies that agonize CCR1, for instance. Other FPRL1 ligand fragment modulatory agents that are provided promote the interaction between FPRL1 and a FPRL1 ligand fragment. These agents can be polypeptides, small organic molecules, and antibodies that agonize FPRL1, for instance. Agents of these various types can be identified using the screening methods provided herein.

C. Mimetics

The terms "mimetic" and "peptidomimetic" as used herein refer to a synthetic chemical compound which has substantially the same structural and/or functional characteristics as a CCR1 ligand (e.g., CCL6, CCL9, CCL15, CCL23, CCL3, RANTES, MCP-2, MCP-3, or a CCR1 ligand fragment) and/or FPRL1 ligand. The mimetic can be either entirely composed of synthetic, non-natural analogues of amino acids, or, be a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. Polypeptide mimetic compositions can contain any combination of nonnatural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like.

A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide Backbone Modifications," Marcell Dekker, N.Y.).

A polypeptide can also be characterized as a mimetic by containing all or some non-natural residues in place of naturally occurring amino acid residues. Nonnatural residues are well described in the scientific and patent literature.

The mimetics can also include compositions that contain a structural mimetic residue, particularly a residue that induces or mimics secondary structures, such as a beta turn, beta sheet, alpha helix structures, gamma turns, and the like. For example, substitution of natural amino acid residues with D-amino acids; N-alpha-methyl amino acids; C-alpha-methyl amino acids; or dehydroamino acids within a peptide can induce or stabilize beta turns, gamma turns, beta sheets or alpha helix conformations. Beta turn mimetic structures have been described, e.g., by Nagai (1985) *Tet. Lett.* 26:647-650; Feigl (1986) *J. Amer. Chem. Soc.* 108:181-182; Kahn (1988) *J. Amer. Chem. Soc.* 110:1638-1639; Kemp (1988) *Tet. Lett.* 29:5057-5060; Kahn (1988) *J. Molec. Recognition* 1:75-79. Beta sheet mimetic structures have been described, e.g., by Smith (1992) *J. Amer. Chem. Soc.* 114:10672-10674. For example, a type VI beta turn induced by a cis amide surrogate, 1,5-disubstituted tetrazol, is described by Beusen (1995) *Biopolymers* 36:181-200. Incorporation of achiral omega-amino acid residues to generate polymethylene units as a substitution for amide bonds is described by Banerjee (1996) *Biopolymers* 39:769-777.

The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman et al. (Eds) John Wiley & Sons, Inc., NY. Polypeptides incorporating mimetics can also be made using solid phase synthetic procedures, as described, e.g., by Di Marchi, et al., U.S. Pat. No. 5,422,426. Mimetics of the invention can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) *Mol. Biotechnol.* 9:205-223; Hruby (1997) *Curr. Opin. Chem. Biol.* 1:114-119; Ostergaard (1997) *Mol. Divers.* 3:17-27; Ostresh (1996) *Methods Enzymol.* 267:220-234.

XI. Exemplary Treatment Methods

A. General

The results presented herein demonstrate that the removal of N-terminal regions from the chemokines CCL6, CCL9, CCL15, CCL23, and CCL23β generates CCR1 and FPRL1 ligand fragments that can significantly activate CCR1- and/or FPRL1-mediated biological activities. As such, agents that inhibit the formation of these N-truncated fragments or their interaction with CCR1 and/or FPRL1 can be used to treat various diseases or conditions that are associated with undesired or excessive CCR1 and/or FPRL1 activities (e.g., inflammatory responses), respectively. On the other hand, agents that promote the formation of the N-truncated fragments or their interactions with CCR1 and/or FPRL1 can be used to stimulate CCR1 and/or FPRL1 activity. This can be beneficial, for example, in treating conditions and diseases associated with immunosuppression, for example. Thus, methods of treating inflammatory diseases, as well as immunosuppression are provided.

A. Compositions and Methods for Treating Inflammatory Conditions or Diseases

As just described, agents that either inhibit the protease that generates the CCR1 and/or FPRL1 ligand fragment or that inhibits the ability of the fragment to activate CCR1 and/or FPRL1 can be used in the treatment of various inflammatory diseases. For ease of reference, agents of this type are referred to as "inhibitory agents." Exemplary small molecule inhibitors of the proteases that generate the CCR1 and/or FPRL1 ligand fragments are described above. A variety of antibodies can also be used to inhibit inflammatory diseases based upon the mechanism by which CCR1 and/or FPRL1 are activated. Examples of inhibitory antibodies that can be utilized include: 1) antibodies that antagonize the protease(s) that generate the CCR1 and/or FPRL1 ligand fragment, 2) antibodies that bind to CCL6, CCL9, CCL15, CCL23 or CCL23β and by virtue of their binding prevent these chemokines from being truncated, 3) antibodies that specifically bind a CCR1 and/or FPRL1 ligand fragment and thus prevent it from activating CCR1 and/or FPRL1, and 4) antibodies that antagonize the CCR1 and/or FPRL1 receptors themselves, thus keeping them from interacting with a CCR1 ligand fragment and FPRL1 ligand fragment, respectively. Additional agents of a variety of different types can be identified using the screening methods that are provided. These various agents and antibodies can be formulated as pharmaceuticals as described below for use in therapeutic or prophylactic treatment.

In the context of treating an inflammatory disease an effective regime means that an agent or combination of agents such as just described is administered in sufficient amount and frequency and by an appropriate route to at least detectably prevent, delay, inhibit or reverse development of at least one symptom of an inflammatory disease or condition. An "effective dosage", "pharmacologically acceptable dose", "pharmacologically acceptable amount" in the context of treating an inflammatory disease thus means that a sufficient amount of an inhibitory agent or combination thereof is present to achieve a desired result, e.g., preventing, delaying, inhibiting or reversing a symptom of an inflammatory disorder or the progression of an inflammatory disorder when administered in an appropriate regime.

In prophylactic application for treatment of an inflammatory condition, pharmaceutical compositions or medicants are administered to a subject susceptible to, or otherwise at risk for developing an inflammatory disorder or condition in an amount sufficient to prevent, reduce, or arrest the development of an inflammatory disorder or condition. In therapeutic applications for treatment of inflammatory conditions, compositions or medicants are administered to a patient suspected to develop, or already suffering from an inflammatory disease in an amount sufficient to reverse, arrest, or at least partially arrest, the symptoms of an inflammatory disease or condition. In both prophylactic and therapeutic regimes, pharmaceutical compositions containing inhibitory agents are usually administered in several dosages until a sufficient response has been achieved. However, in both prophylactic and therapeutic regimes, these compositions can administered in a single dosages until a sufficient response has been achieved. Typically, the treatment is monitored and repeated dosages can be given. Furthermore, the treatment regimes can employ similar dosages; routes of administration and frequency of administration to those used in treating other inflammatory-mediated disorders.

The inhibitory agents can be used in the treatment of a variety of inflammatory conditions or diseases that are associated with CCR1 and/or FPRL1. Examples of such conditions and diseases include, but are not limited to, inflammatory or allergic diseases and conditions, including respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); anaphylaxis or hypersensitivity responses, drug allergies (e.g., to penicillin, cephalosporins), insect sting allergies; inflammatory bowel diseases, such as Crohn's disease and ulcerative colitis; spondyloarthropathies; scleroderma; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); autoimmune diseases, such as arthritis (e.g., rheumatoid arthritis, psoriatic arthritis), demyelinating disorders (e.g., multiple sclerosis), systemic lupus erythematosus, myasthenia gravis, juvenile onset diabetes, nephritides such as glomerulonephritis, autoimmune thyroiditis, Behcet's disease; chronic or acute graft rejection (e.g., in transplantation), including allograft rejection or graft-versus-host disease, and graft-associated arteriosclerosis; atherosclerosis; cancers with leukocyte infiltration of the skin or organs; other diseases or conditions (including CCR1-mediated diseases or conditions and FPRL1-mediated diseases and conditions), in which undesirable inflammatory responses are to be inhibited can be treated, including, but not limited to, ischemia/reperfusion injury, certain hematologic malignancies, cytokine-induced toxicity (e.g., septic shock, endotoxic shock), polymyositis, dermatomyositis, and granulomatous diseases including sarcoidosis.

CCR1 also is involved in the trafficking of leukocytes. The evidence indicates that CCR1 plays an important role in the migration of T cell or T cell subset or monocyte migration to certain inflammatory sites. Thus, the inhibitory agents of CCR1 disclosed herein can be used to inhibit (reduce or prevent) T cell or monocyte migration, particularly migration associated with T cell dysfunction, such as autoimmune disease or allergic reactions, or with monocyte-mediated disorders such as atherosclerosis.

Some methods involve monitoring the treated patient to determine if the treatment (prophylactic or therapeutic) has been effective. This usually involves monitoring one or more symptoms associated with an inflammatory disease or condition to determine the treatment has been effective. In the case of therapeutic treatment, monitoring may involve examining the patient to determine if there has been an improvement in symptoms associated with the disease or condition (e.g., reduction in the severity or frequency of the symptom). In the case of prophylactic treatment, monitoring may involve determining if the symptoms have still been kept in check. Symptoms associated with inflammatory diseases are known in the art.

B. Compositions and Methods for Activating a CCR1 and/or FPRL1 Response

1. General

In some instances, it is desired to promote rather than inhibit CCR1 and/or FPRL1 activity. This may be the case, for instance, for immunocompromised individuals and or to promote an immune response to a particular antigen.

Based on its ability to recognize chemotactic peptides, FPRL1 has been proposed to play an important role in host defense against microbial invasion. Mobilization of phagocytes and increased production of bactericidal mediators are necessary for a rapid host response to invading pathogenic microorganism.

FPRL1 has also been considered a player in several devastating diseases, including the HIV-1 infection (Le et al., 2001) and systemic lupus erythematosus (SLE). Furthermore, recent findings that FPRL1 is a functional receptor for at least three forms of amyloidogenic protein and peptide agonists, SAA, Aβ$_{42}$, and PrP106-126, indicate that FPRL1 may play a significant role in several disease states, including Alzheimer's disease (AD) and prion disease such as Creutzfeldt-Jakob disease (CJD). Although the causes of AD and prion disease are unknown, the identification of FPRL1 as a functional receptor for Aβ$_{42}$, and the prion protein fragment PrP106-126 nevertheless provides a molecular link in the chain of proinflammatory responses observed in AD and prion diseases. For example, the activation of FPRL1 may help direct the migration and accumulation of mononuclear phagocytes to sites containing elevated levels of these chemotactic agonists. The infiltrating phagocytes may ingest amyloidogenic proteins and fragments through internalization of the ligand-FPRL1 complex.

A variety of agents that promote the activity of CCR1 ("CCR1 activating agent") and/or FPRL1 ("FPRL1 activating agent") can be used. One class of agents that can be utilized include the CCR1 and/or FPRL1 ligand fragments themselves. Other classes of agents include, but are not limited to, 1) agents identified by the screening methods, for instance, that agonize the protease(s) that generate the CCR1 ligand fragments and or FPRL1 ligand fragments, and 2) agents that agonize CCR1 and/or FPRL1, particularly its ability to bind a CCR1 ligand fragment and/or FPRL1 ligand fragment. Specific examples include agonists antibodies that agonize a protease that truncates a chemokine to form a CCR1 ligand fragment and/or FPRL1 ligand fragment, and agonists antibodies that agonize CCR1 and/or FPRL1 itself. These activating agents can be formulated in a variety of pharmaceutical compositions as described below.

In the context of treating a disease or condition of an immunosuppressed individual an effective regime means that an activating agent or combination of activating agents such as just described is/are administered in a sufficient amount and frequency and by an appropriate route to at least detectably prevent, delay, inhibit or reverse development of at least one symptom of an immunosuppressed disease or condition. Thus, an "effective dosage", "pharmacologically acceptable dose", "pharmacologically acceptable amount" in the context of treating an immunosuppressed disease or condition thus means that a sufficient amount of an activating agent or combination thereof is present to achieve a desired result, e.g., preventing, delaying, inhibiting or reversing a symptom of an immunosuppressed disorder or the progression of an immunosuppressed disorder when administered in an appropriate regime.

In prophylactic application for treatment of an immunosuppressed condition, pharmaceutical compositions or medicants are administered to a subject susceptible to, or otherwise at risk for developing an immunosuppressed disorder or condition in an amount sufficient to prevent, reduce, or arrest the development of an immunosuppressed disorder or condition. In therapeutic applications for treatment of immunosuppressed conditions, compositions or medicants are administered to a patient suspected to develop, or already suffering from an immunosuppressed disease in an amount sufficient to reverse, arrest, or at least partially arrest, the symptoms of an immunosuppressed disease or condition. In both prophylactic and therapeutic regimes, pharmaceutical compositions containing activating agents are usually administered in several dosages until a sufficient response has been achieved. However, in both prophylactic and therapeutic regimes, these compositions can be administered in a single dosages until a sufficient response has been achieved. Typically, the treatment is monitored and repeated dosages can be given. Furthermore, the treatment regimes can employ similar dosages; routes of administration and frequency of administration to those used in treating other inflammatory-mediated disorders.

2. Treatment of Immunosuppression

Exemplary conditions or diseases that can be treated with such activating agents include, but are not limited to: immunosuppression, such as that in individuals with immunodeficiency syndromes such as AIDS; individuals undergoing radiation therapy, chemotherapy, therapy for autoimmune disease or other drug therapy (e.g., corticosteroid therapy), which causes immunosuppression; and immunosuppression due congenital deficiency in receptor function or other causes.

The treatment (either prophylactic or therapeutic) of individuals having an immunosuppressed condition or diseases can be monitored with time to assess the efficacy of the treatment. This typically involves monitoring whether one or more symptoms associated with the disease or disorder has been ameliorated or at least kept from increasing in severity or frequency in the case of therapeutic treatment. In prophylactic methods, the individual being treated is monitored to ensure that a symptom of the disease or condition has not developed.

XII. Vaccine Compositions

Certain activating agents can also be used in combination with a vaccine to promote an immune response to a desired antigen. As noted above, CCR1 plays an important role in leukocyte trafficking. Thus, by introducing a CCR1 activating agent (e.g., a CCR1 ligand fragment) as part of the process of administering a vaccine, the activating agent can promote an immune response to the antigen included in the vaccine. The CCR1 activating agent can be included as part of the vaccine (i.e., be included with the antigen) or can be introduced separately from the antigen. If the CCR1 activating agent is a polypeptide (e.g., a CCR1 ligand fragment), then the polypeptide itself can be administered or, alternatively, a nucleic acid encoding the polypeptide can be administered in a form that can be expressed in the recipient.

In another embodiment, an FPRL1 activating agent (e.g., an FPRL1 ligand fragment) may be introduced as part of the process of administering a vaccine. The FPRL1 activating agent may be included as part of the vaccine (i.e., be included with the antigen) or can be introduced separately from the antigen. If the FPRL1 activating agent is a polypeptide (e.g., a FPRL1 ligand fragment), then the polypeptide itself may be administered or, alternatively, a nucleic acid encoding the polypeptide may be administered in a form that can be expressed in the recipient.

Thus, some compositions that are provided contain one or more CCR1 activating agent as just described (e.g., a CCR1 ligand fragment). In another embodiment, the compositions that are provided may contain one or more FPRL1 activating agents also as described (e.g., an FPRL1 ligand fragment). When the CCR1 and/or FPRL1 activating agent is a polypeptide, it typically is an isolated or recombinant polynucleotide or polypeptide. The CCR1 and/or FPRL1 activating agent(s) in some compositions is/are the predominant species (i.e., greater than about 50%, more often greater than about 80%, 90% or 95% by weight of the total of the members of the class of molecule in the composition) of its class (e.g., polypeptide, polynucleotide) in the composition. The CCR1 and/or FPRL1 activating agent in some compositions is biologically pure.

A composition containing a CCR1 and/or FPRL1 activating agent may additionally contain an excipient or carrier, such as described infra. Certain compositions include one or more antigens (i.e., the antigen to which it is desired to induce or enhance an immune response). Some compositions containing a CCR1 and/or FPRL1 activating agent may also contain a conventional adjuvant. Conventional adjuvants typically convert soluble protein antigens into particulate material and often include bacteria or bacterial products. Exemplary conventional adjuvants include Freund's Incomplete Adjuvant, Freund's Complete Adjuvant, Merck Adjuvant 65, AS-2, alum, aluminum phosphate, mineral gels such as aluminum hydroxide, and surface active substances such as lysolecithin, pluronic polyols, polyanions, peptides, oil emulsions, keyhole limpet hemocyanin, and dinitrophenol.

Some compositions contain an antigen or an immunogen. An antigen is a molecule that reacts with an antibody. In some embodiments the antigen is an immunogen that can trigger an immune response in a species (e.g., a mammal, particularly a human). The antigen may be linked to conventional protein carriers or other agents that promote the generation of antibodies.

Typically, an antigen is a peptide, a polypeptide, chemical compound, microbial pathogen, bacteria (e.g., live, attenuated, or inactivated), a virus (including inactivated virus particles, modified live viral particles, and recombinant virus particles), a recombinant cell, glycoproteins, lipoproteins, glycopeptides, lipopeptides, toxoids, carbohydrates, tumor-specific antigens, and other immunogenic components of pathogens. Certain compositions are mixtures of two or more antigens.

Exemplary antigens or vaccine components of the invention include antigens derived from microbial pathogens such as bacteria [e.g., Pertussis (*Bordetella pertussis*, inactivated whole organism); Cholera (*Vibrio cholerae*, whole killed organism); Meningitis (*Neisseria meningitidis*, polysaccharide from organism); Lyme Disease (*Borrelia burgdorferi*, lipoprotein OspA); *Haemophilus B* (*Haemophilus* influenza B polysaccharide, *Tetanus conjugate* or OmpC); Pneumonia (*Streptococcs pneumoniae* capsular polysaccharide) Typhoid (*Salmonella typhi* polysaccharide vaccine, killed whole organism)], viruses including inactivated virus particles, modified live viral particles, and recombinant virus particles to Influenza virus; Hepatitis A; Hepatitis B; Measles; Rubella virus; Mumps; Rabies; Poliovirus; Japanese Encephalitis virus; Rotavirus; Varicella], Diphtheria *Corynebacterium diphtheriae*) and Tetanus (*Clostridium tetani*).

Compositions containing an antigen can be used to provide protection from exogenous foreign infectious pathogenic agents (such as bacteria, virus, and the like) prior to expected or possible exposure. The methods and compositions can also be used to provide therapeutic effects against exogenous foreign pathogens to which an individual has been exposed or to an individual displaying symptoms of exposure.

The compositions and methods can be used to treat cancers, including, but not limited to, melanomas, lung cancers, thyroid carcinomas, breast cancers, renal cell carcinomas, squamous cell carcinomas, brain tumors and skin cancers. In one embodiment, the antigen is a tumor associated antigen (tumor specific antigen). Tumor antigens are molecules, especially cell surface proteins that are differentially expressed in tumor cells relative to non-tumor tissues (e.g., telomerase).

For prophylactic use, compositions containing the CCR1 and/or FPRL1 activating agent(s) may be administered (e.g., in conjunction with antigens) to a subject susceptible to or otherwise at risk of a disease, e.g. a tumor, cancer, infection, and the like. For therapeutic use, compositions containing the CCR1 and/or FPRL1 activating agent are administered (e.g., in conjunction with antigens) to a subject once a disease, e.g. a tumor, cancer, infection, and the like, is detected or diagnosed, or after surgical removal, e.g. of tumors.

In some instances, the CCR1 and/or FPRL1 activating agent, the antigen, or both are delivered as DNA such that the polypeptides are generated in situ. In one embodiment, the DNA is "naked," as described, for example, in Ulmer et al., *Science* 259:1745-1749, 1993 and reviewed by Cohen, 1993, *Science* 259:1691-1692. The uptake of naked DNA may be increased by coating the DNA onto a carrier, e.g. biodegradable beads, which is efficiently transported into the cells. In such vaccines, the DNA may be present within any of a variety of delivery systems known to those of ordinary skill in the art, including nucleic acid expression systems, bacterial and viral expression systems. Techniques for incorporating DNA into such expression systems are well known to those of ordinary skill in the art. See, e.g., WO90/11092, WO93/24640, WO 93/17706, and U.S. Pat. No. 5,736,524.

XIII. Pharmaceutical Compositions

A. Composition

Compounds identified by the screening methods described above, ligand analogues that include a modification that prevents cleavage in the N-terminus, and antibodies of the type described can serve as the active ingredient in pharmaceutical compositions formulated for the treatment of various neurological disorders including stroke. The compositions can also include various other agents to enhance delivery and efficacy. For instance, compositions can include agents capable of increasing the permeability of the blood/brain barrier. Other agents that can be coadministered include anticoagulants and blood thinners. The compositions can also include various agents to enhance delivery and stability of the active ingredients.

Thus, for example, the compositions can also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide (e.g., a CCR1 and/or FPRL1 ligand fragment polypeptide), the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249:1527-1533 (1990).

B. Dosage

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with little or no toxicity. The dosage can vary within this range depending upon the dosage form employed and the route of administration utilized.

3. Administration

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The active ingredient, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen.

Suitable formulations for rectal administration include, for example, suppositories, which consist of the packaged active ingredient with a suppository base. Suitable suppository bases include natural or synthetic triglycerides or paraffin hydrocarbons. In addition, it is also possible to use gelatin rectal capsules which consist of a combination of the packaged active ingredient with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

XIV. Grafts, Stents and Stent Grafts

Compounds identified by the screening methods described above, ligand analogues that include a modification that prevents cleavage in the N-terminus, antibodies of the type described, and pharmaceutical compositions comprising them (collectively called "inhibitory agents") may be formulated for depositing into a medical device, which may include any of variety of conventional grafts, stents, including stent grafts, catheters, balloons, baskets or other device that can be deployed or permanently implanted within a body lumen. CCR1 bearing monocytes, for instance, may play a role in schlerosis, rejection and tissue damage at sites of arterial implants. Thus, by introducing a CCR1 inhibitory agent, such as a protease inhibitor as described above, as part of the device, the inhibitory agent can inhibit proteases at the sites of implantation and therefore might be expected to prevent and/or ameliorate the disease. As a particular example, it would be desirable to have devices and methods which can deliver an inhibitory agent to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 08/746,404, filed Nov. 8, 1996 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly(lactide-co-glycolide) (PLLA/PGA), poly(hydroxybutyrate), poly(hydroxybutyrate-co-valerate), polydioxanone, poly-orthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable polymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. patent application 20040243225A1, the entire disclosure of which is incorporated by reference in its entirety.

Moreover, as described for example in U.S. Pat. No. 6,770,729, which is incorporated herein by reference in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

The following examples are provided solely to illustrate in greater detail certain aspects of the invention and are not to be construed to limit the scope of the invention.

EXAMPLES

Example 1

Proteolytic Activation of CCR1 Ligands and their Activities

I. Material and Methods

Chemokines, Proteases and Cells. Recombinant CCL6/C10, CCL9/MIP-1γ, CCL15/MIP-1δ (92aa), CCL15Δ24/LKN-1 (68aa), CCL23/CKβ8 (22-120) and CCL23Δ24/MPIF-1 (46-120) were purchased from R&D Systems (Minneapolis, Minn.). Purified enzymes Asp-N, elastase and cathepsin G were purchased from Sigma (St. Louis, Mo.). Recombinant human chymase was a generous gift from Norman Schechter (Univ. of Pennsylvania, Philadelphia, Pa.). Human synovial fluids from inflamed knee joints were either donated by a person in our lab or purchased from Bioreclamation (Hicksville, N.Y.). Human neutrophils were purified from healthy donors by sedimentation in DEAE-dextran and lysis of contaminating erythrocytes in PharmLyse (BD Biosciences, San Diego, Calif.). The neutrophils were cultured in serum-free RPMI-1640 medium (HyClone, Logan, Utah) containing 0.1 μg/ml phorbol myristic acid (PMA) and 1 μg/ml ionomycin (both from Sigma, St. Louis, Mo.) for 6 hours at 37° C. in a humidified incubator containing 5% $CO_2$. The conditioned medium ("PMN sup") was collected as the supernatant after low-speed centrifugation of the cultures to remove the cells.

Human monocytes were obtained from buffy coats purchased from the Stanford Blood Bank (Palo Alto, Calif.) by sedimentation on Ficoll-Paque (Amersham, Piscataway, N.J.) and selection with anti-CD14 magnetic beads (Miltenyi, Auburn, Calif.) according to the manufacturers' instructions. For generation of dendritic cells, monocytes were cultured for 6 days in RPMI-1640 medium containing 10% FBS (HyClone, Logan, Utah). On days 0, 2 and 4, GM-CSF and IL-4 (both purchased from R&D Systems, Minneapolis, Minn.) were added to the cultures at 1000 WHO unit/ml each. The cells were confirmed to be $CD14^-CD1a^+$ immature DC by FACS staining on day 6.

Chemokine Digestion and SDS-PAGE. Typically, 10 μg of each C6* chemokine was mixed with 0.1-0.4 μg of each enzyme, 4 μl of synovial fluid or 20 μl PMN sup in a 40 μl volume reaction containing 100 mM Tris-HCl pH 7.8 and 10 mM $CaCl_2$. The mixtures were incubated at 37° C. up to 24 hours, then frozen for later analysis. For visualization of chemokine cleavage fragments, 8 μl of each digest was mixed with 2 μl of 1 M DTT (Sigma, St. Louis, Mo.) and 12.5 μl Tricine sample buffer (Invitrogen, Carlsbad, Calif.), heated to 90° C. for 3 min, and subjected to denaturing gel electrophoresis on 10-20% acrylamide Tricine mini-gels (Invitrogen, Carlsbad, Calif.) at 125 V for 1 hour. The gels were then rinsed 3×10 min with water, immersed in GelCode Blue reagent (Pierce, Rockford, Ill.) for 1 hour with gentle shaking and destained in water for 2-18 hours. For N-terminal sequencing, cleavage products were electroblotted onto Immobilon-$P^{SQ}$ membranes (Sigma, St. Louis Mo.), stained with GelCode Blue and sequenced by the Stanford PAN (Palo Alto, Calif.) or UC Davis MSF (Davis, Calif.) facilities.

Calcium Mobilization Assay. Cells were loaded for 1 hour with 2 μM indo-1/AM dye (Molecular Probes, Eugene, Oreg.) in culture medium, then washed with 10 ml PBS and resuspended at $10^6$/ml in HBSS containing 1% FBS. Cytosolic calcium responses were determined using a Photon Technology International (Lawrenceville, N.J.) fluorimeter, with excitation at 350 nm and dual emission at 400 and 490 nm. Alternatively, cells were loaded with 5 μg/ml Fluo-4 AM dye (Molecular Probes, Eugene, Oreg.), then washed and analyzed on a Fluorometric Imaging Plate Reader 384 ($FLIPR^{384}$ Molecular Devices, Sunnyvale, Calif.), with 505 nm excitation and 530 nm emission.

Chemotaxis assay. L1.2-CCR1 transfectants, THP-1 cells, human monocytes and human neutrophils were collected by centrifugation and resuspended in HBSS containing 0.1% BSA. Chemotaxis assays were performed in 96-well ChemoTx® microplates (Neuroprobe, Rockville, Md.) as follows. Chemokines were added to the lower wells (final volume 29 μL), and 20 μL of cell suspension ($5 \times 10^6$ cells/mL) was added to the polycarbonate filter (3 μm pore size for neutrophils, 5 μm for other 3 cell types). After incubation at 37° C. in the presence of 5% $CO_2$ for 1 hr (neutrophils), 90 min (monocytes) or 2 h (THP-1 and L1.2-CCR1), cells were removed from the upper surface of the filter by scraping. Cells that migrated into the lower chamber were quantified by using the CyQuant cell proliferation assay kit (Molecular Probes, Eugene, Oreg.) and analyzed with a Tecan (Durham, N.C.) fluorimeter (excitation at 480 nm, emission at 530 nm). Data were analyzed and plotted in arbitrary units of fluorescence using Prism (GraphPad Software, San Diego, Calif.).

ELISA. Serial 10-fold dilutions of human synovial fluids were analyzed for levels of CCL3/MIP-1α and CCL5/RANTES with commercial sandwich ELISA kits (BD Biosciences, San Diego, Calif.) according to the manufacturer's protocol. The fluids were also analyzed for human CCL15/MIP-1δ and CCL23/CKβ8 by sandwich ELISA using antibodies from R&D Systems, Inc. (Minneapolis, Minn.). For specific detection of full-length forms of CCL15/MIP-1δ and CCL23/CKβ8, a capture mAb specific for the N-terminal domains—which are nearly identical in the two chemokines—was employed (anti-CCL23 clone # 69510, a generous gift from Monica Tsang). Polyclonal detector Abs (catalog #s BAF363 and BAF508) were used to identify the captured chemokine as CCL15/MIP-1δ or CCL23/CKβ8. The presence of N-terminally truncated CCL15/MIP-1δ and CCL23/CKβ8 in the fluids was inferred by comparing the full-length chemokine-specific ELISAs described above to ELISAs which detect both full-length and truncated forms of each chemokine. These latter ELISAs employ CCL15/MIP-1δ- or CCL23/CKβ8-specific capture mAbs whose epitopes do not depend on the N-terminal domains (catalog #s MAB363 and MAB371, respectively) and the polyclonal detector Abs noted above. The CCL15/MIP-1δ and CCL23/CKβ8 detected in the fluids were not a factor in the functional analyses of the in vitro digestions, since the synovial fluids were diluted 10-fold in the digestions and the digestions were diluted at least 100-fold in the functional assays.

II. Results

A. CCL15

Recombinant CCL15/MIP-1δ was tested for its ability to be cleaved by proteases and physiological fluids associated with inflammation. The chemokine was incubated for 1 or 18 hr with recombinant mast cell chymase, purified neutrophil cathepsin G, purified neutrophil elastase, activated neutrophil-conditioned media from two donors, or synovial fluid from 10 patients with rheumatoid arthritis or 3 patients with sports-related knee injuries. SDS-PAGE analysis of the digestions indicated that nearly all of the proteases and fluids cleaved CCL15/MIP-1δ, generating truncated forms ~2-3 kDa smaller than the parental chemokine (FIG. 1A and data not shown). The truncated forms exhibited electrophoretic mobilities similar to recombinant CCL15/MIP-1δ lacking the N-terminal 24 residues ("CCL15Δ24/LKN-1"; FIG. 1A). N-terminal sequencing of the truncated forms indicated that the proteases and fluids partially or completely removed the CCL15 N-terminal domain, leaving 3-10 residues upstream of the conserved CC motif (FIG. 1B and FIG. 3A).

To determine if the truncated forms exhibited increased functional activities, the digestions were subjected to several functional assays in vitro. First, the digestions were analyzed for their ability to induce signaling in CCR1$^+$ cells, as measured by changes in cytosolic calcium levels over time. At 10 nM, full-length CCL15/MIP-1δ induced little calcium mobilization in murine L1.2 cells stably expressing human CCR1, while recombinant CCL15Δ24/LKN-1 induced a substantially greater response (FIG. 1C). At 10 nM input chemokine, all of the digestions similarly mobilized a greater amount of calcium than full-length CCL15/MIP-1δ, in some cases even more than CCL15Δ24/LKN-1 (FIGS. 1C and 1D and data not shown). Control digestions lacking CCL15/MIP-1δ did not induce calcium mobilization, indicating that the signaling activity of the digestions derived from the truncated chemokines and not the proteases or fluids themselves (FIGS. 1C and 1D and data not shown).

Figure 1E:
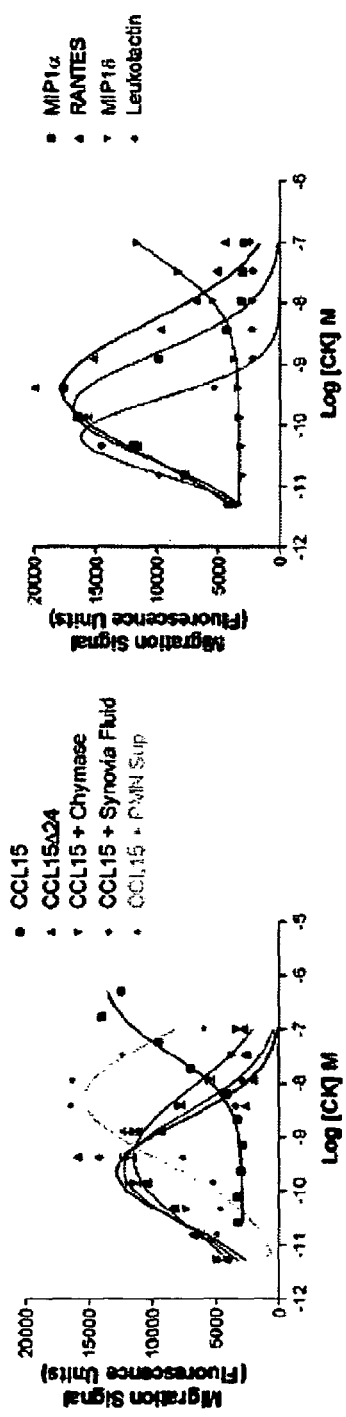

The truncated forms were also analyzed for their abilities to chemoattract CCR1-bearing cells in vitro. Human THP-1 cells were used because of their high migratory potential. Full-length CCL15/MIP-1δ was a relatively weak chemoattractant for THP-1 cells (EC$_{50}$ 50 nM) while CCL15Δ24/LKN-1 was much more potent (EC$_{50}$ 60 pM; FIG. 1E). The digestions were similarly potent, exhibiting EC$_{50}$s of 50 pM (chymase), 60 pM (synovial fluid) and 250 pM (PMN sup #1; FIG. 1E, left panel). Control digestions lacking CCL15/MIP-1δ did not induce THP-1 migration, indicating that the chemotactic activity of the digestions was due to the truncated chemokines and not the proteases or fluids themselves (data not shown). Chemotaxis assays using CCL3/MIP-1α or CCL5/RANTES indicated that these traditional CCR1 ligands were approximately 3-fold less potent than CCL15Δ24/LKN-1 (FIG. 1E, right panel).

Figure 2A:
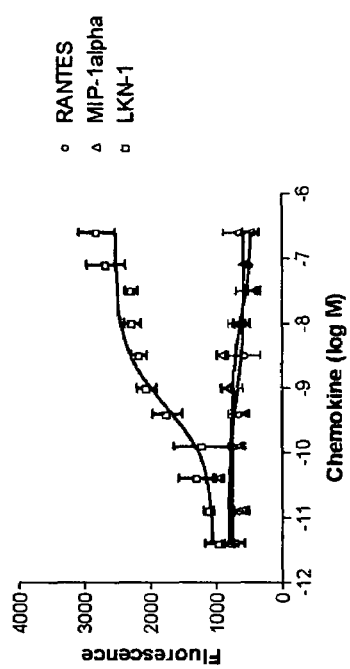
FIG. 2. Human neutrophils respond to CCL15/MIP-1δ after truncation by pro-inflammatory proteases and fluids, but not to CCL3/MIP-1α or CCL5/RANTES. Abbreviations are as indicated in FIG. 1. A, calcium mobilization assay. Freshly-isolated human neutrophils were loaded with a calcium-sensitive fluorescent dye and exposed to dilutions of CCL15Δ24/LKN-1, CCL3/MIP-1α or CCL5/RANTES. Changes in fluorescence were measured over time, and peak fluorescence levels were plotted vs chemokine concentration. B, calcium mobilization assay. Freshly-isolated human neutrophils were loaded with a calcium-sensitive fluorescent dye and exposed to CCL15Δ24/LKN-1 or the CCL15/MIP-1δ digestions at 30 nM (left panel) or 50 nM (right panel). Changes in fluorescence are depicted over time, and control digestions lacking chemokine are shown for comparison.
Figure 2B:
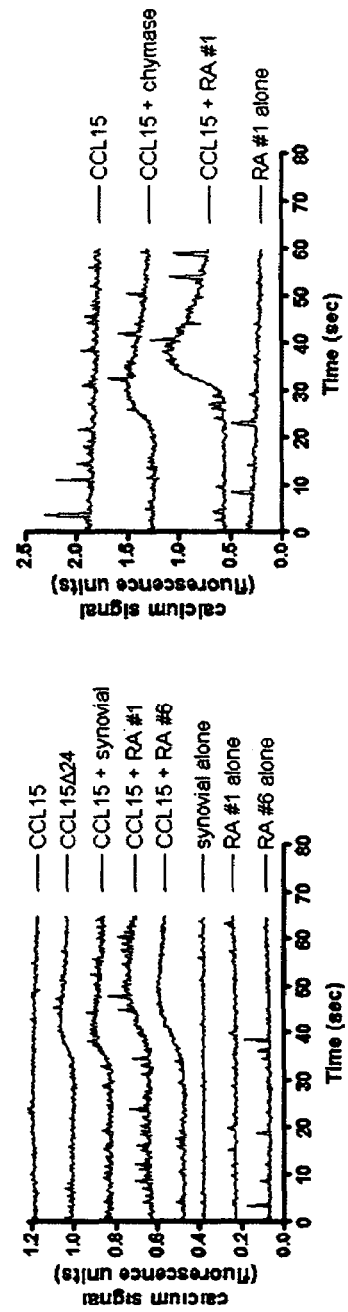

Since the pro-inflammatory proteases and fluids rendered CCL15/MIP-1δ even more potent than CCL3/MIP-1α and CCL5/RANTES, we tested the ability of the CCL15/MIP-1δ digestions to function on human neutrophils, which respond to CCL15Δ24/LKN-1 but not to CCL3/MIP-1α or CCL5/RANTES (FIG. 2A). At 30-50 nM, the CCL15/MIP-1δ digestions induced calcium mobilization in neutrophils, in some cases as much as that induced by CCL15Δ24/LKN-1 (FIG. 2B).

B. CCL6, CCL9 and CCL23

Figure 4:
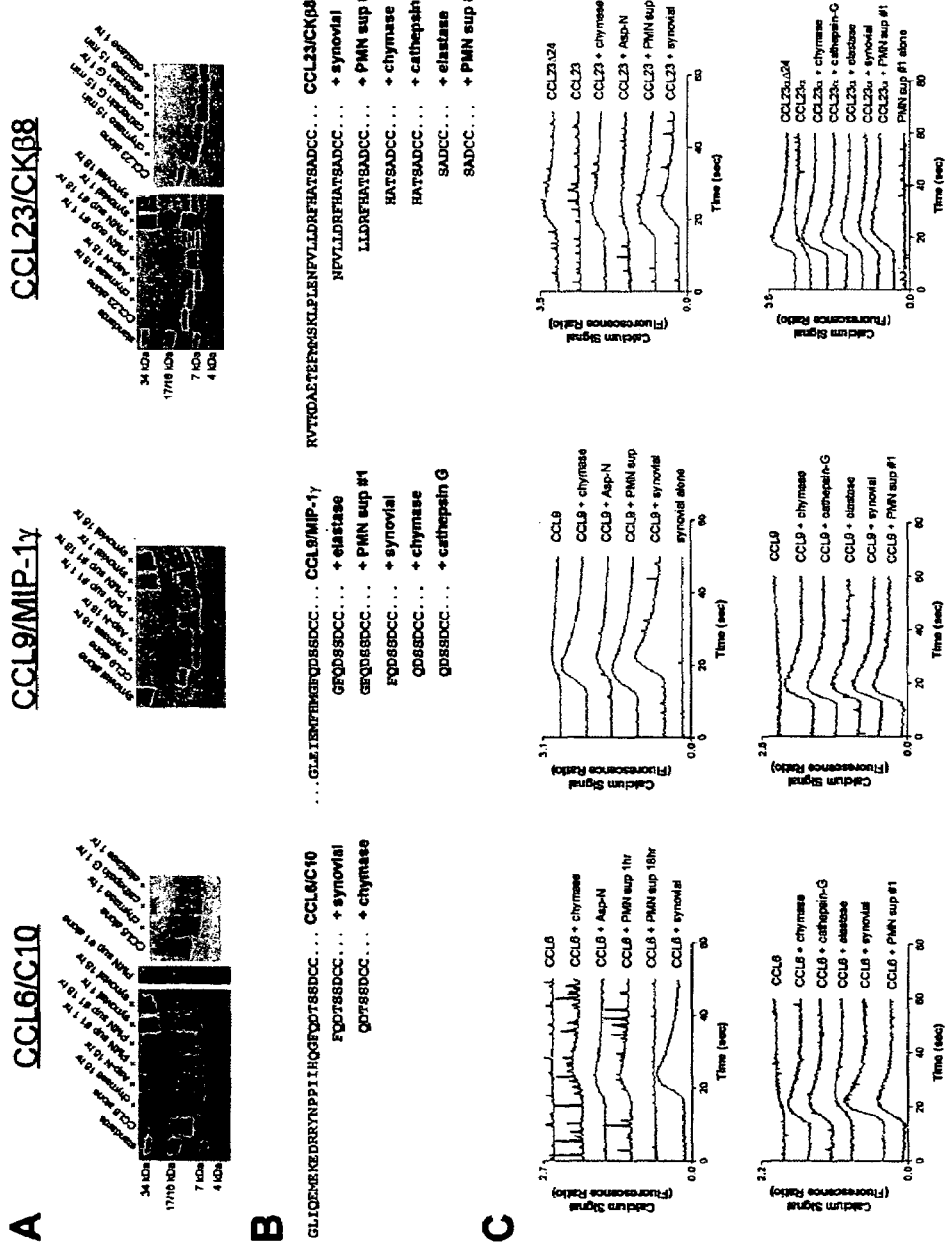
FIG. 4. Pro-inflammatory proteases and fluids digest the C6* chemokines CCL6/C10, CCL9/MIP-1γ and CCL23/CKβ8. Each chemokine were treated for 15 min, 1 hr or 18 hr with the proteases and fluids described in the legend to FIG. 1. Abbreviations are also as indicated in FIG. 1. A, analysis by SDS-PAGE. Portions of the digestions were subjected to SDS-PAGE, with subsequent Coomassie Blue staining of the gels. Digestions lacking chemokine ("PMN sup alone", "synovial alone"—same dilutions as the digestions containing chemokine) are shown for comparison. B, N-terminal sequence analysis. N-terminal sequences of some of the truncated forms were determined by N-terminal Edman sequencing after SDS-PAGE and electroblotting. C, calcium mobilization assay. Murine L1.2 cells expressing human CCR1 were loaded with a calcium-sensitive fluorescent dye, then treated with a portion of the digestions and analyzed for fluorescence over time. Digestions lacking chemokine ("PMN sup alone", "synovial alone"—same dilutions as the digestions containing chemokine) and recombinant CCL23Δ24/MPIF-1 are shown for comparison. D, E, chemotaxis assay. Dilutions of digestions were tested for the ability to chemoattract L1.2-CCR1 (D) or THP-1 cells (E) in vitro. L1.2-CCR1 cells were exposed to selected CCL6/C10, CCL9/MIP-1γ or no-chemokine digestions at 0.5 nM (white bars), 5 nM (grey bars) or 50 nM (black bars) for 2 hr, after which the relative amounts of migration were measured by DNA content. THP-1 cells were exposed to multiple dilutions of the CCL23/CKβ8 digestions for 2 hr, after which the migrated cells were solubilized and quantified by DNA content.

Since CCL15/MIP-1δ was consistently truncated and activated by the pro-inflammatory proteases and fluids, the other C6* chemokines—CCL6/C10/MRP-1, CCL9/MIP-1γ/MRP-2 and CCL23/CKβ8/MPIF-1—were similarly tested for truncation and activation. The three other C6* chemokines were truncated by ~2-4 kDa by the proteases and fluids (FIG. 4A), and N-terminal sequencing of the truncated forms indicated that their N-terminal domains were mostly or completely removed (FIG. 4B). The sites of cleavage and the sequences of the resulting N-truncated fragments are indicated in FIGS. 3A and 3B. At 10 nM input chemokine, the digestions were uniformly active for calcium mobilization in L1.2-CCR1 cells, whereas the undigested parental chemokines were either not active or weakly active (FIG. 4C, top panels). Control digestions lacking the chemokines did not induce calcium mobilization, as seen before (FIG. 1C).

Figure 4E:
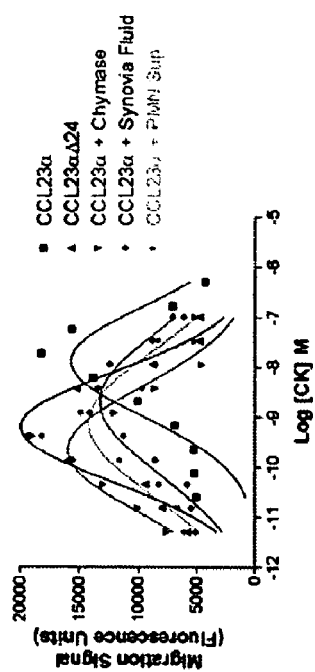
Figure 4D:
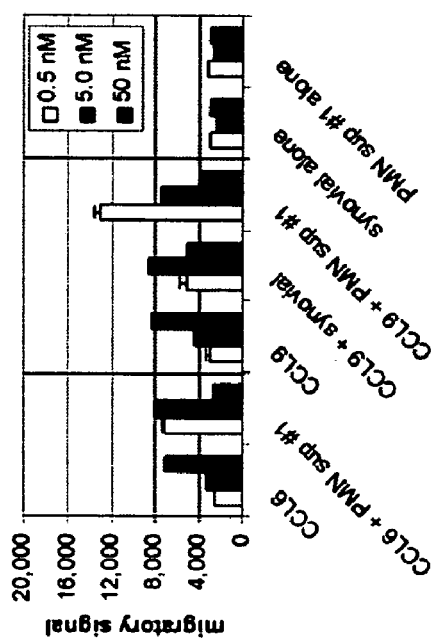

Three-point titrations of selected CCL6/C10 and CCL9/MIP-1γ digestions in the L1.2-CCR1 chemotaxis assay indicated that the truncated forms stimulated chemotaxis with greater potency than the full-length chemokines (FIG. 4D). A more extensive titration of the CCL23/CKβ8 digestions on THP-1 cells indicated that chymase decreased the EC$_{50}$ 50-fold, from 2.5 nM to 50 pM, while PMN sup #1 decreased the EC$_{50}$ to 150 pM and synovial fluid decreased the EC$_{50}$ to 250 pM (FIG. 4E). Recombinant CCL23/CKβ8 lacking the N-terminal 24 residues ("CCL23Δ24/MPIF-1") exhibited an EC$_{50}$ of 90 pM. As before, control digestions lacking CCL6, CCL9 and CCL23 did not chemoattract L1.2-CCR1 or THP-1 cells, indicating that the chemotactic activity of the chemokine digestions was due to the truncated chemokines and not the proteases or fluids themselves (FIG. 4D and data not shown).

Figure 5A:
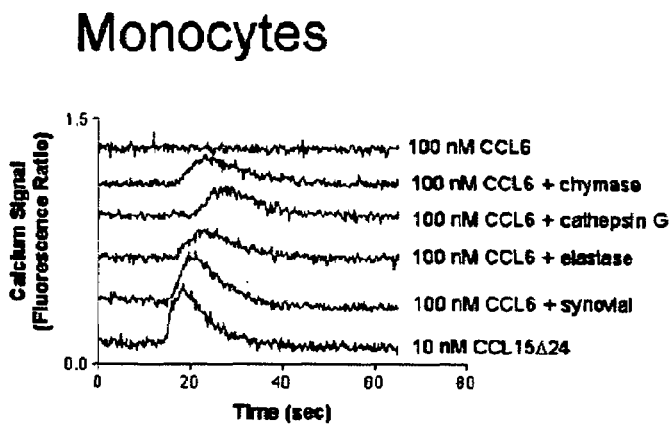
FIG. 5. Human monocytes and dendritic cells respond to CCL6/C10 after truncation by pro-inflammatory proteases and fluids. Abbreviations are as indicated in FIG. 1. A, calcium mobilization assay. Freshly-isolated human monocytes were loaded with a calcium-sensitive fluorescent dye, then exposed to the CCL6/C10 digestions at 100 nM and analyzed for fluorescence over time. Recombinant CCL15Δ24/LKN-1 is shown for comparison. B, chemotaxis assay. Freshly-isolated monocytes were exposed to the CCL6/C10 digestions at 2 (white bars), 20 (grey bars) or 200 (black bars) nM for 90 min, after which the migrated cells were solubilized and quantified by DNA content. C, calcium mobilization assay. Immature monocyte-derived dendritic cells were loaded with a calcium-sensitive fluorescent dye, then exposed to the CCL6/C10 digestions at 25 nM and analyzed for fluorescence over time. Recombinant CCL15Δ24/LKN-1 is shown for comparison.
Figure 5B:
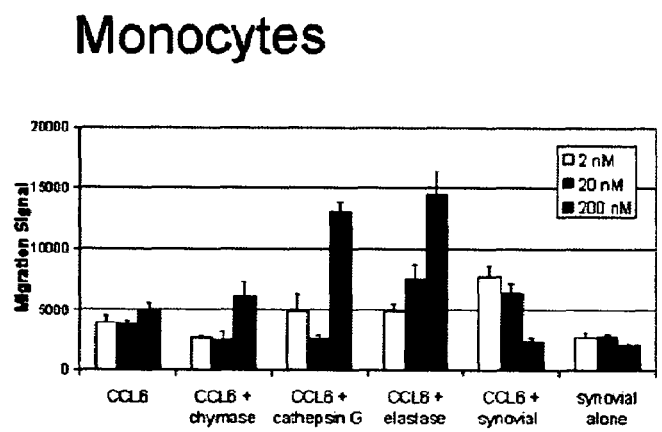
Figure 5C:
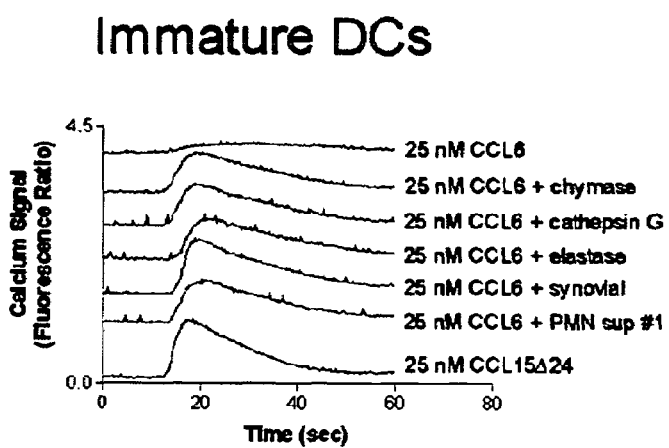

To determine whether proteolytic cleavage increased chemokine potency in primary human cells, CCL6/C10 was chosen because, of the 4 C6* chemokines, it is the least potent on human monocytes and monocyte-derived immature dendritic cells (data not shown). CCL6/C10, which was unable to induce calcium mobilization in monocytes even at 100 nM, mobilized calcium at that concentration after digestion with chymase, cathepsin G, elastase or synovial fluid (FIG. 5A). CCL6/C10 also stimulated chemotaxis of monocytes at 200 nM after digestion with chymase, cathepsin G or elastase (FIG. 5B). Digestion of CCL6/C10 with synovial fluid #1 resulted in a dramatic increase in potency, with the most migration occurring at 2 nM (FIG. 5B). CCL6/C10 digestions with chymase, cathepsin G, elastase, synovial fluid or PMN sup #1 were also more efficacious than full-length CCL6/C10 for calcium mobilization in immature dendritic cells derived from monocytes (FIG. 5C).

To determine whether the chemokine-activating ability of the pro-inflammatory proteases and fluids was specific for the C6* chemokines, 3 non-C6* chemokine—CCL3/MIP-1α, CCL5/RANTES and CCL25/TECK—were tested with a subset of the proteases and fluids. CCL3/MIP-1α and CCL5/RANTES were not visibly truncated by the two RA synovial fluids analyzed, while chymase initially truncated a portion of these two chemokines by ~2 kDa (FIG. 6A). However, in a THP-1 chemotaxis assay, each chemokine was at least 10-fold less potent after digestion with either RA fluid or with chymase (FIG. 6B). CCL25/TECK, which has the longest C-terminal tail of the β-chemokines, was rapidly cleaved and inactivated for signaling through CCR9 by all proteases and fluids tested (FIGS. 6A and 6C).

C. In Vivo Detection of Truncated Forms

To assess whether C6* chemokines with N-terminal truncations exist in vivo, the panel of 13 synovial fluids was analyzed by sandwich ELISA. For CCL15/MIP-1δ, an assay capable of recognizing full-length but not N-terminally truncated CCL15/MIP-1δ detected protein in none of the 13 synovial fluids; comparison to a standard curve of CCL15/MIP-1δ defined the limit of detection as 90 pM. In contrast, an assay capable of recognizing both full-length and N-terminally truncated CCL15/MIP-1δ detected protein in all 13 fluids; comparison to a standard curve of CCL15Δ24/LKN-1 indicated that the synovial fluids contained 130-900 pM (limit of quantitation 120 pM). Similarly, an assay recognizing full-length but not N-terminally truncated CCL23/CKβ8 detected protein in none of the 13 synovial fluids; comparison to a standard curve of CCL23/CKβ8 defined the limit of detection as 80 pM. An assay capable of recognizing both full-length and N-terminally truncated CCL23/CKβ8 detected protein in 12 of the 13 fluids. Comparison to a standard curve of CCL23Δ24/MPIF-1 indicated that these 12 synovial fluids contained protein concentrations between the limits of detection (230 pM) and quantitation (1700 pM). However, the possibility that the synovial fluids contained small amounts of full-length CCL15/MIP-1δ (up to 90 pM) and/or CCL23/CKβ8 (up to 80 pM) makes it difficult to quantify precisely the levels of N-terminally truncated CCL15 or CCL23. In contrast, commercial ELISA kits specific for human CCL3/MIP-1α and CCL5/RANTES detected only low levels (20-120 pM) of chemokine in two (CCL3/MIP-1α) or six (CCL5/RANTES) of seven synovial fluids analyzed.

III. Discussion

This study demonstrated that the N-terminal domain unique to the C6* chemokines—murine CCL6/C10 and CCL9/MIP-1γ, human CCL15/MIP-1δ and CCL23/CKβ8—is readily removed by proteases associated with human inflammatory responses. Recombinant mast cell chymase, purified neutrophil cathepsin G, purified neutrophil elastase, conditioned medium from activated neutrophils, and synovial fluids from patients with rheumatoid arthritis or sports-related knee injuries were all observed to fully or partially remove the N-terminal domain of each of the 4 C6* chemokines in vitro. The site of cleavage varied from 3 to 14 residues upstream of the dicysteine motif. Each truncated chemokine was relatively resistant to further digestion by the proteases, despite the presence of additional potential cleavage sites. Presumably, these additional sites are inaccessible to the proteases. In only one instance (CCL6/C10 with neutrophil-conditioned medium #1) did we observe complete proteolysis of the chemokine within 24 hr, which occurred only after the initial N-terminal truncation.

As a result of proteolytic removal of the N-terminal domain, C6* chemokines became substantially more potent ligands for CCR1, as measured by calcium mobilization and cell migration in vitro. Cleavage of CCL15/MIP-1δ by chymase or synovial fluid increased chemokine potency in THP-1 cell migration approximately 1000-fold, to an $EC_{50}$ of 50-60 pM—similar to recombinant CCL15Δ24/LKN-1 lacking the N-terminal domain altogether. Cleavage of CCL23/CKβ8 by chymase increased that chemokine's potency to 50 pM as well. These potencies are well above those of the more conventional CCR1 ligands, CCL3/MIP-1α and CCL5/RANTES, which in uncleaved forms exhibited $EC_{50}$s of 500 pM. Protease incubation with CCL3/MIP-1α and CCL5/RANTES resulted in decreases in functional potency, presumably since neither of these two chemokines possesses an inhibitory N-terminal domain. The N-terminally truncated forms of CCL15/MIP-1δ and CCL23/CKβ8 are the most potent CCR1 ligands known.

Because digestion mixtures, not purified cleavage fragments, were applied to the cells in our studies, it is possible that the proteases altered the cells, rendering them more responsive to the chemokines. However, since calcium mobilization was observed within 5 seconds after addition of the digestions, any such modification of the cells would have had to occur very rapidly. Moreover, as recombinant chemokines CCL15Δ24 and CCL23Δ24 lacking N-terminal domains exhibited similar potency in the absence of proteases, it is unlikely that protease-mediated cellular changes contributed significantly to the results.

Due to their potency, the N-terminally truncated forms of CCL15/MIP-1δ and CCL23/CKβ8 were functional on human neutrophils, which are poorly responsive to CCL3/MIP-1α or CCL5/RANTES in vitro. Specificity of CCR1 utilization on the neutrophils was confirmed by pre-treating the cells with high concentrations of CCL3/MIP-1α.

The results shown here are of interest because proteolytic removal of N-terminal residues has been shown to inactivate CC and CXC chemokines (McQuibban, G. A. et al, 2000. *Science* 289:1202-1206; McQuibban, G. A. et al, 2001. *J Biol Chem* 276:43503-43508; Delgado, M. B. et al, 2001. *Eur J Immunol* 31:699-707; Proost, P. et al, 2001. *Blood* 98:3554-3561; Ludwig, A. et al, 2002. *J Leukoc Biol* 72:183-191; McQuibban, G. A. et al, 2002. *Blood* 100:1160-1167; Christopherson, K. W., 2nd. et al, 2002. *J Immunol* 169:7000-7008; Crump, M. P. et al, 1997. *EMBO J* 16:6996-7007; Weber, M. et al, 1996. *J Exp Med* 183:681-685; Struyf, S. et al, 1998. *Eur J Immunol* 28:1262-1271; Oravecz, T. et al, 1997. *J Exp Med* 186:1865-1872). In many cases, these truncated chemokines were still able to bind to their receptors and, as a result, functioned as antagonists in chemotaxis assays in vitro and exhibited anti-inflammatory properties in vivo.

It is interesting that, in the absence of exogenously-added chemokines, certain pro-inflammatory proteases have been shown to induce leukocyte chemotaxis in vitro and in vivo. Injection of human chymase or tryptase into guinea pig skin or mouse peritoneal cavity resulted in substantial neutrophil and eosinophil recruitment within 3 hours (He, S. et al, 1997. *J Immunol* 159:6216-6225; He, S. et al, 1998. *Br J Pharmacol* 125:1491-1500). Injection of human chymase into mouse ear also resulted in polymorphonuclear cell recruitment (Tomimori, Y. et al, 2002. *Biochem Pharmacol* 64:1187; Tomimori, Y. et al, 2002. *Lab Invest* 82:789-794). Moreover, a chymase inhibitor significantly inhibited cell recruitment in several experimentally-induced and natural dermatitis models, indicating that chymase plays a role in dermal inflammatory reactions (Tomimori, Y. et al, 2002. *Biochem Pharmacol* 64:1187; Tomimori, Y. et al, 2002. *Lab Invest* 82:789-794; Watanabe, N. et al, 2002. *Int Arch Allergy Immunol* 128:235-239) and macrophages (Watanabe, N. et al, 2002. *Int Arch Allergy Immunol* 128:229-234). These in vivo studies indicate that either chymase activates a resident, dormant chemokine, or that chymase itself is chemotactic. Chymase was previously reported to be enzyme that was chemotactic for human leukocytes in vitro (Tomimori, Y. et al, 2002. *Biochem Pharmacol* 64:1187; Tomimori, Y. et al, 2002. *Lab Invest* 82:789-794; Tani, K. et al, 2000. *J Leukoc Biol* 67:585-589). Chymase can also cleave endothelins, producing 21- and 31-residue vasoactive peptides that are chemotactic for human monocytes, neutrophils (Cui, P. et al, 2001. *J Leukoc Biol* 70:306-312) and macrophages (Grimshaw, M. J. et al, 2002. *Eur J Immunol* 32:2393-2400). With regard to other proteases, the neutrophil granule protease cathepsin G has also been shown to be chemotactic for human neutrophils, monocytes and macrophages, in a manner likewise dependent on enzyme activity (Chertov, O. et al, 1997. *J Exp Med* 186:739-747; Moriuchi, H. et al, 2000. *J Virol* 74:6849-6855). Injection of cathepsin G into mouse skin resulted in neutrophil and macrophage recruitment (Moriuchi, H. et al, 2000. *J Virol* 74:6849-6855). In addition, CD13/endopeptidase N, an ectoenzyme and T cell chemoattractant (Tani, K. et al, 2000. *Am J Respir Crit Care Med* 161:1636-1642), was observed at elevated levels on alveolar macrophages in two separate rat models of airway T cell inflammation (Tani, K. et al, 2000. *Am J Respir Crit Care Med* 161:1636-1642; Huang, L. et al, 2002. *Radiat Res* 157:191-198). CD13 was also observed at elevated levels on synovial fibroblasts and in synovial fluid from patients with rheumatoid arthritis (Shimizu, T. et al, 2002. *Arthritis Rheum* 46:2330-2338).

The demonstration herein that C6* chemokines are activated by pro-inflammatory proteases in vitro is evidence that this type of regulation also occurs in vivo. In mice, CCL9/MIP-1γ mRNA is expressed constitutively in a wide variety of tissues in the absence of exogenous stimuli and in murine myeloid cell lines (Poltorak, A. N. et al, 1995. *J Inflamm* 45:207-219; Youn, B. S. et al, 1995. *J Immunol* 155:2661-2667; Hara, T. et al, 1995. *J Immunol* 155:5352-5358), in contrast to CCL3/MIP-1α mRNA which is expressed only in select tissues and only after the addition of exogenous stimuli such as LPS (Poltorak, A. N. et al, 1995. *J Inflamm* 45:207-219). CCL9/MIP-1γ protein has also been detected in multiple tissues (Poltorak, A. N. et al, 1995. *J Inflamm* 45:207-219) and in a Langerhans cell line (Mohamadzadeh, M. et al, 1996. *J Immunol* 156:3102-3106), and can reach 1 µg/ml (90 nM) in normal murine serum (Poltorak, A. N. et al, 1995. *J Inflamm* 45:207-219). CCL6/C10 mRNA is expressed in normal peritoneal cells (Wu, Y. et al, 1999. *Cytokine* 11:523-530) and full-length CCL6/C10 protein is expressed in normal lung macrophages, smooth muscle cells and fibroblasts (Hogaboam, C. M. et al, *J Immunol* 162:6071-6079). The constitutive expression of CCL9/MIP-1γ and CCL6/C10 indicates that C6* chemokines may be present during the very first steps of inflammation, when mast cells or neutrophils degranulate. Released proteases could activate the C6* chemokine, setting up an immediate gradient of an extremely potent CCR1 ligand.

In humans, no studies have been published which demonstrate CCL15/MIP-1δ or CCL23/CKβ8 protein expression in vivo. The results presented here now show that both CCL15/MIP-1δ and CCL23/CKβ8 were present in nearly all synovial fluid samples studied. (The CCL15/MIP-1δ and CCL23/CKβ8 present in the fluids were not a factor in the functional analyses of the in vitro digestions, since the synovial fluids were diluted 10-fold in the digestions and the digestions were diluted at least 100-fold in the functional assays.) Using antibody pairs that can discriminate between full-length and N-terminally truncated chemokines, we observed that most (if not all) of each chemokine is N-terminally truncated and present at concentrations (130-1700 pM), well above those required to elicit chemotaxis of THP-1 cells in vitro. In contrast, concentrations of CCL3/MIP-1α and CCL5/RANTES in the fluids were always less than 120 pM, and often below 20 pM—far below the concentration required for chemotaxis of THP-1 cells in vitro. The presence of substantially more CCL15/MIP-1δ and CCL23/CKβ8 than CCL3/MIP-1α and CCL5/RANTES in the synovial fluids is consistent with the observation that the former two chemokines are activated by the synovial fluids in vitro while the latter two chemokines are inactivated. These results indicate that in inflamed synovial tissue, where CCR1 is thought to play a critical role in leukocyte infiltration, N-terminally truncated CCL15/MIP-1δ and CCL23/CKβ8 rather than CCL3/MIP-1α or CCL5/RANTES actively recruit CCR1-bearing monocytes and neutrophils.

Example 2

Proteolytic Activation of FPRL1 Ligands and their Activities

I. Materials and Methods

Reagents. In humans, a single gene, CCL23, can give rise to 4 distinct protein products through alternative splicing of the third exon and N-terminal processing (FIG. 7A): 1) CCL23α, a 99-residue protein; 2) an alternatively spliced form of CCL23, encoding a 116-residue protein, CCL23β; 3) a truncated form of CCL23α, CCL23αΔ24; and 4) a truncated form of CCL23β, CCLβΔ24 (FIG. 1A). All chemokines were obtained from R&D Systems (Minneapolis, Minn.). Recombinant CCL23β was a special order, produced according to the published sequence (Youn, B. S. et al. Characterization of CKbeta8 and CKbeta8-1: two alternatively spliced forms of human beta-chemokine, chemoattractants for neutrophils, monocytes, and lymphocytes, and potent agonists at CC chemokine receptor 1. *Blood* 91, 3118-26 (1998)). The other three CCL23 variants: CCL23α, CCL23αΔ24, and CCLβΔ24 are R&D Systems regular catalog items (Cat. #s 371-MP, 131-M1, 508-CK). $^{125}$I-MIP1α and $^{125}$I-WKYMVm were obtained from Perkin Elmer (Boston, Mass.). Lipoxin $A_4$ was obtained from two sources; Calbiochem (San Diego, Calif.) and BioMol (Plymouth, Pa.). The β-amyloid protein (1-42) was obtained from American Peptide Company (Sunnyvale, Calif.). Serum amyloid A (SAA) was obtained from PeproTech (Rocky Hill, N.J.). fMLP, WKYMVm, WKYMVM, SHAAGtide (MLWRRKIG-PQMTLSHAAG), scrambled peptide version of SHAAGtide, CCL23β 1-42 peptide, and SHAAGtide mapping variants were synthesized by either Phoenix Pharmaceuticals (Belmont, Calif.) or SynPep (Dublin, Calif.).

Cells. Human monocytes were isolated from buffy coats (Stanford Blood Center, Palo Alto, Calif.) using CD14 microbeads (Miltenyi, Auburn, Calif.) and magnetic positive selection. Human neutrophils were isolated from fresh peripheral blood of healthy individuals by gradient centrifugation on Ficoll-Hypaque using standard protocols. Stable expression of human FPRL1 in L1.2 cells was generated by C. Gerard. Human L1.2-CCR1 cells were prepared with Superfect reagent (Qiagen, Valencia, Calif.) following the manufacturer's protocol. L1.2 transfectants were maintained in RPMI with 10% FBS with 2 mg/ml G-418, and treated with 8 mM sodium butyrate 16 hours prior to the experiment.

Immature and mature DC preparation. Immature DCs were derived by culturing CD14+ monocytes in T-175 cultured flasks at a density of $10^6$ cells/ml in RPMI supplemented with 10% FBS. Recombinant human cytokines GM-CSF and IL-4 (final concentration 1000 and 500 U/ml, respectively) were added on day 0, 2, 4 and 6. Cells were harvested on day 6 as immature DCs and characterized for surface marker expression by flow cytometry. DC maturation was carried out by culturing day-6 immature DCs in RPMI-10% FBS supplemented with GM-CSF, IL-4 and 50 µg/ml polyIC (Sigma, St. Louis Mo.). After two more days of culture, cells were harvested as mature DCs and characterized by surface marker expression by flow cytometry.

Binding assay. Competition binding studies were conducted using monocytes, L1.2-CCR1 or L1.2-FPRL1 cells. Cells were incubated for 3 hr at 4° C. with $^{125}$I-MIP-1α (final concentration ~0.05 nM) or $^{125}$I-WKYMVm (final concentration ~0.01 nM) in buffer (25 mM HEPES, 140 mM NaCl, 1 mM $CaCl_2$, 5 mM $MgCl_2$ and 0.2% BSA, adjusted to pH 7.1) in the presence of increasing amounts of unlabeled chemokine. Reactions were aspirated onto PEI-treated GF/B glass filters using a cell harvester (Packard). Filters were washed twice (25 mM HEPES, 500 mM NaCl, 1 mM $CaCl_2$, 5 mM $MgCl_2$, adjusted to pH 7.1). Scintillant (MicroScint-10; 35 µl) was added to the filters and counted in a Packard Topcount scintillation counter. Data were analyzed and plotted using Prism (GraphPad Software, San Diego, Calif.).

Receptor signaling assay. For individual measurements, cells were loaded for 45 min at room temperature with 2 µM indo-1/AM (Invitrogen, Carlsbad Calif.) in culture medium, then washed with 10 ml PBS and resuspended at $10^6$ cells/ml in HBSS containing 0.1% BSA. Cytosolic calcium levels were determined using a Photon Technology International fluorimeter (excitation at 350 nm, ratio of dual emission at 400 and 490 nm). For measuring calcium dose responses, cells were analyzed with a Fluorometric Imaging Plate Reader 384 (FLIPR$^{384}$) (Molecular Devices, Sunnyvale, Calif.). Cells were loaded for 1 hr at 37° C. with 5 μM fluo-4 in HBSS with 0.1% BSA, then washed, transferred to black-wall 96-well plates, and subsequently excited at 505 nm with emission recorded at 530 nm with a standard protocol provided by the manufacture. Cells were stimulated with agonists 20 s after the monitoring of fluorescence began. Data were analyzed and plotted in arbitrary units of fluorescence using Prism. To ensure that responses were specific to FPRL1, we utilized a selective small-molecule antagonist of human FPRL1, generated by ChemoCentryx, which was optimized from a high throughput compound library screening approach. This molecule is non-cytotoxic and does not interact with any of a large panel of chemokine receptors which have been tested.

Chemotaxis assays. L1.2-CCR1 and L1.2-FPRL1 transfectants, monocytes and neutrophils were collected by centrifugation and resuspended in HBSS with 0.1% BSA. The assays were performed in 96-well ChemoTx® microplates (Neuroprobe, Rockville, Md.). Chemokines were diluted in HBSS with 0.1% BSA and added to the lower wells (final volume 29 μL), then 20 μL of cell suspension (5×10$^6$ cells/mL for monocytes; 2.5×10$^6$ cells/mL for neutrophils) were added to the polycarbonate filters (5 μm pore size for monocytes and FPRL1 transfectants; 3 μm pore size for neutrophils). After incubation for 90 min (37° C., 100% humidity, 5% $CO_2$), the filters were removed and the cells that migrated into the lower chamber were quantified by using the CyQuant cell proliferation assay kit (Molecular Probes, Oreg.).

Immunohistochemistry. BALB/c and c57Bl/6 mice were injected intradermally with 50 μl sterile saline with or without 2 μg SHAAGtide. 6 hours later, mice were euthanized and the skin surrounding the injection site was excised. After immersion in 10% neutral-buffered formalin for 18-24 hours, the skin biopsy was processed in graded alcohols and embedded in paraffin wax. 5 μm-wide sections were cut on a Leica microtome, transferred to glass slides, deparaffinized in xylenes, and hydrated through graded alcohols. The sections were either stained with hematoxylin and eosin (Sigma, St. Louis Mo.) or stained immunohistochemically for neutrophils as follows. The slides were immersed in Target Retrieval solution (Dako, Carpinteria Calif.) for 20 minutes at 90° C., rinsed with water and immersed in tris-buffered saline (TBS) containing 2% bovine serum albumin for 20 minutes. The sections were then exposed to rat anti-mouse neutrophil monoclonal antibody (Accurate Chemical and Scientific, Westbury N.Y.) or rat $IgG_{2a}$ isotype control antibody (BD Pharmingen, San Diego Calif.) for 1 hour, rinsed with TBS, and exposed to biotinylated goat anti-rat Ig (Dako) for 30 minutes. The sections were then rinsed with TBS, stained with the ABC-AP and fuchsin reagents (both from Dako), rinsed with water, and counterstained with hematoxylin for 2 minutes. After rinsing with water, slides were mounted with Crystalmount (Biomeda, Foster City Calif.).

Analysis of CCL23β processing using SDS-PAGE and Ca signaling. Either CCL23β, CCL23β Δ24, or a synthetic peptide corresponding to the N-terminal 42 residues of CCL23β (containing the N-terminal and SHAAGtide domains) were incubated with recombinant enzymes or PMN supernatants. Four μg of chemokine was incubated at 37° C. for varying amounts of time in a 40 μl reaction volume containing 20 μl supernatants collected from human neutrophil-conditioned medium. Neutrophils were cultured in serum-free RPMI for 6 hours in the absence or presence of PMA (1 μg/ml) and ionomycin (0.1 μg/ml; both from Sigma, St. Louis Mo.). Recombinant enzyme studies used 100 ng human mast cell chymase (a kind gift of Dr. Norman Schechter, University of Pennsylvania) or Asp-N endopeptidase (Sigma) under similar conditions. Control reactions included neutrophil supernatant or protease without chemokine. The reactions were then subjected to SDS-PAGE on a 10-20% gradient acrylamide tricine gel (Invitrogen, Carlsbad Calif.) and stained with colloidal Coomassie (Pierce, Rockford Ill.).

II. Results

As mentioned above, in humans, a single gene, CCL23, can give rise to 4 distinct protein products through alternative splicing of the third exon and N-terminal processing (FIG. 7A). The CCL23α cDNA, encoding a 99-residue protein (initially designated CKβ8, MPIF-1), was initially isolated from a library derived from human aortic endothelial cells. The CCL23α transcript has been reported to be constitutively expressed in liver, lung, pancreas, and bone marrow, and the CCL23α protein has chemotactic activity on monocytes and some dendritic cells. An alternatively spliced form of CCL23, encoding a 116-residue protein termed CKβ8-1 (here designated CCL23β), was isolated from the myeloid cell line THP-1. The CCL23β mRNA utilizes a splice acceptor 51 nt upstream of the one utilized by the CCL23α mRNA, resulting in the replacement of the CCL23α $Arg^{25}$ residue with the 18-residue peptide MLWRRKIGPQMTLSHAAG (FIG. 7B). CCL23β mRNA expression has been detected in pancreas and skeletal muscle. It was demonstrated that both CCL23α and CCL23β proteins readily undergo proteolytic processing by inflammation-associated proteases which remove the 24-residue N-terminal domain encoded by exon 2. These truncated forms of CCL23α and CCL23β are herein designated CCL23α Δ24 and CCL23β Δ24, respectively (FIG. 7A). Three of the CCL23 protein variants, namely CCL23α, CCL23α Δ24, and CCL23β have all been reported to be functional ligands for CCR1 (Macphee, C. H. et al., *J Immunol* 161, 6273-9 (1998); Berkhout, T. A. et al., *Biochem Pharmacol* 59, 591-6 (2000); and Youn, B. S. et al., *Blood* 91, 3118-26 (1998)). Moreover, the N-terminal truncation of CCL23α to the shorter CCL23α Δ24 form increases its potency on CCR1 expressing cells (Macphee, C. H. et al., *J Immunol* 161, 6273-9 (1998); and Berkhout, T. A. et al., *Biochem Pharmacol* 59, 591-6 (2000)).

Figure 7C:
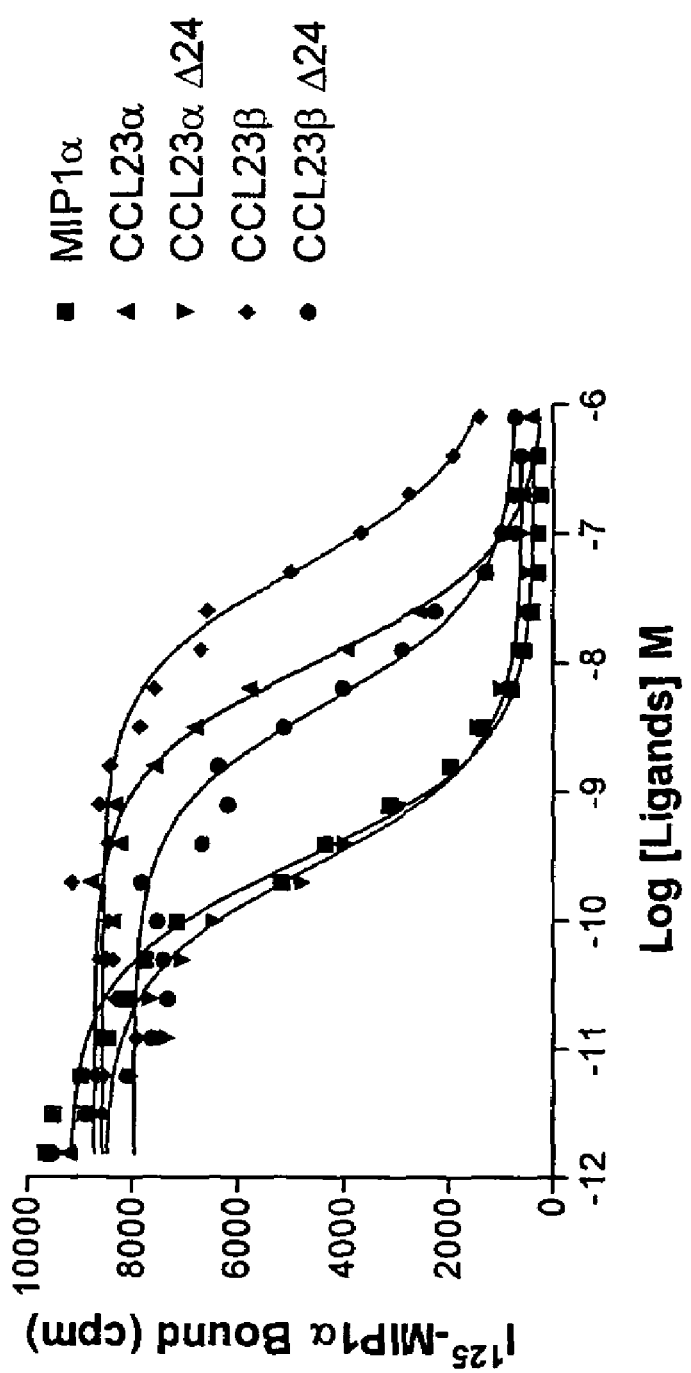
FIG. 7. Overview of CCL23 gene products. (A) Differential RNA splicing and proteolytic processing yields 4 distinct proteins. The CCL23 gene contains two splice acceptors in the $3^{rd}$ exon and therefore gives rise to two gene products, CCL23α and CCL23β, the latter containing a novel 18-residue insertion (shown in grey). Proteolytic truncation of the 24-residue N-terminal domain of these two proteins generates two more forms, termed CCL23α Δ24 and CCL23β Δ24, the latter beginning with the novel peptide insertion. (B) N-terminal amino acid alignment of the four CCL23 proteins. The 18-residue peptide of CCL23β replaces $Arg^{25}$ of CCL23α and is shown underlined. Shown in boxes are the first two conserved cysteine residues characteristic of the CC chemokine family. (C) Binding of the CCL23 protein variants to CCR1. Monocytes were incubated with 0.1 nM $^{125}$I-

To assess how the four CCL23 proteins compared in receptor binding and functional activity, particularly the CCL23β Δ24 protein which had not been previously characterized, a series of competitive binding analyses on cells bearing CCR1 was performed. All 4 proteins bound to CCR1 as evidenced by the fact that they each inhibited the binding of a radiolabelled CCR1 ligand ($^{125}$I-MIP-1α) to human monocytes (FIG. 7C). Similar experiments were performed using CCR1-transfected cells, with essentially identical results (not shown). CCL23α Δ24 was the most potent competitor, equipotent with CCL3/MIP-1α; however, since the binding sites of these two proteins on CCR1 may not be the same, and since the tracer was $^{125}$I-MIP-1α, the CCL23α Δ24 potency may actually be underestimated. Both CCL23α and CCL23β Δ24 were moderate competitors, while CCL23β exhibited the lowest binding activity for CCR1 (FIG. 7C). Indeed, removal of the N-terminal 24 residues resulted in >10-fold increases in the binding activity of full-length CCL23α and CCL23β. This suggests that the 24-residue N-terminal domain of CCL23α and CCL23β performs a negative regulatory function, and that the unique 18-residue insertion of CCL23β further inhibits the activity of the CCR1-binding domain located in the chemokine body (e.g. CCL23α Δ24).

A. The Novel CCL23 Variant, CCL23β Δ24, has Unique Activities Unrelated to CCR1 in Human Monocytes and Neutrophils The functional activity of the four CCL23 proteins on freshly prepared human leukocytes was examined. First, a detailed receptor signaling experiments on monocytes and neutrophils were conducted. All four CCL23 proteins were able to stimulate calcium mobilization in human monocytes (FIG. 8A), in agreement with the fact that monocytes express high levels of functional CCR1. However, whereas CCL23α and CCL23α Δ24 exhibited strong calcium responses in monocytes, CCL23β exhibited very weak responses, even when tested up to 250 nM. By contrast, the truncated form of CCL23β, CCL23β Δ24, exhibited a particularly strong and sustained calcium profile. The magnitude of the signal obtained with 100 nM CCL23β Δ24 was at least two fold higher than that obtained with the same concentration of CCL15 Δ24/leukotactin, itself a potent and selective CCR1 chemokine (FIG. 8A).

Figure 8B:
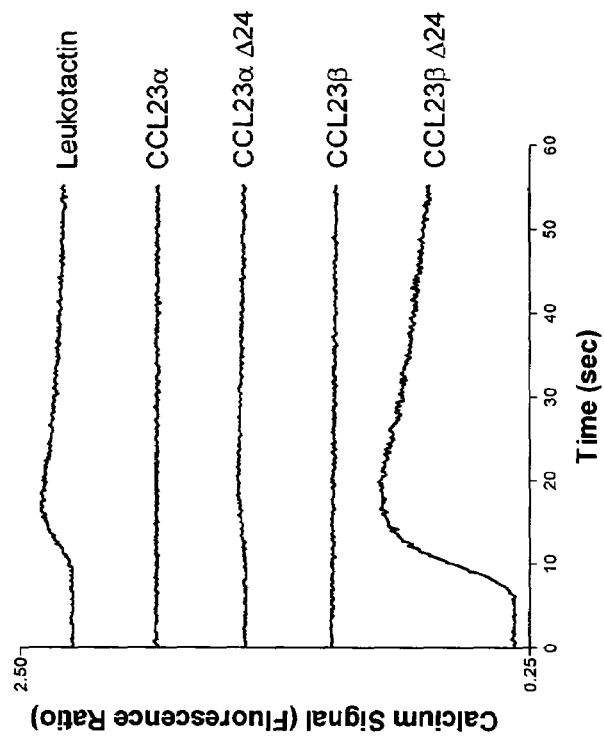
Figure 8A:
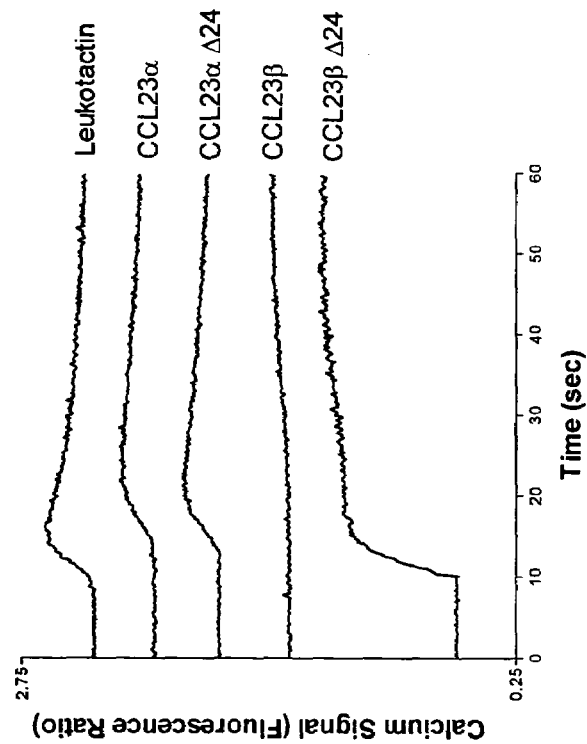

In contrast to monocytes, freshly-prepared neutrophils exhibited only moderate calcium responses to 100 nM CCL15 Δ24/leukotactin (FIG. 8B) and CCL3/MIP-1α (not shown), and did not respond to three of the four CCL23 proteins reported to act through CCR1 (FIG. 8B). This data suggested that CCR1 functionality in neutrophils is quite weak. However, in the same neutrophils, CCL23β Δ24 induced a very robust calcium response, many times greater than that of CCL15 Δ24/leukotactin (FIG. 8B, bottom) and even greater than that of the potent neutrophil activator IL-8 (not shown). Taken together, the data suggests that CCL23β Δ24 utilized a receptor pathway in monocytes and neutrophils that differed from the CCR1-mediated pathway utilized by the other CCL23 variants.

Figure 8C:
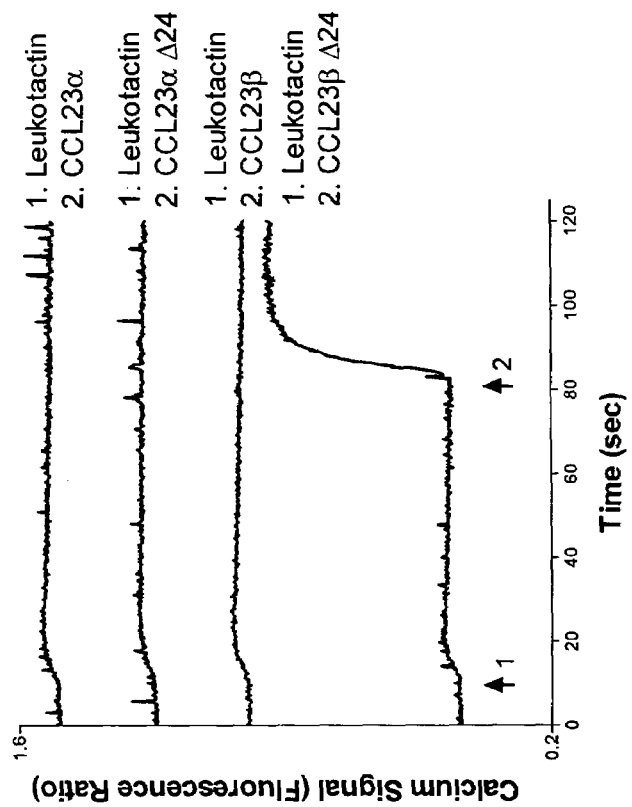
Figure 8D:
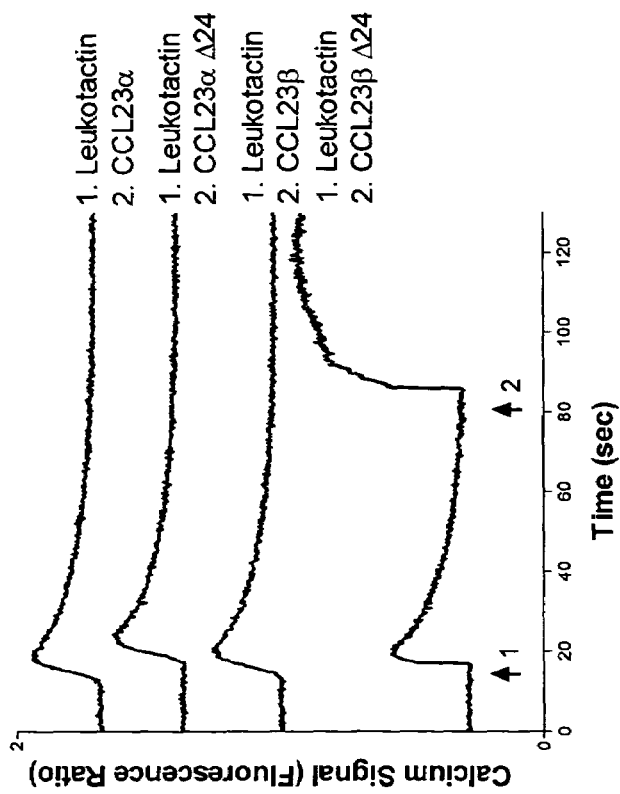

To exclude the possibility that the unique CCL23β Δ24 signaling activity in monocytes and neutrophils was mediated by CCR1, signaling cross-desensitization tests were employed. In monocytes, as shown in FIG. 8C, CCL15 Δ24/leukotactin completely desensitized the cells to CCL23α, CCL23α Δ24, and CCL23β, but not to CCL23β Δ24. In addition, it was noted that other well-characterized CCR1 agonists such as CCL5/RANTES and CCL3/MIP-1α were completely unable to desensitize monocytes to CCL23β Δ24 (not shown). CCL15 Δ24/leukotactin was also unable to desensitize neutrophils to CCL23β Δ24 (FIG. 8D). These data further supported the idea that CCL23β Δ24 can signal through a receptor distinct from CCR1 in monocytes and neutrophils.

B. The Unique CCL23β Δ24 Activity Maps to a Discrete Exon-Encoded Peptide Domain; the Domain can Function Apart from the Parent Protein Since the only structural difference between the chemokines CCL23β Δ24 and CCL23α Δ24 is that CCL23β Δ24 contains an 18-residue peptide in lieu of the N-terminal arginine, to determine whether this peptide was responsible for the novel signaling activities of CCL23β Δ24, a "SHAAGtide" (to reflect the 5 C-terminal residues of the peptide) was synthesized and compared to the parental CCL23β Δ24 chemokine using a variety of in vitro and in vivo functional assays. Surprisingly, SHAAGtide was equipotent to CCL23β Δ24 in receptor signaling assays (FIGS. 9A, B). A scrambled version of the peptide was unable to induce calcium mobilization, indicating that the SHAAGtide activity was sequence-specific. The potent CCR1 ligand CCL15 Δ24/leukotactin did not desensitize monocytes or neutrophils to SHAAGtide-induced calcium mobilization (not shown), indicating that the SHAAGtide signaling activity was not mediated by CCR1. The calcium responses induced by CCL23β Δ24 and SHAAGtide were ablated by pretreatment of the cells with pertussis toxin (PTX; not shown), indicating that the receptor in question is a typical GPCR using the Gi subunit of heterotrimeric G proteins.

In addition to the receptor signaling assays, chemotaxis assays were performed, using 96-well Boyden-type chambers. Both CCL23β Δ24 and SHAAGtide were fully functional, inducing vigorous chemotaxis of monocytes and neutrophils, while the scrambled peptide was ineffective (FIGS. 9C, D). CCL23α Δ24 which lacks the SHAAGtide domain, exhibited moderately strong chemoattraction for human monocytes (presumably via CCR1), but was unable to induce migration of neutrophils (FIG. 9D).

Figure 9E:
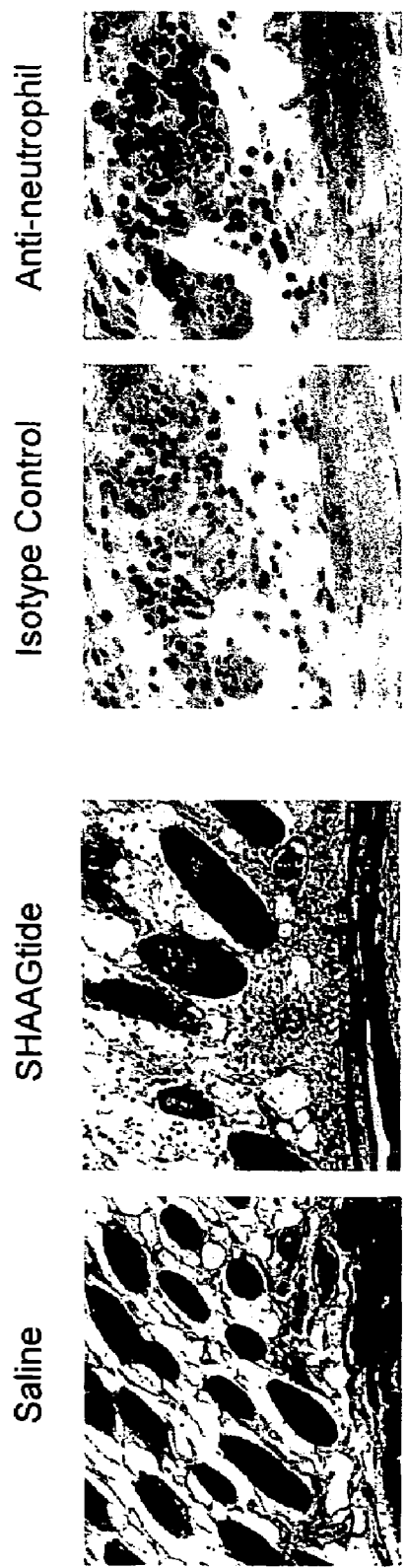

Both CCL23β Δ24 and SHAAGtide were able to induce calcium responses and chemotaxis in murine bone marrow neutrophils (not shown), suggesting that both ligands can to function through a mouse receptor counterpart. To better determine whether SHAAGtide was functional in vivo, we injected it intradermally into c57Bl/6 and BALB/c mice and analyzed the cells recruited to the site of injection 6 hours later by histology and immunohistochemistry. In the two different strains of mice, a 2 μg dose of SHAAGtide resulted in the consistent (6 of 6 mice) recruitment of leukocytes—primarily neutrophils—into the subcutis region of the dermis (FIG. 9E). Taken together, these data clearly indicated that the unique 18 amino acid segment of CCL23β Δ24 may function as a full agonist for leukocytes in vitro and in vivo.

C. CCL23β Δ24 is a Bifunctional Ligand for Two Receptors; the SHAAGtide Domain Accounts for Potent Signaling and Migration Activity Through FPRL1

Figures 10A, 10B:
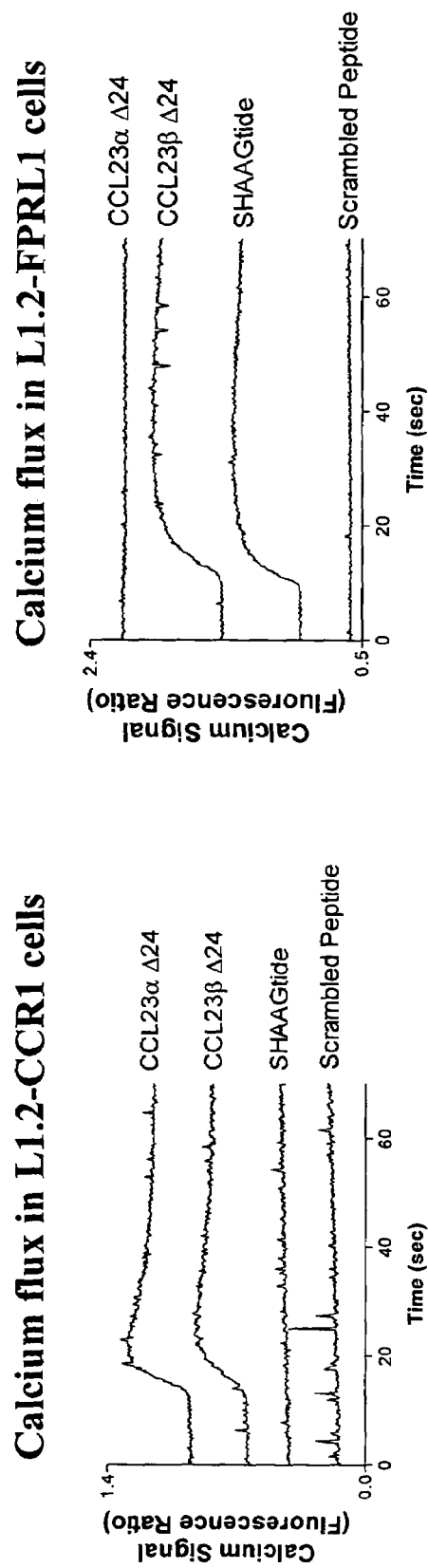
Figure 10C:
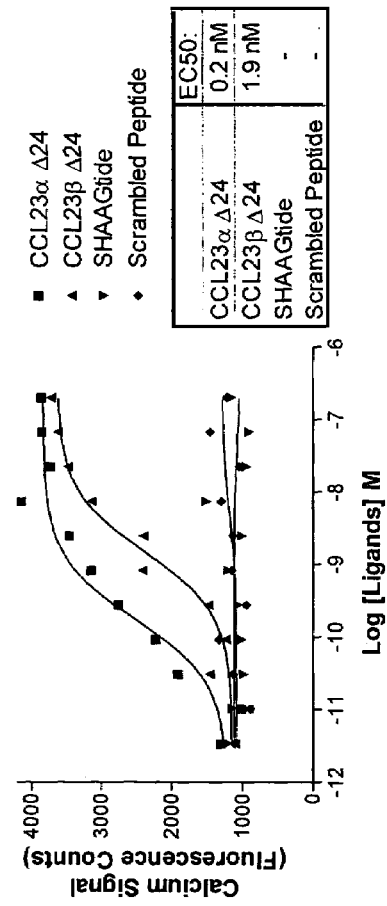
Figure 10D:
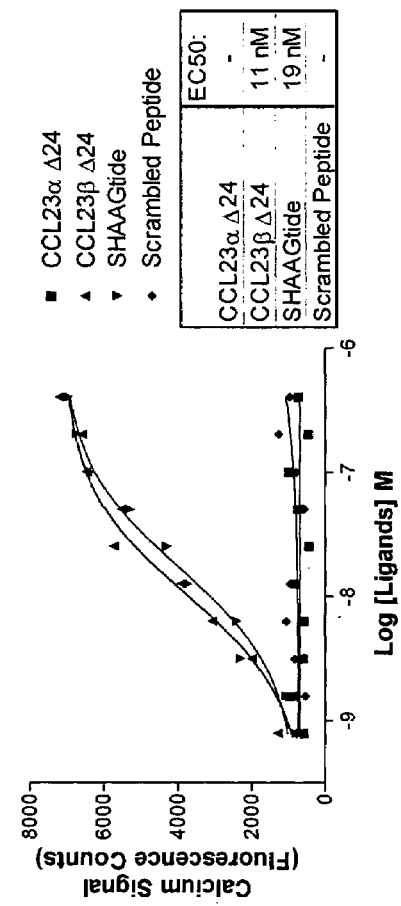
Figure 10E:
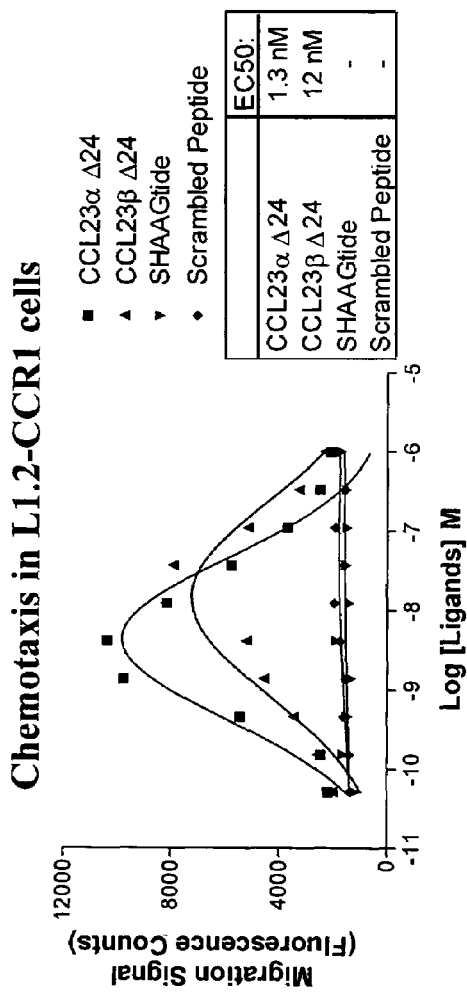
Figure 10F:
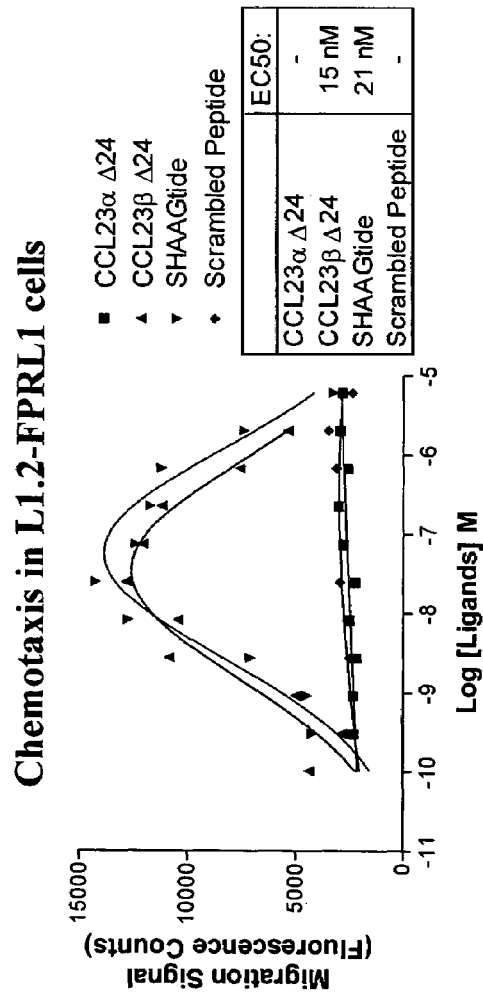

A number of 'orphan receptor' candidates for their role in the novel functional activities of CCL23β Δ24 and SHAAGtide peptide were tested. Since human monocytes, neutrophils and other myeloid lineage cells express high levels of the receptor FPRL1, the novel activities of CCL23β Δ24 and SHAAGtide might be mediated by this receptor. To examine this possibility we analyzed ligand-induced calcium mobilization in L1.2 cells stably expressing either human CCR1 or FPRL1 (FIG. 10). Although both of the N-terminally-truncated forms of CCL23 (CCL23α Δ24 and CCL23β Δ24) were effective at inducing calcium mobilization in the CCR1 transfectant, SHAAGtide was not (FIG. 10A). By contrast, in the FPRL1 transfectant, CCL23β Δ24 and isolated SHAAGtide were fully effective but CCL23α Δ24, lacking the SHAAGtide domain, was not (FIG. 10B). Dose-response profiles in L1.2-CCR1 and L1.2-FPRL1 cells confirmed that the SHAAGtide domain is entirely responsible for CCL23β Δ24's potent receptor signaling activity through FPRL1 (FIGS. 10C, D). Similarly, chemotaxis assays with the CCR1 and FPRL1 transfectants indicated that the SHAAGtide domain is entirely responsible for the chemotactic activity of CCL23β Δ24 through FPRL1 (FIGS. 10E, F).

D. Binding of CCL23β Δ24 and SHAAGtide to CCR1 and FPRL1

Figure 11A:
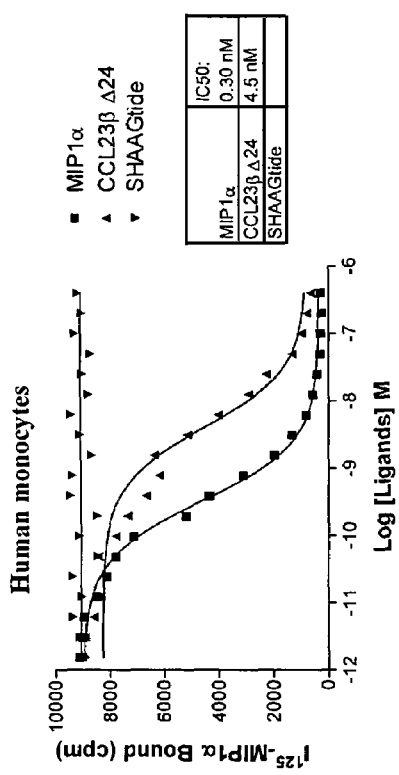
Figure 11B:
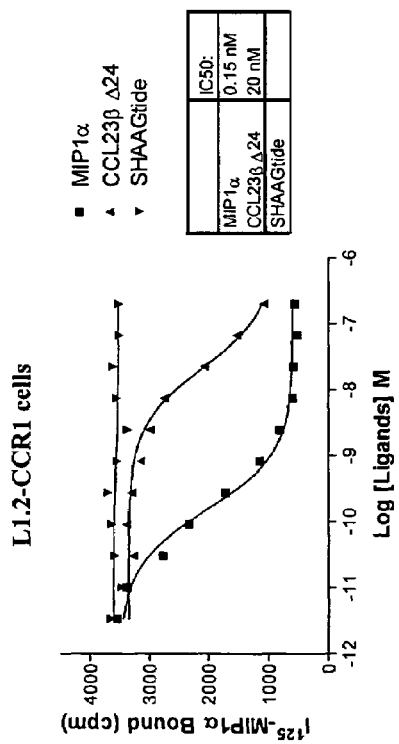

The ability of CCL23β Δ24 and SHAAGtide to bind to CCR1 and FPRL1 on the L1.2 transfectants and human monocytes was determined using the competitive binding assay noted above. The interaction with CCR1 was measured using $^{125}$I-MIP-1α tracer on L1.2-CCR1 cells and the monocytes (FIGS. 11A, B). Consistent with its calcium-mobilizing activity (FIG. 10), CCL23β Δ24 was observed to displace $^{125}$I-MIP-1α in a dose-dependent manner while SHAAGtide was unable to inhibit binding of $^{125}$I-MIP-1α to the L1.2-CCR1 cells (FIG. 11A). Homologous competitor (unlabelled MIP-1α) had a 50% inhibitory concentration ($IC_{50}$ value) of 0.15 nM, while CCL23β Δ24 had an $IC_{50}$ value of 20 nM. On monocytes, which have been reported to bind CCL23α, CCL23α Δ24, and MIP-1α via a shared site, the homologous competitor had an $IC_{50}$ value of 0.3 nM and CCL23β Δ24 had an $IC_{50}$ value of 4.5 nM (FIG. 11B). Consistent with the receptor signaling and migration data (FIG. 10), SHAAGtide did not inhibit [125]-MIP-1α binding to the monocytes (FIG. 11B).

Figure 11C:
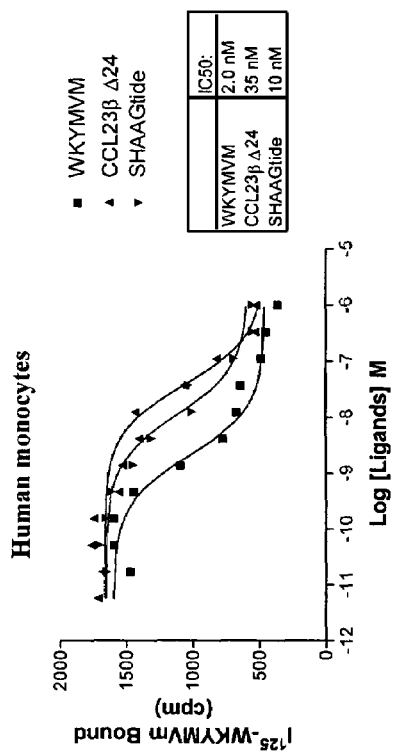
Figure 11D:
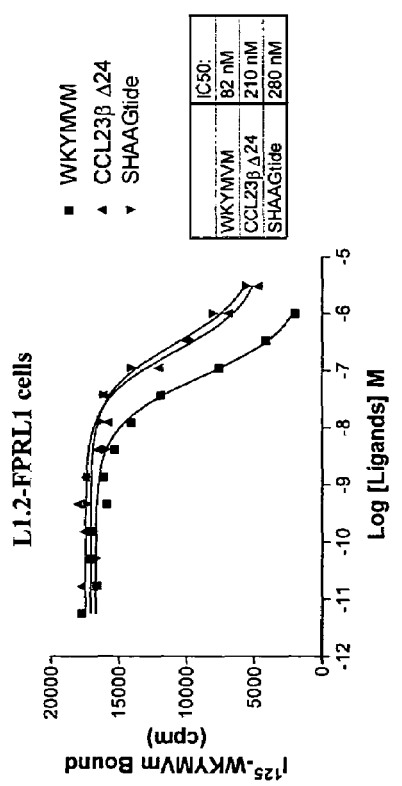

The binding of CCL23β Δ24 and SHAAGtide to FPRL1 was measured using $^{125}$I-labeled WKYMVm, a synthetic peptide noted for its adventitious activity on FPRL1, to the L1.2-FPRL1 cells and monocytes. On L1.2-FPRL1 cells, the $IC_{50}$ values for CCL23β Δ24 and SHAAGtide were 210 and 280 nM, respectively, while the $IC_{50}$ value for homologous competitor (unlabelled WKYMVM peptide) was 82 nM (FIG. 11C). On monocytes, the $IC_{50}$ values (using the $^{125}$I WKYMVm tracer) for CCL23β Δ24, SHAAGtide and WKYMVM were 35 nM, 10 nM and 2 nM, respectively, indicating that SHAAGtide was more potent than CCL23β Δ24. It should also be noted however that the specific binding sites of the $^{125}$I WKYMVm tracer and SHAAGtide on FPRL1 may not be the same, the SHAAGtide $IC_{50}$ value may actually be an underestimate. These results demonstrate that CCL23β Δ24 and SHAAGtide are high-affinity, natural FPRL1 ligands which at least partially share a binding site with the synthetic ligand WKYMVm.

E. Characterization SHAAGtide Activity in CD14 Monocyte Derived Immature and Mature Dendritic and Mature Dendritic Cells FPRL1 is down-regulated as monocytes differentiate into DC but maintained as monocytes differentiate into macrophages. To assess CCL23βΔ24 and SHAAGtide function during dendritic cell differentiation, a receptor signaling assays on CD14+ monocyte-derived immature and mature dendritic cells was performed. As expected, CCL23βΔ24 induced a strong calcium response in immature DC, presumably through CCR1 (FIG. 12B). However, SHAAGtide induced a much smaller calcium response in the immature DC than in monocytes (FIGS. 12A, B), confirming that FPRL1 is down-regulated during myeloid DC development. The cells further differentiated to mature DC, the CCL23βΔ24-induced calcium response diminished (FIG. 12C), confirming previous findings that CCR1 is down-regulated during DC maturation. However, SHAAGtide retained a small amount of signaling activity on mature DC, suggesting that FPRL1 may play further roles in these cells.

F. SHAAGtide Liberation from CCL23β Δ24 by Pro-Inflammatory Proteases

Figure 13A:
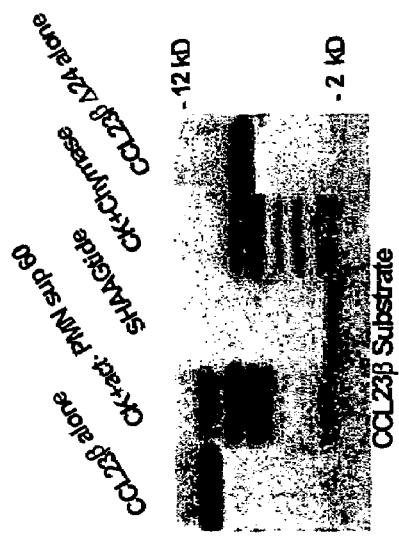
Figure 13B:
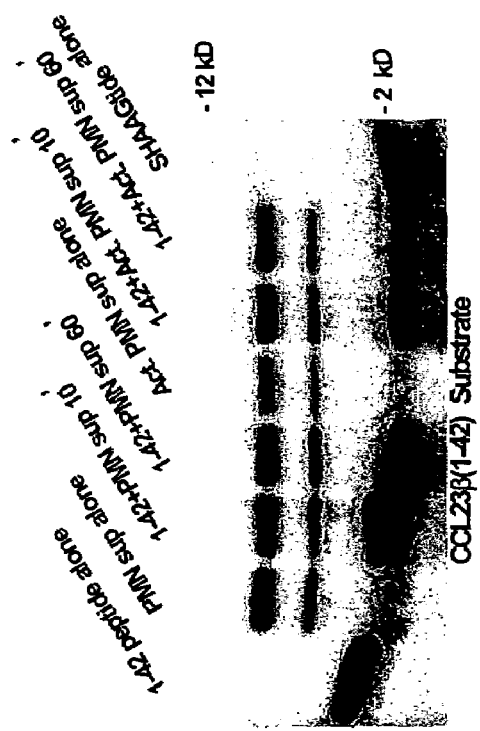

As indicated in Example 1, pro-inflammatory proteases, either purified or in supernatants of activated neutrophils or in human inflammatory fluids, remove the N-terminal domain from four 'alternative' CCR1 ligands (CCL6/C10/MRP-1, CCL9/MIP-1γ/MRP-2, CCL15/MIP-1δ/HCC-2/leukotactin-1 and CCL23/CKβ8/MPIF-1), thereby dramatically activating their functions on CCR1. Remarkably, most of the proteases truncated the four chemokines but were unable to cleave the truncated forms further. Similar experiments were performed to examine if a functionally-active fragment containing SHAAGtide could be released from CCL23β chemokine after exposure to the proteases. Full-length CCL23β was treated for various times with recombinant human mast cell chymase or with supernatants collected a 6-hour culture of freshly-prepared neutrophils with PMA and ionomycin (see Methods). After separation of the reaction products by SDS-PAGE, processing of CCL23β into smaller proteolytic fragments was readily detected. The largest of the proteolytic fragments was similar in mass to CCL23β Δ24, while the smallest of the fragments was similar in mass to SHAAGtide (FIG. 13A). SDS-PAGE analysis of shorter time-points suggested that CCL23β was processed step-wise, with the initial cleavage occurring between the SHAAGtide domain and the chemokine body (not shown). A synthetic 42-residue peptide consisting of the CCL23β N-terminal (1-24) and SHAAGtide (25-42) domains was digested with chymase and supernatants from unstimulated or activated neutrophils. Chymase (not shown) and both supernatants processed the 1-42 peptide into a SHAAGtide-sized fragment (see FIG. 13B, lanes 3 and 4), although the activated neutrophil supernatant displayed faster kinetics, which may be due to activation-associated cell degranulation. N-terminal sequencing analysis of the SHAAGtide-sized fragment indicated that the neutrophil supernatants cleaved the 1-42 peptide after Val[21], while chymase cleaved the 1-42 peptide after Leu[23] (not shown), producing SHAAGtides with N-terminal extensions of 3 (neutrophil supernatants) or 1 (chymase) amino acid. N-terminal sequencing of the CCL23β cleavage fragments indicated that the same N-terminally extended SHAAGtides were produced (not shown).

Figure 13D:
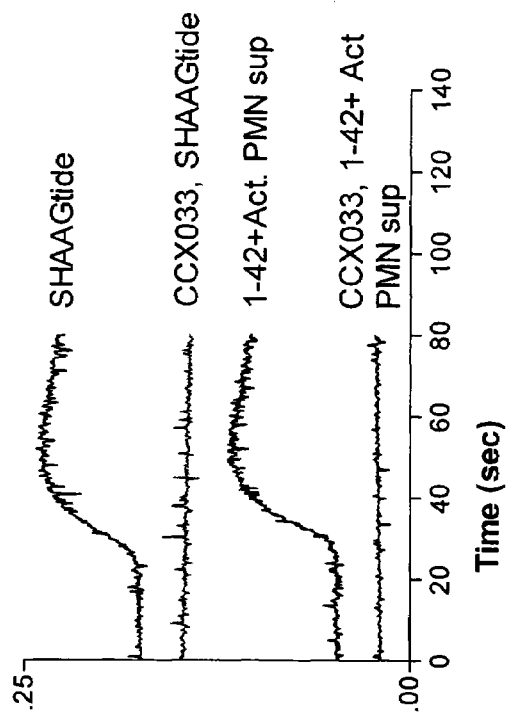
Figure 13C:
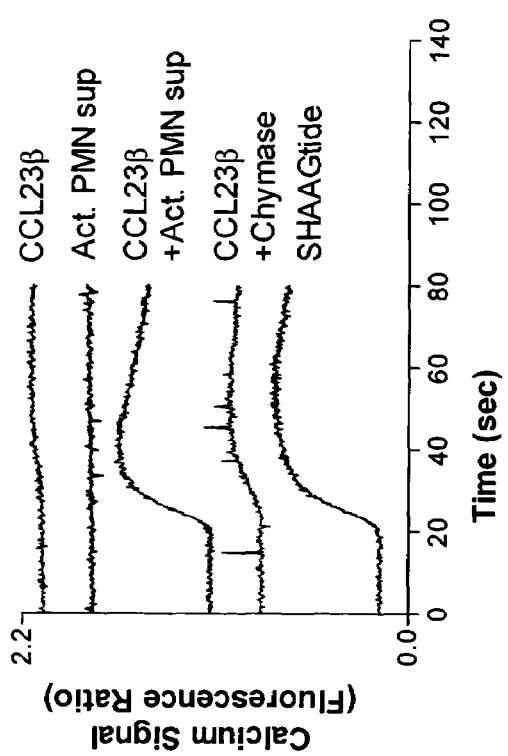
Figure 13E:
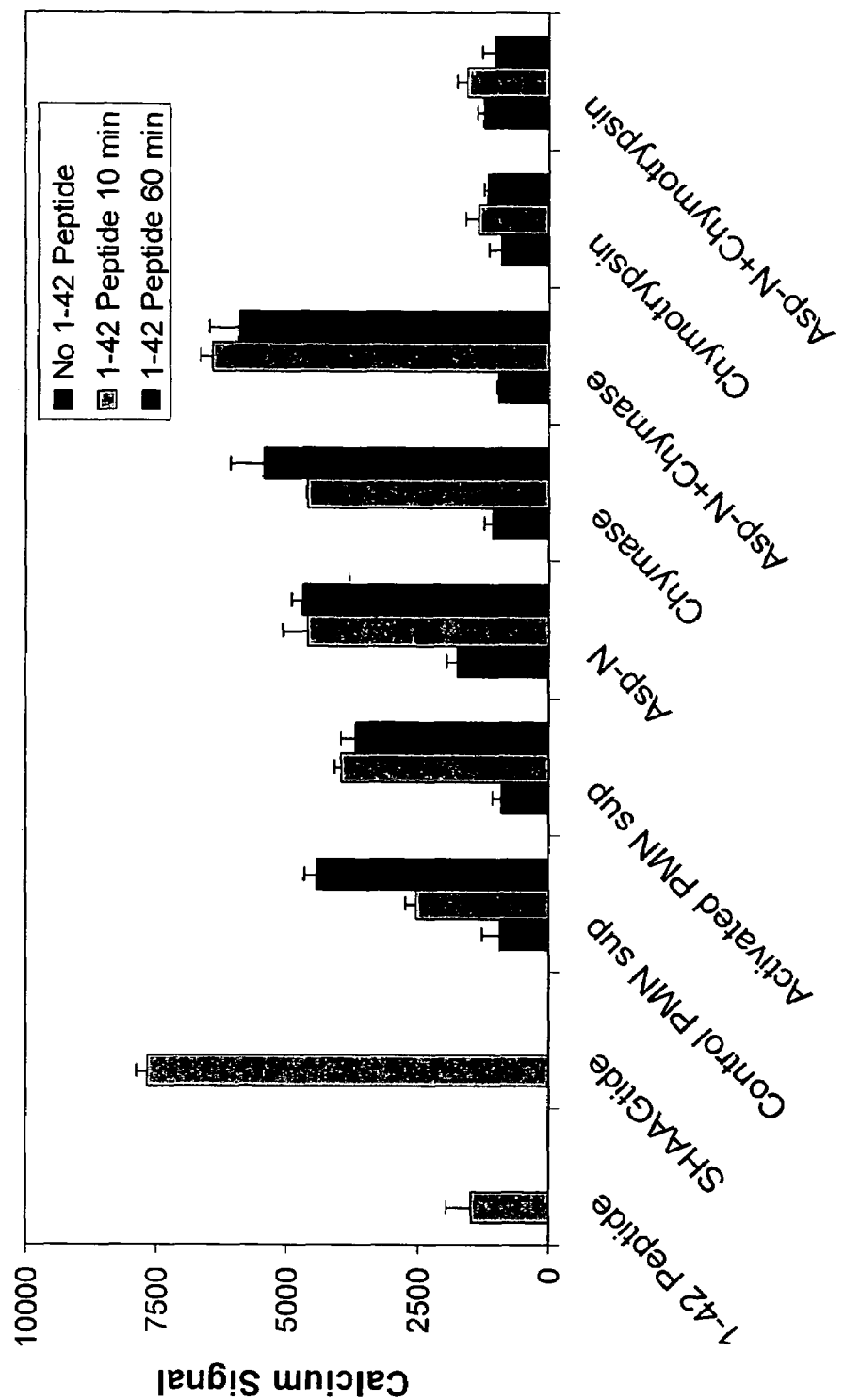

The biological activity of the protease-produced SHAAGtides was then tested in receptor signaling assays. Full-length CCL23β and 1-42 substrate peptide were unable to induce calcium mobilization in the L1.2-FPRL1 transfectant, but the protease-produced SHAAGtides induced robust signaling (FIG. 13C), indicating that these N-terminally extended SHAAGtides were functionally active for receptor signaling. Specificity for FPRL1 was demonstrated by the inability of the protease-produced SHAAGtides to induce calcium mobilization in wild-type L1.2 cells (not shown) and in L1.2-FPRL1 cells pre-treated for ~20 sec with a small-molecule antagonist developed at ChemoCentryx, designated CCX033, which is specific for FPRL1 (FIG. 13D). Receptor signaling assays were also performed on cleavage products of the 1-42 substrate peptide treated with purified enzymes Asp-N endopeptidase and chymotrypsin. Asp-N endopeptidase cleaved the 1-42 peptide into an active species, but that chymotrypsin did not (FIG. 13E). Incubation of the 1-42 peptide with a mixture of Asp-N and chymotrypsin failed to produce an active cleavage product, suggesting that chymotrypsin cleaved inside the active Asp-N fragment, rendering it inactive (FIG. 13D). Similar results were noted for CCL23β digestions with Asp-N and chymotrypsin (not shown). In addition, the ability to induce cell migration followed the pattern of receptor signaling (not shown). Interestingly, longer time-points of the CCL23β digestions were inactive in FPRL1 signaling and chemotaxis assays (not shown). SDS-PAGE analysis of these long-term digestion products no longer revealed a SHAAGtide-sized band, presumably due to protease cleavage within the SHAAGtide (not shown).

G. Functional Mapping of SHAAGtide

Since FPRL1 has been reported to interact with low affinity and/or potency with a spectrum of potential pathogenic ligands of viral, bacterial and endogenous origin, we performed comparative functional analyses to determine the precise functional domain for the SHAAGtide (FIG. 14). SHAAGtides containing N-terminal and C-terminal truncations and extensions were synthesized, and potencies for receptor signaling in L1.2-FPRL1 cells were tested. The data indicate that the N-terminus, but not the C-terminus, is essential for SHAAGtide activity. After removal of the N-terminal amino acid (Met) from SHAAGtide, its potency is reduced approximately 10 fold. Removal of the first two N-terminal amino acids (Met-Leu) totally abolished SHAAGtide's activity on FPRL1. Conversely, removal of the C-terminal three amino residues (AAG) from SHAAGtide had no effect on its activity on FPRL1. Removal of the C-terminal six residues (LSHAAG) reduced the peptide's potency only 3-fold. Many other purported naturally-occurring FPRL1 ligands, including serum amyloid A (SAA), beta-amyloid protein 42, lipoxin A4 and the bacterial tripeptide fMLP were tested. However, SHAAGtide was clearly more potent and efficacious in the receptor signaling and chemotaxis assays than these other ligands (not show).

III. Discussion

It was demonstrated that a processed form of the alternatively-spliced CCL23 (CKβ8/MPIF-1) gene product is a multifunctional, modular chemokine which potently engages both the chemokine receptor CCR1 and the chemoattractant receptor FPRL1. While the activity of this CCL23 chemokine, termed here CCL23β Δ24, on CCR1 is a function of the main body of the protein, the activity on FPRL1 is wholly accounted for by the peptide encoded by the alternatively spliced exon. This 18 amino acid peptide, which we term SHAAGtide, is as potent as its CCL23β Δ24 parent and is the most potent natural (i.e. non-synthetic) chemoattractant of monocytes and neutrophils we have tested; its chemotactic activity is greater than, for example, IL-8 or MCP-1. The SHAAGtide peptide retains full activity when isolated from the parental chemokine, exhibiting an $EC_{50}$ in functional assays of 10-30 nM, which is ~50 to 100-fold more potent than all other natural agents posited to act on FPRL1. SHAAGtide not only has potent signaling and chemoattractant properties in vitro, it is functional in vivo, recruiting leukocytes including neutrophils to the skin after intradermal injection.

Moreover, the inventors provided evidence that proteases associated with inflammation process the full-length CCL23β chemokine, which itself is not active on FPRL1. In vitro mast cell chymase and neutrophil supernatants (containing serine proteases such as cathepsin G and elastase) performed stepwise cleavages of CCL23β and an N-terminal peptide consisting of the N-terminal and SHAAGtide domains. Activation of the neutrophils, which causes protease release from intracellular granules, generated supernatants exhibiting faster kinetics of cleavage. As a result, N-terminally truncated, FPRL1-active CCL23 forms like CCL23β Δ24 were generated, as were smaller FPRL1-active peptides consisting mostly of the SHAAGtide domain.

The main body of the CCL23β Δ24 chemokine is a potent agonist for CCR1, a receptor which mediates adaptive immunity, controlling the basal trafficking of lymphocytes and monocytes to tissues and to sites of chronic inflammation, such as seen in rheumatoid arthritis and multiple sclerosis. In this respect, it is notable that some CCR1 ligands are capable of skewing adaptive immune responses to certain diseases or pathogens. Multiple roles for FPRL1 in host immunity are suggested by its interaction with a variety of proinflammatory and pathogenic ligands. CCL23β Δ24, or its released SHAAGtide domain, represents one such high affinity interaction, but most of the other interactions are of relatively low affinity. In this regard, FPRL1 may function both as a high affinity chemokine receptor (for CCL23β Δ24/SHAAGtide; here provisionally designated as CCR12), as well as a novel type of 'pattern recognition receptor' (PRR), interacting weakly with a broad array of pathogen-associated molecular patterns including HIV coat proteins, bacterial peptides, *Helicobacter* coat proteins, serum amyloid-related stress proteins, and host and pathogen produced eicosanoids. FPRL1 is expressed quite widely on 'frontline' innate immune cells, including those of the granulocyte, myeloid and DC lineages where it would be well-situated to initiate and coordinate innate and adaptive immune responses.

Alternative Embodiments

In one embodiment, the invention is a method for identifying an inhibitor of CCR1 activity, comprising (a) contacting protease with a chemokine substrate in the presence of a test compound; (b) determining the activity of the protease in the presence of the test compound; (c) comparing the activity of the protease in the presence of the test compound with the activity of the protease in the absence of the test compound; and (d) identifying the test compound as a potential inhibitor of CCR1 activity if the activity of the protease is inhibited in the presence of the test compound. The substrate may be selected from the group consisting of CCL6, CCL9, CCL15 and CCL23. The protease may be selected from the group consisting of chymase, cathepsin G, and elastase. The method may further comprise conducting an assay of CCR1 activity with the inhibitor identified in step (d) to determine whether the inhibitor inhibits an activity of CCR1.

In another embodiment, the invention is a method for identifying an inhibitor of FPRL1 activity, comprising: (a) contacting protease with a chemokine substrate in the presence of a test compound; (b) determining the activity of the protease in the presence of the test compound; (c) comparing the activity of the protease in the presence of the test compound with the activity of the protease in the absence of the test compound; and (d) identifying the test compound as a potential inhibitor of FPRL1 activity if the activity of the protease is inhibited in the presence of the test compound. The substrate may be CCL23β. The protease may be selected from the group consisting of chymase, cathepsin G, and elastase. The method may further comprise conducting an assay of FPR1 activity with the inhibitor identified in step (d) to determine whether the inhibitor inhibits an activity of FPRL1.

In another embodiment, the invention is a method for screening for a modulator of CCR1 activity, the method comprising assaying for an activity of a CCR1 receptor in the presence of a CCR1 ligand fragment and a test agent and comparing the activity level in the presence of the test agent with the activity level in the absence of the test agent, wherein a difference in the activity levels is an indication that the test agent is a modulator of the CCR1 activity. The CCR1 activity may be binding between the CCR1 receptor and the CCR1 ligand fragment. The CCR1 activity may be a biological activity selected from the group consisting of calcium mobilization, cell migration, and cell proliferation.

In another embodiment, the invention is a method for screening for a modulator of FPRL1 activity, the method comprising assaying for an activity of an FPRL1 receptor in the presence of an FPRL1 ligand fragment and a test agent and comparing the activity level in the presence of the test agent with the activity level in the absence of the test agent, wherein a difference in the activity levels is an indication that the test agent is a modulator of the FPRL1 activity. The FPRL1 activity is binding between the FPRL1 receptor and the FPRL1 ligand fragment. The FPRL1 activity is a biological activity selected from the group consisting of calcium mobilization, cell migration, and cell proliferation.

In yet another embodiment, the invention is a CCR1 ligand analogue, comprising: (a) a CCL6 analogue, wherein said CCL6 analogue comprises a CCL6 amino acid sequence in which there is a modification which inhibits cleavage between residues 13 and 27 by a serine protease; (b) a CCL9 analogue, wherein said CCL9 analogue comprises a CCL9 amino acid sequence in which there is a modification which inhibits cleavage between residues 13 and 26 by a serine protease; (c) a CCL15 analogue, wherein said CCL15 analogue comprises a CCL15 amino acid sequence in which there is a modification which inhibits cleavage between residues 17 and 32 by a serine protease; or (d) a CCL23 analogue, wherein said CCL23 analogue comprises a CCL23 amino acid sequence in which there is a modification which inhibits cleavage between residues 17 and 33 by a serine protease. The serine protease may be selected from the group consisting of chymase, cathepsin G, and elastase.

In another embodiment, the invention is a pharmaceutical composition comprising (i) an inhibitory agent that inhibits a serine protease having capacity to cleave an N-terminal fragment from CCL6, CCL9, CCL15 and/or CCL23 to generate a CCR1 ligand fragment that can activate CCR1, and (2) a pharmaceutically effective carrier. The inhibitory agent may be a CCR1 ligand analogue selected from the group consisting of: (a) a CCL6 analogue, wherein said CCL6 analogue comprises a CCL6 amino acid sequence in which there is a modification which inhibits cleavage between residues 13 and 27 by a serine protease; (b) a CCL9 analogue, wherein said CCL9 analogue comprises a CCL9 amino acid sequence in which there is a modification which inhibits cleavage between residues 13 and 26 by a serine protease; (c) a CCL15 analogue, wherein said CCL15 analogue comprises a CCL15 amino acid sequence in which there is a modification which inhibits cleavage between residues 17 and 32 by a serine protease; and (d) a CCL23 analogue, wherein said CCL23 analogue comprises a CCL23 amino acid sequence in which there is a modification which inhibits cleavage between residues 17 and 33 by a serine protease. The inhibitory agent may be a small molecule inhibitor of a serine protease selected from the group consisting of chymase, cathepsin G, and elastase. The inhibitory agent may be an antibody. In another embodiment, the invention is a method of treating an inflammatory condition correlated with CCR1 activity, the method comprising administering an effective amount of the pharmaceutical composition to an individual in need thereof.

In yet another embodiment, the invention is a pharmaceutical composition comprising (i) an inhibitory agent that inhibits a serine protease having capacity to cleave an N-terminal fragment from CCL23β to generate an FPRL1 ligand fragment that can activate FPRL1, and (2) a pharmaceutically effective carrier.

In another embodiment, the invention is a pharmaceutical composition comprising an inhibitory agent that inhibits a CCR1 ligand fragment from binding to CCR1 and a pharmaceutically effective carrier. The CCR1 ligand fragment may be selected from the group of polypeptides having the amino acid sequence of SEQ ID NOs:2-3, 5-8, 10-15 or 17-21. The inhibitory agent may be a small organic molecule. The inhibitory agent may be an antibody. In another embodiment, the invention is a method of treating an inflammatory condition correlated with CCR1 activity, the method comprising administering an effective amount of the pharmaceutical composition to an individual in need thereof.

In yet another embodiment, the invention is a pharmaceutical composition comprising an inhibitory agent that inhibits an FPRL1 ligand fragment from binding to FPRL1 and a pharmaceutically effective carrier.

In yet another embodiment, the invention is an isolated polypeptide that is a fragment of CCL6 (SEQ ID NO: 1), has at least 90% sequence identity to SEQ ID NO:2, and can bind CCR1.

In another embodiment, the invention is an isolated polypeptide that (1) is a truncated form of CCL6 (SEQ ID NO: 1) in which the N terminal 13-27 amino acids of CCL6 are deleted, and (2) can bind CCR1. The amino acid sequence may be that of SEQ ID NOs: 2 or 3.

In yet another embodiment, the invention is an isolated polypeptide that is a fragment of CCL9 (SEQ ID NO:4), has at least 90% sequence identity to SEQ ID NO:5, and can bind CCR1.

In another embodiment, the invention is an isolated polypeptide that (1) is a truncated form of CCL9 (SEQ ID NO:4) in which the N terminal 13-26 amino acids of CCL9 are deleted, and (2) can bind CCR1. The isolated polypeptide may have the amino acid sequence of SEQ ID NO:5, 6, 7 or 8.

In another embodiment, the invention is an isolated polypeptide that is a fragment of CCL15 (SEQ ID NO:9), has at least 90% sequence identity to SEQ ID NO:10, and can bind CCR1.

In another embodiment, the invention is an isolated polypeptide that (1) is a truncated form of CCL15 (SEQ ID NO:9) in which the N terminal 17-32 amino acids of CCL15 are deleted, and (2) can bind CCR1. The isolated polypeptide may have the amino acid sequence of SEQ ID NO:10, 11, 12, 13, 14 or 15.

In yet another embodiment, the invention is an isolated polypeptide that is a fragment of CCL23 (SEQ ID NO:16), has at least 90% sequence identity to SEQ ID NO:17, and can bind CCR1.

In yet another embodiment, the invention is an isolated polypeptide that (1) is a truncated form of CCL23 (SEQ ID NO: 16) in which the N terminal 17-33 amino acids of CCL23 are deleted, and (2) can bind CCR1. The isolated polypeptide may have the amino acid sequence of SEQ ID NO:17, 18, 19, 20 or 21.

In another embodiment, the invention is a method for inducing an immune response to an antigen in a subject, the method comprising administering a composition comprising a CCR1 ligand fragment to the subject, wherein the CCR1 ligand fragment is a polypeptide of claim 20, 23, 26 or 29.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated.

It is therefore intended that the foregoing detailed description be regarded as illustrative rather than limiting, and that it be understood that it is the following claims, including all equivalents, that are intended to define the spirit and scope of this invention.

The invention claimed is:

1. A method for identifying an inhibitor of chemoattractant receptor activity, comprising:
    (a) contacting protease with a chemoattractant substrate in the presence of a test compound;
    (b) determining the activity of the protease in the presence of the test compound;
    (c) comparing the activity of the protease in the presence of the test compound with the activity of the protease in the absence of the test compound;
    (d) identifying the test compound as a potential inhibitor of chemoattractant receptor activity if the activity of the protease is inhibited in the presence of the test compound.

2. The method of claim 1, wherein the protease is selected from the group consisting of chymase, cathepsin G, and elastase.

3. The method of claim 1, further comprising conducting an assay of the chemoattractant receptor activity with the inhibitor identified in step (d) to determine whether the inhibitor inhibits the activity of the chemoattractant receptor.

4. The method of claim 1, wherein the chemoattractant receptor is
N-formyl peptide receptor Like1 (FPRL1).

5. The method of claim 1, wherein the chemoattractant receptor is C-C-chemokine receptor 1 (CCR1).

6. The method of claim 1, wherein the chemoattractant receptor activity is a biological activity selected from the group consisting of calcium mobilization, cell migration, and cell proliferation.

7. The method of claim 4, wherein the substrate is C-C-chemokine ligand 23β (CCL23 β).

8. The method of claim 5, wherein the chemoattractant substrate is selected from the group consisting of C-C-chemokine ligand 6 (CCL6), C-C-chemokine ligand 9 (CCL9), C-C-chemokine ligand 15 (CCL15) and C-C-chemokine ligand 23 (CCL23).

9. The method of claim 7, wherein the protease is selected from the group consisting of chymase, cathepsin G, and elastase.

10. The method of claim 9, further comprising conducting an assay of FPRL1 activity with the inhibitor identified in step (d) to determine whether the inhibitor inhibits the activity of FPRL1.

* * * * *

UNITED STATES PATENT AND TRADEMARK OFFICE
CERTIFICATE OF CORRECTION

PATENT NO. : 7,572,600 B2  Page 1 of 1
APPLICATION NO. : 11/198935
DATED : August 11, 2009
INVENTOR(S) : Berahovich et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 707 days.

Signed and Sealed this

Seventh Day of September, 2010

David J. Kappos
*Director of the United States Patent and Trademark Office*

SEQUENCE LISTING

<160> NUMBER OF SEQ ID NOS: 50

<210> SEQ ID NO 1
<211> LENGTH: 95
<212> TYPE: PRT
<213> ORGANISM: Homo sapiens

```
<400> SEQUENCE: 1

Gly Leu Ile Gln Glu Met Glu Lys Glu Asp Arg Arg Tyr Asn Pro Pro
1               5                  10                  15

Ile Ile His Gln Gly Phe Gln Asp Thr Ser Ser Asp Cys Cys Phe Ser
            20                  25                  30

Tyr Ala Thr Gln Ile Pro Cys Lys Arg Phe Ile Tyr Tyr Phe Pro Thr
        35                  40                  45

Ser Gly Gly Cys Ile Lys Pro Gly Ile Ile Phe Ile Ser Arg Arg Gly
    50                  55                  60

Thr Gln Val Cys Ala Asp Pro Ser Asp Arg Arg Val Gln Arg Cys Leu
65                  70                  75                  80

Ser Thr Leu Lys Gln Gly Pro Arg Ser Gly Asn Lys Val Ile Ala
                85                  90                  95

<210> SEQ ID NO 2
<211> LENGTH: 74
<212> TYPE: PRT
<213> ORGANISM: Artificial Sequence
<220> FEATURE:
<223> OTHER INFORMATION: CCL fragment generated after incubation with
      synovial fluid

<400> SEQUENCE: 2

Phe Gln Asp Thr Ser Ser Asp Cys Cys Phe Ser Tyr Ala Thr Gln Ile
1               5                  10                  15

Pro Cys Lys Arg Phe Ile Tyr Tyr Phe Pro Thr Ser Gly Gly Cys Ile
            20                  25                  30

Lys Pro Gly Ile Ile Phe Ile Ser Arg Arg Gly Thr Gln Val Cys Ala
        35                  40                  45

Asp Pro Ser Asp Arg Arg Val Gln Arg Cys Leu Ser Thr Leu Lys Gln
    50                  55                  60

Gly Pro Arg Ser Gly Asn Lys Val Ile Ala
65                  70

<210> SEQ ID NO 3
<211> LENGTH: 73
<212> TYPE: PRT
<213> ORGANISM: Artificial Sequence
<220> FEATURE:
<223> OTHER INFORMATION: CCL6 fragment generated after incubation with
      chymase

<400> SEQUENCE: 3

Gln Asp Thr Ser Ser Asp Cys Cys Phe Ser Tyr Ala Thr Gln Ile Pro
1               5                  10                  15

Cys Lys Arg Phe Ile Tyr Tyr Phe Pro Thr Ser Gly Gly Cys Ile Lys
            20                  25                  30

Pro Gly Ile Ile Phe Ile Ser Arg Arg Gly Thr Gln Val Cys Ala Asp
        35                  40                  45

Pro Ser Asp Arg Arg Val Gln Arg Cys Leu Ser Thr Leu Lys Gln Gly
    50                  55                  60

Pro Arg Ser Gly Asn Lys Val Ile Ala
65                  70

<210> SEQ ID NO 4
<211> LENGTH: 101
<212> TYPE: PRT
<213> ORGANISM: Homo sapiens
```

<400> SEQUENCE: 4

Gln Ile Thr His Ala Thr Glu Thr Lys Glu Val Gln Ser Ser Leu Lys
1               5                   10                  15

Ala Gln Gln Gly Leu Glu Ile Glu Met Phe His Met Gly Phe Gln Asp
            20                  25                  30

Ser Ser Asp Cys Cys Leu Ser Tyr Asn Ser Arg Ile Gln Cys Ser Arg
        35                  40                  45

Phe Ile Gly Tyr Phe Pro Thr Ser Gly Gly Cys Thr Arg Pro Gly Ile
    50                  55                  60

Ile Phe Ile Ser Lys Arg Gly Phe Gln Val Cys Ala Asn Pro Ser Asp
65                  70                  75                  80

Arg Arg Val Gln Arg Cys Ile Glu Arg Leu Glu Gln Asn Ser Gln Pro
                85                  90                  95

Arg Thr Tyr Lys Gln
            100

<210> SEQ ID NO 5
<211> LENGTH: 74
<212> TYPE: PRT
<213> ORGANISM: Artificial Sequence
<220> FEATURE:
<223> OTHER INFORMATION: CCL9 fragment generated after incubation with
      synovial fluid

<400> SEQUENCE: 5

Met Gly Phe Gln Asp Ser Ser Asp Cys Cys Leu Ser Tyr Asn Ser Arg
1               5                   10                  15

Ile Gln Cys Ser Arg Phe Ile Gly Tyr Phe Pro Thr Ser Gly Gly Cys
            20                  25                  30

Thr Arg Pro Gly Ile Ile Phe Ile Ser Lys Arg Gly Phe Gln Val Cys
        35                  40                  45

Ala Asn Pro Ser Asp Arg Arg Val Gln Arg Cys Ile Glu Arg Leu Glu
    50                  55                  60

Gln Asn Ser Gln Pro Arg Thr Tyr Lys Gln
65                  70

<210> SEQ ID NO 6
<211> LENGTH: 73
<212> TYPE: PRT
<213> ORGANISM: Artificial Sequence
<220> FEATURE:
<223> OTHER INFORMATION: CCL9 fragment generated after incubation with
      elastase or activatedneutrophil-conditional media

<400> SEQUENCE: 6

Gly Phe Gln Asp Ser Ser Asp Cys Cys Leu Ser Tyr Asn Ser Arg Ile
1               5                   10                  15

Gln Cys Ser Arg Phe Ile Gly Tyr Phe Pro Thr Ser Gly Gly Cys Thr
            20                  25                  30

Arg Pro Gly Ile Ile Phe Ile Ser Lys Arg Gly Phe Gln Val Cys Ala
        35                  40                  45

Asn Pro Ser Asp Arg Arg Val Gln Arg Cys Ile Glu Arg Leu Glu Gln
    50                  55                  60

Asn Ser Gln Pro Arg Thr Tyr Lys Gln
65                  70

<210> SEQ ID NO 7
<211> LENGTH: 72
<212> TYPE: PRT
<213> ORGANISM: Artificial Sequence
<220> FEATURE:
<223> OTHER INFORMATION: CCL9 fragment generated after incubation with synovial fluid

<400> SEQUENCE: 7

Phe Gln Asp Ser Ser Asp Cys Cys Leu Ser Tyr Asn Ser Arg Ile Gln
1               5                   10                  15

Cys Ser Arg Phe Ile Gly Tyr Phe Pro Thr Ser Gly Gly Cys Thr Arg
            20                  25                  30

Pro Gly Ile Ile Phe Ile Ser Lys Arg Gly Phe Gln Val Cys Ala Asn
        35                  40                  45

Pro Ser Asp Arg Arg Val Gln Arg Cys Ile Glu Arg Leu Glu Gln Asn
    50                  55                  60

Ser Gln Pro Arg Thr Tyr Lys Gln
65                  70

<210> SEQ ID NO 8
<211> LENGTH: 71
<212> TYPE: PRT
<213> ORGANISM: Artificial Sequence
<220> FEATURE:
<223> OTHER INFORMATION: CCL9 fragment generated after incubation with chymase or cathepsin G

<400> SEQUENCE: 8

Gln Asp Ser Ser Asp Cys Cys Leu Ser Tyr Asn Ser Arg Ile Gln Cys
1               5                   10                  15

Ser Arg Phe Ile Gly Tyr Phe Pro Thr Ser Gly Gly Cys Thr Arg Pro
            20                  25                  30

Gly Ile Ile Phe Ile Ser Lys Arg Gly Phe Gln Val Cys Ala Asn Pro
        35                  40                  45

Ser Asp Arg Arg Val Gln Arg Cys Ile Glu Arg Leu Glu Gln Asn Ser
    50                  55                  60

Gln Pro Arg Thr Tyr Lys Gln
65                  70

<210> SEQ ID NO 9
<211> LENGTH: 92
<212> TYPE: PRT
<213> ORGANISM: Homo sapiens

<400> SEQUENCE: 9

Gln Phe Ile Asn Asp Ala Glu Thr Glu Leu Met Met Ser Lys Leu Pro
1               5                   10                  15

Leu Glu Asn Pro Val Val Leu Asn Ser Phe His Phe Ala Ala Asp Cys
            20                  25                  30

Cys Thr Ser Tyr Ile Ser Gln Ser Ile Pro Cys Ser Leu Met Lys Ser
        35                  40                  45

Tyr Phe Glu Thr Ser Ser Glu Cys Ser Lys Pro Gly Val Ile Phe Leu
    50                  55                  60

Thr Lys Lys Gly Arg Gln Val Cys Ala Lys Pro Ser Gly Pro Gly Val
65                  70                  75                  80

Gln Asp Cys Met Lys Lys Leu Lys Pro Tyr Ser Ile
                85                  90

```
<210> SEQ ID NO 10
<211> LENGTH: 78
<212> TYPE: PRT
<213> ORGANISM: Artificial Sequence
<220> FEATURE:
<223> OTHER INFORMATION: CCL15 fragment generated after incubation with
      synovial fluid

<400> SEQUENCE: 10

Leu Pro Leu Glu Asn Pro Val Val Leu Asn Ser Phe His Phe Ala Ala
1               5                   10                  15

Asp Cys Cys Thr Ser Tyr Ile Ser Gln Ser Ile Pro Cys Ser Leu Met
            20                  25                  30

Lys Ser Tyr Phe Glu Thr Ser Ser Glu Cys Ser Lys Pro Gly Val Ile
        35                  40                  45

Phe Leu Thr Lys Lys Gly Arg Gln Val Cys Ala Lys Pro Ser Gly Pro
    50                  55                  60

Gly Val Gln Asp Cys Met Lys Lys Leu Lys Pro Tyr Ser Ile
65                  70                  75

<210> SEQ ID NO 11
<211> LENGTH: 74
<212> TYPE: PRT
<213> ORGANISM: Artificial Sequence
<220> FEATURE:
<223> OTHER INFORMATION: CCL15 fragment generated after incubation with
      synovial fluid

<400> SEQUENCE: 11

Asn Pro Val Val Leu Asn Ser Phe His Phe Ala Ala Asp Cys Cys Thr
1               5                   10                  15

Ser Tyr Ile Ser Gln Ser Ile Pro Cys Ser Leu Met Lys Ser Tyr Phe
            20                  25                  30

Glu Thr Ser Ser Glu Cys Ser Lys Pro Gly Val Ile Phe Leu Thr Lys
        35                  40                  45

Lys Gly Arg Gln Val Cys Ala Lys Pro Ser Gly Pro Gly Val Gln Asp
    50                  55                  60

Cys Met Lys Lys Leu Lys Pro Tyr Ser Ile
65                  70

<210> SEQ ID NO 12
<211> LENGTH: 71
<212> TYPE: PRT
<213> ORGANISM: Artificial Sequence
<220> FEATURE:
<223> OTHER INFORMATION: CCL15 fragment generated after incubation with
      elastase or activated neutrophil conditioned media

<400> SEQUENCE: 12

Val Leu Asn Ser Phe His Phe Ala Ala Asp Cys Cys Thr Ser Tyr Ile
1               5                   10                  15

Ser Gln Ser Ile Pro Cys Ser Leu Met Lys Ser Tyr Phe Glu Thr Ser
            20                  25                  30

Ser Glu Cys Ser Lys Pro Gly Val Ile Phe Leu Thr Lys Lys Gly Arg
        35                  40                  45

Gln Val Cys Ala Lys Pro Ser Gly Pro Gly Val Gln Asp Cys Met Lys
    50                  55                  60

Lys Leu Lys Pro Tyr Ser Ile
65                  70
```

<210> SEQ ID NO 13
<211> LENGTH: 69
<212> TYPE: PRT
<213> ORGANISM: Artificial Sequence
<220> FEATURE:
<223> OTHER INFORMATION: CCL15 fragment generated after incubation with
cathepsin G

<400> SEQUENCE: 13

Asn Ser Phe His Phe Ala Ala Asp Cys Cys Thr Ser Tyr Ile Ser Gln
1               5                   10                  15

Ser Ile Pro Cys Ser Leu Met Lys Ser Tyr Phe Glu Thr Ser Ser Glu
            20                  25                  30

Cys Ser Lys Pro Gly Val Ile Phe Leu Thr Lys Lys Gly Arg Gln Val
        35                  40                  45

Cys Ala Lys Pro Ser Gly Pro Gly Val Gln Asp Cys Met Lys Lys Leu
    50                  55                  60

Lys Pro Tyr Ser Ile
65

<210> SEQ ID NO 14
<211> LENGTH: 68
<212> TYPE: PRT
<213> ORGANISM: Artificial Sequence
<220> FEATURE:
<223> OTHER INFORMATION: CCL15 fragment generated after incubation with
synovial fluid

<400> SEQUENCE: 14

Ser Phe His Phe Ala Ala Asp Cys Cys Thr Ser Tyr Ile Ser Gln Ser
1               5                   10                  15

Ile Pro Cys Ser Leu Met Lys Ser Tyr Phe Glu Thr Ser Ser Glu Cys
            20                  25                  30

Ser Lys Pro Gly Val Ile Phe Leu Thr Lys Lys Gly Arg Gln Val Cys
        35                  40                  45

Ala Lys Pro Ser Gly Pro Gly Val Gln Asp Cys Met Lys Lys Leu Lys
    50                  55                  60

Pro Tyr Ser Ile
65

<210> SEQ ID NO 15
<211> LENGTH: 64
<212> TYPE: PRT
<213> ORGANISM: Artificial Sequence
<220> FEATURE:
<223> OTHER INFORMATION: CCL15 fragment generated after incubation with
chymase or cathepsin G

<400> SEQUENCE: 15

Ala Ala Asp Cys Cys Thr Ser Tyr Ile Ser Gln Ser Ile Pro Cys Ser
1               5                   10                  15

Leu Met Lys Ser Tyr Phe Glu Thr Ser Ser Glu Cys Ser Lys Pro Gly
            20                  25                  30

Val Ile Phe Leu Thr Lys Lys Gly Arg Gln Val Cys Ala Lys Pro Ser
        35                  40                  45

Gly Pro Gly Val Gln Asp Cys Met Lys Lys Leu Lys Pro Tyr Ser Ile
    50                  55                  60

<210> SEQ ID NO 16
<211> LENGTH: 99
<212> TYPE: PRT
<213> ORGANISM: Homo sapiens

```
<400> SEQUENCE: 16

Arg Val Thr Lys Asp Ala Glu Thr Glu Phe Met Met Ser Lys Leu Pro
1               5                   10                  15

Leu Glu Asn Pro Val Leu Leu Asp Arg Phe His Ala Thr Ser Ala Asp
            20                  25                  30

Cys Cys Ile Ser Tyr Thr Pro Arg Ser Ile Pro Cys Ser Leu Leu Glu
        35                  40                  45

Ser Tyr Phe Glu Thr Asn Ser Glu Cys Ser Lys Pro Gly Val Ile Phe
    50                  55                  60

Leu Thr Lys Lys Gly Arg Arg Phe Cys Ala Asn Pro Ser Asp Lys Gln
65                  70                  75                  80

Val Gln Val Cys Met Arg Met Leu Lys Leu Asp Thr Arg Ile Lys Thr
                85                  90                  95

Arg Lys Asn

<210> SEQ ID NO 17
<211> LENGTH: 85
<212> TYPE: PRT
<213> ORGANISM: Artificial Sequence
<220> FEATURE:
<223> OTHER INFORMATION: CCl23 fragment generated after incubation with
      synovial fluid

<400> SEQUENCE: 17

Leu Pro Leu Glu Asn Pro Val Leu Leu Asp Arg Phe His Ala Thr Ser
1               5                   10                  15

Ala Asp Cys Cys Ile Ser Tyr Thr Pro Arg Ser Ile Pro Cys Ser Leu
            20                  25                  30

Leu Glu Ser Tyr Phe Glu Thr Asn Ser Glu Cys Ser Lys Pro Gly Val
        35                  40                  45

Ile Phe Leu Thr Lys Lys Gly Arg Arg Phe Cys Ala Asn Pro Ser Asp
    50                  55                  60

Lys Gln Val Gln Val Cys Met Arg Met Leu Lys Leu Asp Thr Arg Ile
65                  70                  75                  80

Lys Thr Arg Lys Asn
                85

<210> SEQ ID NO 18
<211> LENGTH: 81
<212> TYPE: PRT
<213> ORGANISM: Artificial Sequence
<220> FEATURE:
<223> OTHER INFORMATION: CCL23 fragment generated after incubation with
      synovial fluid

<400> SEQUENCE: 18

Asn Pro Val Leu Leu Asp Arg Phe His Ala Thr Ser Ala Asp Cys Cys
1               5                   10                  15

Ile Ser Tyr Thr Pro Arg Ser Ile Pro Cys Ser Leu Leu Glu Ser Tyr
            20                  25                  30

Phe Glu Thr Asn Ser Glu Cys Ser Lys Pro Gly Val Ile Phe Leu Thr
        35                  40                  45

Lys Lys Gly Arg Arg Phe Cys Ala Asn Pro Ser Asp Lys Gln Val Gln
    50                  55                  60

Val Cys Met Arg Met Leu Lys Leu Asp Thr Arg Ile Lys Thr Arg Lys
65                  70                  75                  80

Asn
```

```
<210> SEQ ID NO 19
<211> LENGTH: 78
<212> TYPE: PRT
<213> ORGANISM: Artificial Sequence
<220> FEATURE:
<223> OTHER INFORMATION: CCL23 fragment generated after incubation with
      activated neutrophil conditioned media or elastase

<400> SEQUENCE: 19

Leu Leu Asp Arg Phe His Ala Thr Ser Ala Asp Cys Cys Ile Ser Tyr
1               5                   10                  15

Thr Pro Arg Ser Ile Pro Cys Ser Leu Leu Glu Ser Tyr Phe Glu Thr
            20                  25                  30

Asn Ser Glu Cys Ser Lys Pro Gly Val Ile Phe Leu Thr Lys Lys Gly
        35                  40                  45

Arg Arg Phe Cys Ala Asn Pro Ser Asp Lys Gln Val Gln Val Cys Met
    50                  55                  60

Arg Met Leu Lys Leu Asp Thr Arg Ile Lys Thr Arg Lys Asn
65                  70                  75

<210> SEQ ID NO 20
<211> LENGTH: 73
<212> TYPE: PRT
<213> ORGANISM: Artificial Sequence
<220> FEATURE:
<223> OTHER INFORMATION: CCL23 fragment generated after incubation with
      chymase or cathepsin G

<400> SEQUENCE: 20

His Ala Thr Ser Ala Asp Cys Cys Ile Ser Tyr Thr Pro Arg Ser Ile
1               5                   10                  15

Pro Cys Ser Leu Leu Glu Ser Tyr Phe Glu Thr Asn Ser Glu Cys Ser
            20                  25                  30

Lys Pro Gly Val Ile Phe Leu Thr Lys Lys Gly Arg Arg Phe Cys Ala
        35                  40                  45

Asn Pro Ser Asp Lys Gln Val Gln Val Cys Met Arg Met Leu Lys Leu
    50                  55                  60

Asp Thr Arg Ile Lys Thr Arg Lys Asn
65                  70

<210> SEQ ID NO 21
<211> LENGTH: 70
<212> TYPE: PRT
<213> ORGANISM: Artificial Sequence
<220> FEATURE:
<223> OTHER INFORMATION: CCL23 fragment generated after incubation with
      activated neutrophil conditioned media or elastase

<400> SEQUENCE: 21

Ser Ala Asp Cys Cys Ile Ser Tyr Thr Pro Arg Ser Ile Pro Cys Ser
1               5                   10                  15

Leu Leu Glu Ser Tyr Phe Glu Thr Asn Ser Glu Cys Ser Lys Pro Gly
            20                  25                  30

Val Ile Phe Leu Thr Lys Lys Gly Arg Arg Phe Cys Ala Asn Pro Ser
        35                  40                  45

Asp Lys Gln Val Gln Val Cys Met Arg Met Leu Lys Leu Asp Thr Arg
    50                  55                  60

Ile Lys Thr Arg Lys Asn
65                  70
```

```
<210> SEQ ID NO 22
<211> LENGTH: 18
<212> TYPE: PRT
<213> ORGANISM: Artificial Sequence
<220> FEATURE:
<223> OTHER INFORMATION: SHAAGtide

<400> SEQUENCE: 22

Met Leu Trp Arg Arg Lys Ile Gly Pro Gln Met Thr Leu Ser His Ala
1               5                   10                  15

Ala Gly

<210> SEQ ID NO 23
<211> LENGTH: 15
<212> TYPE: PRT
<213> ORGANISM: Artificial Sequence
<220> FEATURE:
<223> OTHER INFORMATION: SHAAGtide variant

<400> SEQUENCE: 23

Arg Arg Lys Ile Gly Pro Gln Met Thr Leu Ser His Ala Ala Gly
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: SHAAGtide variant

<400> SEQUENCE: 24

Met Leu Trp Arg Arg Lys Ile Gly Pro Gln Met Thr Leu Ser His
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: SHAAGtide variant

<400> SEQUENCE: 25

Ile Gly Pro Gln Met Thr Leu Ser His Ala Ala Gly
1               5                   10

<210> SEQ ID NO 26
<211> LENGTH: 12
<212> TYPE: PRT
<213> ORGANISM: Artificial Sequence
<220> FEATURE:
<223> OTHER INFORMATION: SHAAGtide variant

<400> SEQUENCE: 26

Met Leu Trp Arg Arg Lys Ile Gly Pro Gln Met Thr
1               5                   10

<210> SEQ ID NO 27
<211> LENGTH: 18
<212> TYPE: PRT
<213> ORGANISM: Artificial Sequence
<220> FEATURE:
<223> OTHER INFORMATION: SHAAGtide variant
```

```
<400> SEQUENCE: 27

Met Leu Trp Arg Arg Lys Ile Gly Pro Gln Met Thr Leu Ser His Ala
1               5                   10                  15

Ala Tyr

<210> SEQ ID NO 28
<211> LENGTH: 16
<212> TYPE: PRT
<213> ORGANISM: Artificial Sequence
<220> FEATURE:
<223> OTHER INFORMATION: SHAAGtide variant

<400> SEQUENCE: 28

Trp Arg Arg Lys Ile Gly Pro Gln Met Thr Leu Ser His Ala Ala Gly
1               5                   10                  15

<210> SEQ ID NO 29
<211> LENGTH: 11
<212> TYPE: PRT
<213> ORGANISM: Artificial Sequence
<220> FEATURE:
<223> OTHER INFORMATION: SHAAGtide variant

<400> SEQUENCE: 29

Met Leu Trp Arg Arg Lys Ile Gly Pro Gln Met
1               5                   10

<210> SEQ ID NO 30
<211> LENGTH: 9
<212> TYPE: PRT
<213> ORGANISM: Artificial Sequence
<220> FEATURE:
<223> OTHER INFORMATION: SHAAGtide variant

<400> SEQUENCE: 30

Trp Arg Arg Lys Ile Gly Pro Gln Met
1               5

<210> SEQ ID NO 31
<211> LENGTH: 6
<212> TYPE: PRT
<213> ORGANISM: Artificial Sequence
<220> FEATURE:
<223> OTHER INFORMATION: SHAAGtide variant

<400> SEQUENCE: 31

Trp Arg Arg Lys Ile Gly
1               5

<210> SEQ ID NO 32
<211> LENGTH: 14
<212> TYPE: PRT
<213> ORGANISM: Artificial Sequence
<220> FEATURE:
<223> OTHER INFORMATION: SHAAGtide variant

<400> SEQUENCE: 32

Leu Trp Arg Arg Lys Ile Gly Pro Gln Met Thr Leu Ser His
1               5                   10

<210> SEQ ID NO 33
<211> LENGTH: 17
<212> TYPE: PRT
<213> ORGANISM: Artificial Sequence
<220> FEATURE:
<223> OTHER INFORMATION: SHAAGtide variant
```

```
<400> SEQUENCE: 33

Leu Trp Arg Arg Lys Ile Gly Pro Gln Met Thr Leu Ser His Ala Ala
1               5                   10                  15

Gly

<210> SEQ ID NO 34
<211> LENGTH: 54
<212> TYPE: DNA
<213> ORGANISM: Artificial Sequence
<220> FEATURE:
<223> OTHER INFORMATION: SHAAGtide polynucleotide variant

<400> SEQUENCE: 34
atgctctgga ggagaaagat tggtcctcag atgacccttt ctcatgctgc agga          54

<210> SEQ ID NO 35
<211> LENGTH: 45
<212> TYPE: DNA
<213> ORGANISM: Artificial Sequence
<220> FEATURE:
<223> OTHER INFORMATION: SHAAGtide polynucleotide variant

<400> SEQUENCE: 35
aggagaaaga ttggtcctca gatgacccct ttctcatgct gcagga                   45

<210> SEQ ID NO 36
<211> LENGTH: 45
<212> TYPE: DNA
<213> ORGANISM: Artificial Sequence
<220> FEATURE:
<223> OTHER INFORMATION: SHAAGtide polynucleotide variant

<400> SEQUENCE: 36
atgctctgga ggagaaagat tggtcctcag atgacccttt ctcat                    45

<210> SEQ ID NO 37
<211> LENGTH: 36
<212> TYPE: DNA
<213> ORGANISM: Artificial Sequence
<220> FEATURE:
<223> OTHER INFORMATION: SHAAGtide polynucleotide variant

<400> SEQUENCE: 37
attggtcctc agatgaccct ttctcatgct gcagga                              36

<210> SEQ ID NO 38
<211> LENGTH: 36
<212> TYPE: DNA
<213> ORGANISM: Artificial Sequence
<220> FEATURE:
<223> OTHER INFORMATION: SHAAGtide polynucleotide variant

<400> SEQUENCE: 38
atgctctgga ggagaaagat tggtcctcag atgacc                              36

<210> SEQ ID NO 39
<211> LENGTH: 54
<212> TYPE: DNA
<213> ORGANISM: Artificial Sequence
<220> FEATURE:
<223> OTHER INFORMATION: SHAAGtide polynucleotide variant

<400> SEQUENCE: 39
atgctctgga ggagaaagat tggtcctcag atgacccttt ctcatgctgc atat          54
```

```
<210> SEQ ID NO 40
<211> LENGTH: 48
<212> TYPE: DNA
<213> ORGANISM: Artificial Sequence
<220> FEATURE:
<223> OTHER INFORMATION: SHAAGtide polynucleotide variant

<400> SEQUENCE: 40
tggaggagaa agattggtcc tcagatgacc ctttctcatg ctgcagga          48

<210> SEQ ID NO 41
<211> LENGTH: 33
<212> TYPE: DNA
<213> ORGANISM: Artificial Sequence
<220> FEATURE:
<223> OTHER INFORMATION: SHAAGtide polynucleotide variant

<400> SEQUENCE: 41
atgctctgga ggagaaagat tggtcctcag atg                         33

<210> SEQ ID NO 42
<211> LENGTH: 27
<212> TYPE: DNA
<213> ORGANISM: Artificial Sequence
<220> FEATURE:
<223> OTHER INFORMATION: SHAAGtide polynucleotide variant

<400> SEQUENCE: 42
tggaggagaa agattggtcc tcagatg                                27

<210> SEQ ID NO 43
<211> LENGTH: 18
<212> TYPE: DNA
<213> ORGANISM: Artificial Sequence
<220> FEATURE:
<223> OTHER INFORMATION: SHAAGtide polynucleotide variant

<400> SEQUENCE: 43
tggaggagaa agattggt                                          18

<210> SEQ ID NO 44
<211> LENGTH: 42
<212> TYPE: DNA
<213> ORGANISM: Artificial Sequence
<220> FEATURE:
<223> OTHER INFORMATION: SHAAGtide polynucleotide variant

<400> SEQUENCE: 44
ctctggagga gaaagattgg tcctcagatg acctttctc at                42

<210> SEQ ID NO 45
<211> LENGTH: 92
<212> TYPE: PRT
<213> ORGANISM: Homo sapiens

<400> SEQUENCE: 45

Met Leu Trp Arg Arg Lys Ile Gly Pro Gln Met Thr Leu Ser His Ala
1               5                   10                  15

Ala Gly Phe His Ala Thr Ser Ala Asp Cys Cys Ile Ser Tyr Thr Pro
            20                  25                  30

Arg Ser Ile Pro Cys Ser Leu Leu Glu Ser Tyr Phe Glu Thr Asn Ser
        35                  40                  45

Glu Cys Ser Lys Pro Gly Val Ile Phe Leu Thr Lys Lys Gly Arg Arg
    50                  55                  60
```

```
Phe Cys Ala Asn Pro Ser Asp Lys Gln Val Gln Val Cys Met Arg Met
 65                  70                  75                  80

Leu Lys Leu Asp Thr Arg Ile Lys Thr Arg Lys Asn
                 85                  90
```

<210> SEQ ID NO 46
<211> LENGTH: 279
<212> TYPE: DNA
<213> ORGANISM: Homo sapiens

<400> SEQUENCE: 46

```
atgctctgga ggagaaagat tggtcctcag atgacccttt ctcatgctgc aggattccat      60
gctactagtg ctgactgctg catctcctac accccacgaa gcatcccgtg ttcactcctg     120
gagagttact tgaaacgaa cagcgagtgc tccaagccgg tgtcatctt cctcaccaag      180 aaggggcgac gtttctgtgc caaccccagt gataagcaag ttcaggtttg catgagaatg     240
ctgaagctgg acacacggat caagaccagg aagaattga                             279
```

<210> SEQ ID NO 47
<211> LENGTH: 137
<212> TYPE: PRT
<213> ORGANISM: Homo sapiens

<400> SEQUENCE: 47

```
Met Lys Val Ser Val Ala Ala Leu Ser Cys Leu Met Leu Val Thr Ala
 1               5                  10                  15

Leu Gly Ser Gln Ala Arg Val Thr Lys Asp Ala Glu Thr Glu Phe Met
                 20                  25                  30

Met Ser Lys Leu Pro Leu Glu Asn Pro Val Leu Leu Asp Met Leu Trp
             35                  40                  45

Arg Arg Lys Ile Gly Pro Gln Met Thr Leu Ser His Ala Ala Gly Phe
 50                  55                  60

His Ala Thr Ser Ala Asp Cys Cys Ile Ser Tyr Thr Pro Arg Ser Ile
 65                  70                  75                  80

Pro Cys Ser Leu Leu Glu Ser Tyr Phe Glu Thr Asn Ser Glu Cys Ser
                 85                  90                  95

Lys Pro Gly Val Ile Phe Leu Thr Lys Lys Gly Arg Arg Phe Cys Ala
            100                 105                 110

Asn Pro Ser Asp Lys Gln Val Gln Val Cys Met Arg Met Leu Lys Leu
        115                 120                 125

Asp Thr Arg Ile Lys Thr Arg Lys Asn
    130                 135
```

<210> SEQ ID NO 48
<211> LENGTH: 6
<212> TYPE: PRT
<213> ORGANISM: Artificial Sequence
<220> FEATURE:
<223> OTHER INFORMATION: W-tide

<400> SEQUENCE: 48

```
Trp Lys Tyr Met Val Met
 1               5
```

<210> SEQ ID NO 49
<211> LENGTH: 75
<212> TYPE: PRT
<213> ORGANISM: Artificial Sequence
<220> FEATURE:
<223> OTHER INFORMATION: CCL23 fragment -continued

```
<400> SEQUENCE: 49

Arg Phe His Ala Thr Ser Ala Asp Cys Cys Ile Ser Tyr Thr Pro Arg
1               5                   10                  15

Ser Ile Pro Cys Ser Leu Leu Glu Ser Tyr Phe Glu Thr Asn Ser Glu
            20                  25                  30

Cys Ser Lys Pro Gly Val Ile Phe Leu Thr Lys Lys Gly Arg Arg Phe
        35                  40                  45

Cys Ala Asn Pro Ser Asp Lys Gln Val Gln Val Cys Met Arg Met Leu
    50                  55                  60

Lys Leu Asp Thr Arg Ile Lys Thr Arg Lys Asn
65                  70                  75

<210> SEQ ID NO 50
<211> LENGTH: 116
<212> TYPE: PRT
<213> ORGANISM: Homo sapiens

<400> SEQUENCE: 50

Arg Val Thr Lys Asp Ala Glu Thr Glu Phe Met Met Ser Lys Leu Pro
1               5                   10                  15

Leu Glu Asn Pro Val Leu Leu Asp Met Leu Trp Arg Arg Lys Ile Gly
            20                  25                  30

Pro Gln Met Thr Leu Ser His Ala Ala Gly Phe His Ala Thr Ser Ala
        35                  40                  45

Asp Cys Cys Ile Ser Tyr Thr Pro Arg Ser Ile Pro Cys Ser Leu Leu
    50                  55                  60

Glu Ser Tyr Phe Glu Thr Asn Ser Glu Cys Ser Lys Pro Gly Val Ile
65                  70                  75                  80

Phe Leu Thr Lys Lys Gly Arg Arg Phe Cys Ala Asn Pro Ser Asp Lys
                85                  90                  95

Gln Val Gln Val Cys Met Arg Met Leu Lys Leu Asp Thr Arg Ile Lys
            100                 105                 110

Thr Arg Lys Asn
        115
```